(12) United States Patent
Yan et al.

(10) Patent No.: US 6,943,003 B2
(45) Date of Patent: Sep. 13, 2005

(54) ISOLATED HUMAN PHOSPHOLIPASE PROTEINS, NUCLEIC ACID MOLECULES ENCODING HUMAN PHOSPHOLIPASE PROTEINS, AND USES THEREOF

(75) Inventors: Chunhua Yan, Boyds, MD (US); Karen A Ketchum, Germantown, MD (US); Valentina Di Francesco, Rockville, MD (US); Ellen M Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 149 days.

(21) Appl. No.: 09/778,961

(22) Filed: Feb. 8, 2001

(65) Prior Publication Data

US 2004/0241793 A1 Dec. 2, 2004

(51) Int. Cl.[7] .............................. C12N 9/20; C12N 1/20; C12N 15/00; C07H 21/04
(52) U.S. Cl. ................. 435/198; 435/252.3; 435/320.1; 536/23.2
(58) Field of Search .............................. 435/198, 252.3, 435/320.1; 536/23.2

(56) References Cited

FOREIGN PATENT DOCUMENTS

| WO | WO 01 57188 A | 8/2001 |
|---|---|---|
| WO | WO 02 31161 A | 4/2002 |
| WO | WO 02 59328 A | 8/2002 |

OTHER PUBLICATIONS

Boll W. et al. "Messenger RNAs Expressed in Intestine of Adult but Not Baby Rabbits." Journal of Biological Chemistry, vol. 268, No. 17, Jun. 15, 1993. pp. 12901–12911. XP002200728.

Takemori et al. "Identification of Functional Domains of Rat Intestinal Phospholipase B/Lipase." Journal of Biological Chemistry, vol. 273, No. 4, Jan. 23, 1998, pp. 2222–2231. XP002222279.

Hillier et al. "zv97h009.s1 Soares_NhHMPu_S1 Homo Sapiens cDNA Clone IMAGE: 767777 3' Similar to SW: PHLX_RABIT Q05017 Phospholipase ADRAB–B Precursor, mRNA Sequence." Database EMBL, Heidelberg, FRG Online! May 14, 1997. Database accession No. AA418082. XP002234814.

NCI–CGAP "UI–H–BI4–aoe–g–11–O–UI.s1 NCI_CGAP_Sub8 Homo Sapiens cDNA Clone IMAGE: 3084860 3', mRNA Sequence." Database EMBL, Heidelberg, FRG Online! Dec. 8, 2000. Database accession No. BF510463. XP002234815.

NCI–CGAP "he10e12.x1 NCI_CGAP_CMLI Homo Sapiens cDNA Clone Image: 2918638 3' Similar to SW: PHLX_RABIT Q85017 Phospholipase ADRAB–B Precursor, Contains MER22.t1 MER22 Repetitive Element, mRNA Sequence." Database EMBL, Heidelberg, FRG Online? Mar. 2, 2000. Database accession No. AW467395. XP002234816.

Dias Neto et al. "MR2_EN0091–261200–007–b04 EN0091 Homo Sapiens cDNA, mRNA Sequence." Database EMBL, Heidelberg, FRG Online! Jan. 18, 2001. Database accession No. BF854199. XP002234817.

NCI/NINDS–CGAP: "7g10g10.x1 NCI_CGAP_Bm23 Homo Sapiens cDNA Clone IMAGE: 3306114 3' Similar to SW: PHLX_RABIT Q05017 Phospholipase DRAB–B Precursor, Contains MER22.t1 MER22 Repetitive Element, mRNA Sequence." Database EMBL, Heidelberg, FRG Online! Oct. 1, 2000. Database accession No. BE855594. XP002234818.

NCI–CGAP: "7e70h12.x1 NCI_CGAP_Pr28 Homo Sapiens cDNA Clone IMAGE: 3287879 3' Similar to SW: PHLX_RABIT Q05017 Phospholipase ADRAB–B Precursor, mRNA Sequence." Database EMBL, Heidelberg, FRG Online! Sep. 7, 2000. Database accession No. BE645470. XP002234819.

Dias Neto et al. "IL3–CT0220–031199–025–G12 CT0220 Homo Sapiens cDNA, mRNA Sequence." Database EMBL, Heidelberg, FRG 'Online! Apr. 30, 2000. Database accession No. AW752833. XP002234820.

Dias Neto et al. "MR2–EN0091–211200–003–c02 EN0091 Homo Sapiens cDNA, mRNA Sequence." Database EMBL, Heidelberg, FRG 'Online! Jan. 18, 2001. Database accession No. BF853588. XP002234821.

Hillier et al. "zv97h09.r1 Soares_NhHPu_S1 Homo Sapiens cDNA Clone IMAGE: 767777 5' Similar to SW: PHLX_RABIT Q05017 PHOSPHOLIPASE ADRAB–B PRECURSOR, mRNA Sequence." Database EMBL, Heidelberg, FRG Online! May 14, 1997. Database accession No. AA418228. XP002234822.

Dias Neto et al. "IL3–CT0220–150200–070–H02 CT0220 Homo Sapiens cDNA, mRNA Sequence." Database EMBL, Heidelberg, FRG 'Online! May 24, 2000. Database accession No. AW851123. XP002234823.

Sulston JE and Waterson R. "Homo Sapiens BAC Clone RP11–780J6 From 2, Complete Sequence." Database EMBL, Heidelberg, FRG 'Online! Jul. 11, 2000. Database accession No. AC074011. XP002234824.

*Primary Examiner*—Tekchand Saidha
(74) *Attorney, Agent, or Firm*—Celera Genomics; Lin Sun-Hoffman

(57) ABSTRACT

The present invention provides amino acid sequences of peptides that are encoded by genes within the human genome, the phospholipase peptides of the present invention. The present invention specifically provides isolated peptide and nucleic acid molecules, methods of identifying orthologs and paralogs of the phospholipase peptides, and methods of identifying modulators of the phospholipase peptides.

9 Claims, 42 Drawing Sheets

```
   1 CTGCAGCCAA CTTTGTTGAC CATCTCCCCA ATGCCTTGGA CGTCCTGCAT
  51 AGAGAGCTTT TCCCTTAGGT GCCCAGAGTC CTGGTCAACC TCGTGGACTT
 101 CCTGAACCCC ACTATCATGC GGCAGGTGTT CCTGGGAAAC CCAGACAAGT
 151 GCCCAGTGCA GCAGGCCAGA GCAGCATGCG CGAGCTGGTG GGGTCAGGCC
 201 GCTATGACAC GCAGGAGGAC TTCTCTGTGG TGCTGCAGCC CTTCTTCCAG
 251 AACATCCAGC TCCCTGTCCT GGCGCTTGAA CCACTTGGAA GCAAAACAGA
 301 GACCCTGGAC CTGAGAGCAG AGATGCCCAT CACCTGTCCC ACTCAGAATG
 351 AGCCCTTCCT GAGAACCCCT CGGAATAGTA ACTACACGTA CCCCATCAAG
 401 CCAGCCATTG AGAACTGGGG CAGTGACTTC CTGTGTACAG AGTGGAAGGC
 451 TTCCAATAGT GTTCCAACCT CTGTCCACCA GCTCCGACCA GCAGACATCA
 501 AAGTGGTGGC CGCCCTGGGT GACTCTCTGA CTACAGCAGT GGGAGCTCGA
 551 CCAAACAACT CCAGTGACCT ACCCACATCT TGGAGGGGAC TCTCTTGGAG
 601 CATTGGAGGG GATGGGAACT TGGAGACTCA CACCACACTG CCCAACATTC
 651 TGAAGAAGTT CAACCCTTAC CTCCTTGGCT TCTCTACCAG CACCTGGGAG
 701 GGGACAGCAG GACTAAATGT GGCAGCGGAA GGGGCCAGAG CTAGGGACAT
 751 GCCAGCCCAG GCCTGGGACC TGGTAGAGCG AATGAAAAAC AGCCCCGACA
 801 TCAACCTGGA GAAAGACTGG AAGCTGGTCA CACTCTTCAT TGGGGTCAAC
 851 GACTTGTGTC ATTACTGTGA GAATCCGGAG GCCCACTTGG CCACGGAATA
 901 TGTTCAGCAC ATCCAACAGG CCCTGGACAT CCTGTCTGAG GAGCTCCCAA
 951 GGGCTTTCGT CAACGTGGTG GAGGTCATGG AGCTGGCTAG CCTGTACCAG
1001 GGCCAAGGCG GGAAATGTGC CATGCTGGCA GCTCAGAACA ACTGCACTTG
1051 CCTCAGACAC TCGCAAAGCT CCCTGGAGAA GCAAGAACTG AAGAAAGTGA
1101 ACTGGAACCT CCAGCATGGC ATCTCCAGTT TCTCCTACTG GCACCAATAC
1151 ACACAGCGTG AGGACTTTGC GGTTGTGGTG CAGCCTTTCT TCCAAAACAC
1201 ACTCACCCCA CTGAACGAGA GAGGGACAC TGACCTCACC TTCTTCTCCG
1251 AGGACTGTTT TCACTTCTCA GACCGCGGGC ATGCCGAGAT GGCCATCGCA
1301 CTCTGGAACA ACATGCTGGA ACCAGTGGGC CGCAAGACTA CCTCCAACAA
1351 CTTCACCCAC AGCCGAGCCA AACTCAAGTG CCCCTCTCCT GAGAGCCCTT
1401 ACCTCTACAC CCTGCGGAAC AGCCGATTGC TCCCAGACCA GGCTGAAGAA
1451 GCCCCCGAGG TGCTCTACTG GGCTGTCCCA GTGGCAGCGG GAGTCGGCCT
1501 TGTGGTGGGC ATCATCGGGA CAGTGGTCTG GAGGTGCAGG AGAGGTGGCC
1551 GGAGGGAAGA TCCTCCAATG AGCCTGCGCA CTGTGGCCCT CTAGGCCCGG
1601 GGGTGGGTCC TCACCCTAAA CTCCCTATAG CCACTCTCTT CACCGCCCTC
1651 TGCCCCAGCC ACTCCCGGCC ACCAGGACAT GCTTCAATGC CTGGTTGCCAT
1701 AGGAAGCCCA GGGACAGTC ACAACTTCTT GGGGCCTGGG CTTCTTCCAG
1751 GCCTATGCTC CTGGAATGGA TACATTTAAA TAAAGTCCAA AGCTATTTTA
1801 AAAAAAAAAA AAAAAAAAAA AAAAAAAAAA AAAAA
```

FEATURES:
5'UTR:        1 - 175
Start Codon: 176
Stop Codon:  1592
3'UTR:       1595

Homologous proteins:
Top BLAST Hits
```
                                                                    Score    E
CRA|18OC0004885276 /altid=gi|464376  /def=sp|Q05017|PHLX_RABIT P...   750    0.0
CRA|18000005150386 /altid=gi|3172337 /def=gb|AAC40129.1| (AF045...   682    0.0
CRA|18000005121266 /altid=gi|2696236 /def=dbj|BAA23813.1| (D636...   665    0.0
CRA|18000005181876 /altid=gi|7498717 /def=pir||T20655 hypotheti...   228    9e-59
CRA|87000001028586 /altid=gi|7332170 /def=gb|AAF60857.1| (AC024...   210    3e-53
CRA|18000005040393 /altid=gi|7508802 /def=pir||T26083 hypotheti...   205    7e-52
CRA|89000000196200 /altid=gi|7293699 /def=gb|AAF49069.1| (AE003...   200    3e-50
CRA|89000000199135 /altid=gi|7297015 /def=gb|AAF52285.1| (AE003...   189    6e-47
CRA|18000004979533 /altid=gi|7499049 /def=pir||T16060 hypotheti...   161    2e-38
CRA|18000005184633 /altid=gi|7506410 /def=pir||T24016 hypotheti...   152    9e-36
CRA|18000005184632 /altid=gi|7506411 /def=pir||T24015 hypotheti...   122    1e-26
CRA|18000005182912 /altid=gi|7500588 /def=pir||T21835 hypotheti...   119    6e-26
CRA|87000001028649 /altid=gi|7332235 /def=gb|AAF60922.1| (AC006...   111    2e-23
```

FIGURE 1, page 1 of 2

```
BLAST dbEST hits:
gi|2079883  /dataset=dbest /taxon=9606 ...           724    0.0
gi|11593761 /dataset=dbest /taxon=960...             670    0.0
gi|7037501  /dataset=dbest /taxon=9606...            654    0.0
gi|12241943 /dataset=dbest /taxon=96...              632    e-179
gi|10367787 /dataset=dbest /taxon=960...             575    e-161
gi|9969781  /dataset=dbest /taxon=960...             547    e-153
gi|7667765  /dataset=dbest /taxon=9606...            531    e-148
gi|12241345 /dataset=dbest /taxon=96...              519    e-145
gi|2080047  /dataset=dbest /taxon=9606 ...           468    e-129
gi|7946640  /dataset=dbest /taxon=960...             323    7e-86
```

EXPRESSION INFORMATION FOR MODULATORY USE:
library source:
Expression information from BLAST dbEST hits:
```
gi|2079883   Mixed (melaonocyte, fetal heart, pregnant uterus)
gi|11593761  Kidney
gi|7037501   Whole blood
gi|12241943  Lung, normal
gi|10367787  brain glioblastoma
gi|9969781   Prostate
gi|7667765   Colon
gi|12241345  Lung, normal
gi|2080047   Mixed (melaonocyte, fetal heart, pregnant uterus)
gi|7946640   Colon
```

Expression information from PCR-based tissue screening panels:
Leukocyte

FIGURE 1, page 2 of 2

```
  1 MRELVGSGRY DTQEDFSVVL QPFFQNIQLP VLALEPLGSK TETLDLRAEM
 51 PITCPTQNEP FLRTPRNSNY TYPIKPAIEN WGSDFLCTEW KASNSVPTSV
101 HQLRPADIKV VAALGDSLTT AVGARPNNSS DLPTSWRGLS WSIGGDGNLE
151 THTTLPNILK KFNPYLLGFS TSTWEGTAGL NVAAEGARAR DMPAQAWDLV
201 ERMKNSPDIN LEKDWKLVTL FIGVNDLCHY CENPEAHLAT EYVQHIQQAL
251 DILSEELPRA FVNVVEVMEL ASLYQGQGGK CAMLAAQNNC TCLRHSQSSL
301 EKQELKKVNW NLQHGISSFS YWHQYTQRED FAVVVQPFFQ NTLTPLNERG
351 DTDLTFFSED CFHFSDRGHA EMAIALWNNM LEPVGRKTTS NNFTHSRAKL
401 KCPSPESPYL YTLRNSRLLP DQAEEAPEVL YWAVPVAAGV GLVVGIIGTV
451 VWRCRRGGRR EDPPMSLRTV AL
```

FEATURES:
Functional domains and key regions:
[1] PDOC00001 PS00001 ASN_GLYCOSYLATION
N-glycosylation site Number of matches: 5
    1      69-72 NYTY
    2     127-130 NNSS
    3     128-131 NSSD
    4     289-292 NCTC
    5     392-395 NFTH

[2] PDOC00004 PS00004 CAMP_PHOSPHO_SITE
cAMP- and cGMP-dependent protein kinase phosphorylation site 386-389 RKTT

[3] PDOC00005 PS00005 PKC_PHOSPHO_SITE
Protein kinase C phosphorylation site

Number of matches: 7
    1       7-9 SGR
    2      64-66 TPR
    3     135-137 SWR
    4     326-328 TQR
    5     365-367 SDR
    6     412-414 TLR
    7     466-468 SLR

[4] PDOC00006 PS00006 CK2_PHOSPHO_SITE
Casein kinase II phosphorylation site

Number of matches: 6
    1      12-15 TQED
    2      39-42 SKTE
    3      56-59 TQNE
    4     172-175 STWE
    5     298-301 SSLE
    6     326-329 TQRE

FIGURE 2, page 1 of 7

[5] PDOC00008 PS00008 MYRISTYL
N-myristoylation site

Number of matches: 8
    1    123-128  GARPNN
    2    138-143  GLSWSI
    3    144-149  GGDGNL
    4    147-152  GNLETH
    5    179-184  GLNVAA
    6    278-283  GGKCAM
    7    441-446  GLVVGI
    8    445-450  GIIGTV

[6] PDOC00009 PS00009 AMIDATION
Amidation site

Number of matches: 2
    1    384-387  VGRK
    2    457-460  GGRR

[7] PDOC00016 PS00016 RGD
Cell attachment sequence 349-351 RGD

[8] PDOC00200 PS00228 TUBULIN_B_AUTOREG
Tubulin-beta mRNA autoregulation signal 1-4 MREL

Membrane spanning structure and domains:

| Helix | Begin | End | Score | Certainty |
|---|---|---|---|---|
| 1 | 164 | 184 | 0.694 | Putative |
| 2 | 432 | 452 | 1.956 | Certain |

FIGURE 2, page 2 of 7

BLAST Alignment to Top Hit:
```
>CRA|18000004885276 /altid=gi|464376 /def=sp|Q05017|PHLX_RABIT
          PHOSPHOLIPASE ADRAB-B PRECURSOR /dataset=nraa
          /length=1458
       Length = 1458

Score =  750 bits (1915), Expect = 0.0
 Identities = 368/502 (73%), Positives = 407/502 (80%), Gaps = 33/502 (6%)

Query:    1  MRELVGSGRYDTQEDFSVVLQPFFQNIQLPVLA--------------------------   33
             +RELV SGRYDT+EDFSVVLQPFF +IQLPVL
Sbjct:  955  LRELVESGRYDTREDFSVVLQPFFHSIQLPVLQDGRLDTSFFAPDCVHPNQKFHSQLSRA 1014

Query:   34  -----LEPLGSKTETLDLRAEMPITCPTQNEPFLRTPRNSNYTYPIKPAIENWGSDFLCT   88
                  LEPLG KT+ LDL A + +TCPTQNEPFLRT RNS+YTYP +PA+ENWGSDFLCT
Sbjct: 1015  LWRNMLEPLGGKTDALDLTAAITLTCPTQNEPFLRTFRNSDYTYPSRPAVENWGSDFLCT 1074

Query:   89  EWKASNSVPTSVHQLRPADIKVVAALGDSLTTAVGARPNNSSDLPTSWRGLSWSIGGDGN  148
             W AS  VP SVH+L+P DIKVVAALGDSLT A+GARP+NSSD P  WRGLSWSIGGDG
Sbjct: 1075  AWNASRGVPNSVHELQPGDIKVVAALGDSLTLAMGARPSNSSDPPMFWRGLSWSIGGDGA 1134

Query:  149  LETHTTLPNILKKFNPYLLGFSTSTWEGTAGLNVAAEGARARDMPAQAWDLVERMKNSPD  208
             LETHTTLPNILKKFNP +LGFST T EGT GLNVA +GARA+DMPAQA DLVERM+NSP+
Sbjct: 1135  LETHTTLPNILKKFNPSILGFSTGTLEGTMGLNVAVQGARAQDMPAQARDLVERMRNSPE 1194

Query:  209  INLEKDWKLVTLFIGVNDLCHYCENPEAHLATEYVQHIQQALDILSEELPRAFVNVVEVM  268
             I+LEKDWKLVTLF+G NDLCH+C NPE        EYVQHIQQALD+L EELPR FVNVVEVM
Sbjct: 1195  IDLEKDWKLVTLFVGGNDLCHFCENPEGSSEGEYVQHIQQALDVLYEELPRTFVNVVEVM 1254

Query:  269  ELASLYQGQGGKCA-MLAAQNNCTCLRHSQSSLEKQELKKVNWNLQHGISSFSYWHQYTQ  327
             ELA L+Q QGG+CA +LAAQ++CTC ++SQSS+E QELKKVNWNLQ G+S  SY HQY Q
Sbjct: 1255  ELAGLHQDQGGRCATLLAAQSHCTCFKYSQSSVEMQELKKVNWNLQSGLSRLSYSHQYVQ 1314

Query:  328  REDFAVVVQPFFQNTLTPLNERGDTDLTFFSEDCFHFSDRGHAEMAIALWNNMLEPVGRK  387
             REDFAVVVQPFFQNTL PLN RGDTDLTFFS+DCFHFS+RGHAEMAIALWNNMLEPVG K
Sbjct: 1315  REDFAVVVQPFFQNTLVPLNGRGDTDLTFFSDDCFHFSERGHAEMAIALWNNMLEPVGHK 1374

Query:  388  TTSNNFTHSRAKLKCPSPESPYLYTLRNSRLLPDQAEEAPEVLYWAVPVAAGVGLVVGII  447
             TTSNNFT+SR KLKCPSP+SPYLYTLRNSRLLPDQAE  P VLYWAVPVAAG GL++GI+
Sbjct: 1375  TTSNNFTYSRTKLKCPSPDSPYLYTLRNSRLLPDQAEADPTVLYWAVPVAAGAGLLIGIL 1434

Query:  448  GTVVWRCRRGGRREDPPMSLRT  469
                V R R   REDPP+SL T
Sbjct: 1435  AMVAGRGMRCRPREDPPLSLST 1456

Score =  334 bits (847), Expect = 2e-90
 Identities = 191/445 (42%), Positives = 251/445 (55%), Gaps = 33/445 (7%)

Query:    4  LVGSGRYDTQEDFSVVLQPFFQNIQLPVLA------------------LEPLGSKTETL   44
             L+ S +Y+TQE F+VV QPFF    L  L                     +EP+G K E
Sbjct:  264  LLASSKYNTQESFAVVFQPFFYESSLSALLAEPPLQDPTTLALSLWNRMMEPIGRKEEPF  323

Query:   45  DLRAEMPITCPTQNEPFLRTPRNSNY----TYPIKPAIENWGSDFLCTEWKASNSVPTSV  100
             +     P+ CPTQ P+L T RNS       + P   G++  C +    S+SVPTSV
Sbjct:  324  SEKERKPLRCPTQESPYLFTYRNSGQLTRVSQPQGKLEVREGTEIRCPDKPSDSVPTSV  383

Query:  101  HQLRPADIKVVAALGDSLTTAVGA--RPNNSSDLPTSWRGLSWSIGGDGNLETHTTLPNI  158
             H+L+PADIKV+ A+GDSLT  GA  +P N  D+ T +RGLSWS+GGD N+ T TTL NI
Sbjct:  384  HRLKPADIKVIGAMGDSLTAGNGAGSQPGNILDVLTQYRGLSWSVGGDQNISTVTTLANI  443

Query:  159  LKKFNPYLLGFSTSTWEGT---AGLNVAAEGARARDMPAQAWDLVERMKNSPDINLEKDW  215
             L++FNP L GFS  T     A N A GARA +  QA LV MKN   IN ++DW
```

FIGURE 2, page 3 of 7

```
Sbjct: 444  LREFNPSLQGFSVGTGRETTSQAFFNQAVAGARADGLIPQAQRLVALMKNDTRINFQEDW 503

Query: 216  KLVTLFIGVNDLCHYCENPEAHLATEYVQHIQQALDILSEELPRAFVNVVEVME---LAS 272
            K++T+FIG NDLC +C +P +    + +I ALDIL E+PRAFVN+V+V+E    L
Sbjct: 504  KIITVFIGGNDLCDFCNDPVRYSPQNFTDNIGTALDILHAEIPRAFVNLVKVLEISKLRE 563

Query: 273  LYQGQGGKCAMLAAQNNCTC-LRHSQSSLEKQELKKVNWNLQHGISSFSYWHQYTQREDF 331
            LYQ  C +  ++ C C L+   +S E   L+     Q         +Y  R+DF
Sbjct: 564  LYQETKVSCPRMILRSLCPCVLKFDDNSTEIASLIETIKEYQERTQQLIDSGRYDTRDDF 623

Query: 332  AVVVQPFFQNTLTPLNERGDTDLTFFSEDCFHFSDRGHAEMAIALWNNMLEPVGRKTTSN 391
              VV+QPFF+    P + G D +FF+ DCFHFS + HA A ALWNNMLEPVG+KTT N
Sbjct: 624  TVVLQPFFEKVNMPKTQDGLPDNSFFAPDCFHFSSKAHAHAASALWNNMLEPVGQKTTHN 683

Query: 392  NFTHSRAKLKCPSPESPYLYTLRNS 416
            +F     + CP+   P+L T +NS
Sbjct: 684  DF-EGAVNITCPNQVWPFLSTYKNS 707

Score = 323 bits (819), Expect = 3e-87
Identities = 181/456 (39%), Positives = 261/456 (56%), Gaps = 51/456 (11%)

Query: 2    RELVGSGRYDTQEDFSVVLQPFFQNIQLPVLA--------------------------- 33
            ++L+ SGRYDT++DF+VVLQPFF+ + +P
Sbjct: 609  QQLIDSGRYDTRDDFTVVLQPFFEKVNMPKTQDGLPDNSFFAPDCFHFSSKAHAHAASAL 668

Query: 34   ----LEPLGSKTETLDLRAEMPITCPTQNEPFLRTPRNSNYTYPIKPAIENWGSDFLCTE 89
                LEP+G  KT  D  + ITCP Q   PFL T +NS         ++ +G+    C +
Sbjct: 669  WNNMLEPVGQKTTHNDFEGAVNITCPNQVWPFLSTYKNS---------VQGFGTWLPCRD 719

Query: 90   WKASNSVPTSVHQLRPADIKVVAALGDSLTTAVG--ARPNNSSDLPTSWRGLSWSIGGDG 147
             S S PTSVH LRPADI+VVAALGDSLT +G  ++PN+ SD  T +RGLS+S GGDG
Sbjct: 720  RSPSASPPTSVHALRPADIQVVAALGDSLTAGIGIGSKPNDLSDGTTQYRGLSYSSGGDG 779

Query: 148  NLETHTTLPNILKKFNPYLLGFSTSTWEGT----AGLNVAAEGARARDMPAQAWDLVERMK 204
            +L+  TTLPNIL++FN  L+GF+   T +   A  N A  GA+ARD+ +Q    LV+RMK
Sbjct: 780  SLDNVTTLPNILRQFNSNLMGFAVGTGDASGTNAFFNQAVPGAKARDLMSQVQTLVQRMK 839

Query: 205  NSPDINLEKDWKLVTLFIGVNDLCHYCENPEAHLATEYVQHIQQALDILSEELPRAFVNV 264
            +   +N ++DWK++T+ IG +D C YC +    A + H++ ALD L E+PRA VN+
Sbjct: 840  DDHRVNFQEDWKVITVQIGASDLCDYCTDSNLYSAANFYDHLRDALDALHREVPRALVNL 899

Query: 265  VEVME----LASLYQGQGGKCAMLAAQNNCTC-LRHSQSSLEKQELKKVNWNLQHGISSFS 320
            V+ M       ++ G   KC + A   C C L  ++S E  L++    Q   +
Sbjct: 900  VDFMNPSVTRQVFLGNPDKCPVQQASALCNCVLSPRENSYELARLEALAQAYQSSLRELV 959

Query: 321  YWHQYTQREDFAVVVQPFFQNTLTPLNERGDTDLTFFSEDCFHFSDRGHAEMAIALWNNM 380
            +Y  REDF+VV+QPFF +    P+ + G  D +FF+ DC H + + H++++  ALW NM
Sbjct: 960  ESGRYDTREDFSVVLQPFFHSIQLPVLQDGRLDTSFFAPDCVHPNQKFHSQLSRALWRNM 1019

Query: 381  LEPVGRKTTSNNFTHSRAKLKCPSPESPYLYTLRNS 416
            LEP+G KT + + T  +   L CP+   P+L T RNS
Sbjct: 1020 LEPLGGKTDALDLT-AAITLTCPTQNEPFLRTFRNS 1054

Score = 137 bits (341), Expect = 3e-31
Identities = 107/338 (31%), Positives = 161/338 (46%), Gaps = 42/338 (12%)

Query: 85   FLCTEWKASNSVPT-SVHQLRPADIKVVAALGDSLTTAVGARPNNSSDLPTSWRGLSWSI 143
             F C    +  SVP+ SVH LRP+DIK VAA+G+  T         +       TR      +
Sbjct: 46   FPCDPKTLAESVPSESVHSLRPSDIKFVAAIGNVETAPDSGADDLEEQDGTEKRPEQACM 105

Query: 144  GGDGNLETHTTLPNILKKFNPY-LLGFSTSTWEGTAGLNVAAEGARARDMPAQAWDLVER 202
```

FIGURE 2, page 4 of 7

```
                    G       T L +I+ +F+P  L+         T         +   G  A D+  QA +LV
Sbjct: 106  G------VVTVLSDIIGRFSPSALMPLCPET-------RLVPRGG-AEDLWMQATELVRS 151

Query: 203  MKNSPDINLEKDWKLVTLFIGVNDLCHYCENPEAH-LATEYVQHIQQALDILSEELPRAF 261
            M+ +P ++ E DWKL+ +F       C  C - +  L      + + + LD L +E+P+AF
Sbjct: 152  MRENPQLDFEHDWKLINVFFSNTSQCFPCPSAQQKGLVLGGMDKLTRTLDYLQQEVPKAF 211

Query: 262  VNVVEVMELASLYQGQGGKCAMLAAQNNCTCLRHSQSSLEKQELKKV--NWNLQHGISSF 319
            VN+V++ ELA+ + + G   + A  C CLR       E +L KV    W+         S
Sbjct: 212  VNLVDLSELAAFSRWRQG-AQLSPAAEPCRCLR------ETSQLTKVLTQWSYLEAWDSL 264

Query: 320  SYWHQYTQREDFAVVVQPFF-QNTLTPLNERGDTDLTFFSEDCFHFSDRGHAEMAIALWN 378
              +Y   +E FAVV QPFF +++L+  L                +     +A++LWN
Sbjct: 265  LASSKYNTQESFAVVFQPFFYESSLSALLAEPPL--------------QDPTTLALSLWN 310

Query: 379  NMLEPVGRKTTSNNFTHSRAKLKCPSPESPYLYTLRNS 416
            M+EP+GRK     +   R  L+CP+ ESPYL+T RNS
Sbjct: 311  RMMEPIGRKEEPFS-EKERKPLRCPTQESPYLFTYRNS 347

>CRA|18000005150386 /altid=gi|3172337 /def=gb|AAC40129.1| (AF045454)
          phospholipase B [Cavia porcellus] /org=Cavia porcellus
          /taxon=10141 /dataset=nraa /length=1463
          Length = 1463

Score =  682 bits (1741), Expect = 0.0
 Identities = 348/505 (68%), Positives = 389/505 (76%), Gaps = 38/505 (7%)

Query: 1     MRELVGSGRYDTQEDFSVVLQPFFQNIQLPVLA-------------------------- 33
             MRELV SGRYDT+EDFSVVLQPFF NI+LP+L
Sbjct: 954   MRELVESGRYDTREDFSVVLQPFFLNIRLPILEDGRPDTSFFAPDCINPGQKFHSQLSRA 1013

Query: 34    -----LEPLGSKTETLDLRAEMPITCPTQNEPFLRTPRNSNYTYPIKPAIENWGSDFLCT 88
                  LEP+GSKT+TLDL A++ + CPTQ EPFLRTP+NS+YTYP KPAIENWGSDFLCT
Sbjct: 1014  LWVNMLEPVGSKTDTLDLTADISLPCPTQEEPFLRTPQNSDYTYPTKPAIENWGSDFLCT 1073

Query: 89    EWKASNSVPTSVHQLRPADIKVVAALGDSLTTAVGARPNNSSDLPTSWRGLSWSIGGDGN 148
             EWK SNSVPTSVH+L+PADIKVVAALGDSLTTAVGAR +NSSDL  SWRGLSWSIGGDG
Sbjct: 1074  EWKPSNSVPTSVHKLQPADIKVVAALGDSLTTAVGARASNSSDLLMSWRGLSWSIGGDGA 1133

Query: 149   LETHTTLPNILKKFNPYLLGFSTSTWEGTAGLNVAAEGARARDMPAQAWDLVERMKNSPD 208
             LETHTTLPNILKKFNP + GFST T E TAG NVA E ARARDMPAQA DLVERMK S +
Sbjct: 1134  LETHTTLPNILKKFNPSIFGFSTGTLEETAGFNVAVEEARARDMPAQARDLVERMKASTE 1193

Query: 209   INLEKDWKLVTLFIGVNDLCHYCENPEAHLATEYVQHIQQALDILSEELPRAFVNVVE-V 267
             INLE DWKL+TLFIG NDLCHYC+NPE H A EYVQHI+QALDIL EELPRAF+NVV+ +
Sbjct: 1194  INLEMDWKLITLFIGSNDLCHYCDNPENHSAEEYVQHIRQALDILYEELPRAFINVVDII 1253

Query: 268   MELASLYQGQGGKC-AMLAAQNNCTCLRHSQSSLEKQELKKVNWNLQHGISSFSYWHQYT 326
             MELA L+QGQGG C A+L AQ+ C+CLRH SS  QELKKV WNLQ +S SY +YT
Sbjct: 1254  MELAGLHQGQGGHCTALLPAQSTCSCLRHFPSSPVIQELKKVTWNLQSDMSRLSYQEKYT 1313

Query: 327   QREDFAVVVQPFFQNTLTPLNERGDTDLTFFSEDCFHFSDRGHAEMAIALWNNMLEPVGR 386
             QREDFAVVVQPFFQNTL PL++ G TD TFFSEDC HFS+RGHAEMAIALWNNMLEPVG
Sbjct: 1314  QREDFAVVVQPFFQNTLIPLDKLGSTDPTFFSEDCLHFSERGHAEMAIALWNNMLEPVGH 1373

Query: 387   KTTSNNFTHSRAKLKCPSPESPYLYTLRNSRLLPDQAEEAPEVLYWAVPVAAG----VGL 442
             KTT NNFT++R KLKCPS ESPYLYTL+NS LP Q E+A V   V AA      VGL
Sbjct: 1374  KTTFNNFTYNRTKLKCPSTESPYLYTLQNSLSLPVQTEKASGVAPGIVSAAAAGGLLVGL 1433

Query: 443   VVGIIGTVVWRCRRGGRREDPPMSL 467
             +VGI+   +W  R    +++ PP S+
Sbjct: 1434  IVGILAVSLWSSFRRRQKKSPPESV 1458
```

FIGURE 2, page 5 of 7

```
Score = 348 bits (884), Expect = 7e-95
Identities = 199/442 (45%), Positives = 257/442 (58%), Gaps = 31/442 (7%)

Query:   4   LVGSGRYDTQEDFSVVLQPFFQNIQLPV----------LAL-------EPLGSKTETLDL  46
             L+ S ++ QE F+VV QPFF + PV          LAL        +P+G K E
Sbjct: 265   LLASSSFNDQESFAVVFQPFFYEVSSPVEEPPSQDPTTLALSLWNNMMKPVGQKDEPFST 324

Query:  47   RAEMPITCPTQNEPFLRTPRNSNYTYPI----KPAIENWGSDFLCTEWKASNSVPTSVHQ 102
             P+ CP+Q P+L T RNSNY   +    + E G++ C +   S+S PTSVH+
Sbjct: 325   IERRPMKCPSQESPYLFTYRNSNYQSRLLKRQRQHKEREGTEIRCPDKDPSDSTPTSVHR 384

Query: 103   LRPADIKVVAALGDSLTTAVGA--RPNNSSDLPTSWRGLSWSIGGDGNLETHTTLPNILK 160
             L+PADIKV+ ALGDSLT  GA RP N  D+ T +RGLSWSIG D N+ + TTLPNIL+
Sbjct: 385   LKPADIKVIGALGDSLTAGNGAGSRPGNILDVLTEYRGLSWSIGADHNISSVTTLPNILR 444

Query: 161   KFNPYLLGFSTSTWEGT---AGLNVAAEGARARDMPAQAWDLVERMKNSPDINLEKDWKL 217
             +FNP L GFST T +    A N A  GARA D+  QA  LV+ MKN  IN E+DWK+
Sbjct: 445   EFNPSLKGFSTGTGKANSVGAFFNQAVAGARAGDLIPQARTLVDLMKNHTSINFEEDWKI 504

Query: 218   VTLFIGVNDLCHYCENPEAHLATEYVQHIQQALDILSEELPRAFVNVVEVME---LASLY 274
             +T+FIG NDLC +C +P +   + +I+QALDIL  E+PRAFVN+V+V++    L  LY
Sbjct: 505   ITVFIGGNDLCDFCSDPVTNSPENFTDNIRQALDILHAEVPRAFVNMVKVLQIVNLRELY 564

Query: 275   QGQGGKCAMLAAQNNCTC-LRHSQSSLEKQELKKVNWNLQHGISSFSYWHQYTQREDFAV 333
             +     C L +N C C L   +S E + L +N Q         +Y  REDF V
Sbjct: 565   KDSRVSCPRLILRNLCRCVLLPDDNSTELESLIDINKKYQERTHQLIESGRYDTREDFTV 624

Query: 334   VVQPFFQNTLTPLNERGDTDLTFFSEDCFHFSDRGHAEMAIALWNNMLEPVGRKTTSNNF 393
             V+QPFF+    P   G  D T F+ DCFHFS + HA  A ALW NMLEPVG+KTT NNF
Sbjct: 625   VLQPFFEKVDIPKTSEGLPDNTSFAPDCFHFSSKTHARAASALWKNMLEPVGQKTTQNNF 684

Query: 394   THSRAKLKCPSPESPYLYTLRN 415
             +S   + CP+   PYL T +N
Sbjct: 685   ENS-IDIICPNQAFPYLSTYKN 705

Score = 314 bits (795), Expect = 2e-84
Identities = 178/455 (39%), Positives = 259/455 (56%), Gaps = 51/455 (11%)

Query:   3   ELVGSGRYDTQEDFSVVLQPFFQNIQLPVLA---------------------------   33
             +L+ SGRYDT+EDF+VVLQPFF+ + +P +
Sbjct: 609   QLIESGRYDTREDFTVVLQPFFEKVDIPKTSEGLPDNTSFAPDCFHFSSKTHARAASALW 668

Query:  34   ---LEPLGSKTETLDLRAEMPITCPTQNEPFLRTPRNSNYTYPIKPAIENWGSDFLCTEW  90
                LEP+G KT +   +  I CP Q P+L T +N        IE G+   C E
Sbjct: 669   KNMLEPVGQKTTQNNFENSIDIICPNQAFPYLSTYKNG--------IEGHGTWLTCRER  719

Query:  91   KASNSVPTSVHQLRPADIKVVAALGDSLT--TAVGARPNNSSDLPTSWRGLSWSIGGDGN 148
              S S PTSVH LRPAD++VVAALGDSLT  + +G++P + +D+ T +RGLS+S GGDG+
Sbjct: 720   TPSASPPTSVHALRPADVRVVAALGDSLTAGSGIGSKPGDLADVITQYRGLSYSSGGDGS 779

Query: 149   LETHTTLPNILKKFNPYLLGFSTSTWEGT---AGLNVAAEGARARDMPAQAWDLVERMKN 205
             L   TTLPNIL++FN  L G++ T + +    A LN A  GA+A ++ +Q  LV++MK+
Sbjct: 780   LMNVTTLPNILREFNSNLTGYAVGTGDASNTNAFLNQAVPGAKAEEELMSQVKTLVQKMKD 839

Query: 206   SPDINLEKDWKLVTLFIGVNDLCHYCENPEAHLATEYVQHIQQALDILSEELPRAFVNVV 265
             P IN  +DWK++T+ IG NDLC++C + +  +  +   H+  ALDIL E+PRA VN+V
```

FIGURE 2, page 6 of 7

```
Sbjct:  840   DPRINFHEDWKVITVLIGTNDLCNHCTDLDLYSSANFFNHLLNALDILHREVPRALVNLV  899

Query:  266   EVME---LASLYQGQGGKCAMLAAQNNCTC-LRHSQSSLEKQELKKVNWNLQHGISSFSY  321
              + M    + ++ G  KC + A  C C L  ++S E   +    Q  +
Sbjct:  900   DFMNPSIMRQVFLGNPDKCPVQQASILCNCVLSLRENSYELARMDALTRAYQSSMRELVE  959

Query:  322   WHQYTQREDFAVVQPFFQNTLTPLNERGDTDLTFFSEDCFHFSDRGHAEMAIALWNNML   381
              +Y  REDF+VV+QPFF N    P+ E G  D +FF+ DC +    + H++++ ALW NML
Sbjct:  960   SGRYDTREDFSVVLQPFFLNIRLPILEDGRPDTSFFAPDCINPGQKFHSQLSRALWVNML 1019

Query:  382   EPVGRKTTSNNFTHSRAKLKCPSPESPYLYTLRNS 416
              EPVG KT + + T +    L CP+ E P+L T +NS
Sbjct: 1020   EPVGSKTDTLDLT-ADISLPCPTQEEPFLRTPQNS 1053

Score =  155 bits (389), Expect = 8e-37
 Identities = 110/351 (31%), Positives = 166/351 (46%), Gaps = 48/351 (13%)

Query:   85   FLCTEWKASNSVPT-SVHQLRPADIKVVAALGDSLTTAVGARPNNSSDLPTS---WRGLS  140
              F C+   K    ++P+ SVH L PADIK++AA+GD  T      N +   T   WRG
Sbjct:   45   FSCSPKKLGLNMPSESVHTLTPADIKLIAAIGDMETPPDSGAVNLDTSERTEKEPWRGCM  104

Query:  141   WSIGGDGNLETHTTLPNILKKFNPYLLGFSTSTWEGTAGLNVAAEGARARDMPAQAWDLV  200
                          T L +I+ FNP +L  +       W         AA     ++  QA +LV
Sbjct:  105   GMM---------TVLSDIISHFNPSVLLPTCPPWRS------AAVRGGVEELRTQAEELV  149

Query:  201   ERMKNSPDINLEKDWKLVTLFIGVNDLCHYCENPEAHLATEYVQHIQQ---ALDILSEEL  257
              +K +P ++  ++DWKL+ +F     LC+  C  P AH     + ++ +        L  L +E+
Sbjct:  150   SSLKKNPQLDFQQDWKLINVFFSNASLCYLC--PSAHENGPLMSNMDKLAGILHYLHQEV  207

Query:  258   PRAFVNVVEVMELASLYQGQGGKCAMLAAQNNCTCLRHSQSSLEKQELKKVNWNLQHGIS  317
              PRAFVN+V++  E+ ++ +    G    +  C C      K +   + W+ Q
Sbjct:  208   PRAFVNLVDLFEVVAMPRWHQCTMLSRPSPEACGC----SGETSKLDTVVMQWSYQETWD  263

Query:  318   SFSYWHQYTQREDFAVVQPFFQNTLTPLNERGDTDLTFFSEDCFHFSDRGHAEMAIALW   377
              S    + +E FAVV QPFF   +P+ E   D T                 +A++LW
Sbjct:  264   SLLASSSFNDQESFAVVFQPFFYEVSSPVEEPPSQDPT--------------TLALSLW   308

Query:  378   NNMLEPVGRKTTSNNFTHSRAKLKCPSPESPYLYTLRN----SRLLPDQAE   424
              NNM++PVG+K   +  T  R  +KCPS ESPYL+T RN    SRLL  Q +
Sbjct:  309   NNMMKPVGQKDEPFS-TIERRPMKCPSQESPYLFTYRNSNYQSRLLKRQRQ   358
```

Hmmer search results (Pfam):

| Model | Description | Score | E-value | N |
|---|---|---|---|---|
| PF00657 | Lipase/Acylhydrolase with GDSL-like motif | 158.4 | 1.6e-45 | 1 |
| PF01347 | Lipoprotein amino terminal region | 1.9 | 6.1 | 1 |
| CE00543 | CE00543 steroid_receptor_N10 | -0.8 | 1.5 | 1 |

Parsed for domains:

| Model | Domain | seq-f | seq-t | hmm-f | hmm-t | score | E-value |
|---|---|---|---|---|---|---|---|
| PF01347 | 1/1 | 155 | 172 .. | 636 | 653 .. | 1.9 | 6.1 |
| PF00657 | 1/1 | 110 | 233 .. | 1 | 146 [] | 158.4 | 1.6e-45 |
| CE00543 | 1/1 | 230 | 254 .. | 456 | 480 .. | -0.8 | 1.5 |

FIGURE 2, page 7 of 7

```
   1 ATTCTGCAGC CAACTTTGTT GACCATCTCC GCAATGCCTT GGACGTCCTG
  51 CATAGAGAGG TGGGTGGGGG GCTTCCACAA GCTGGTAACA GCTCAAGCAT
 101 GGTGAGGGTG AAGGTGGATG GGGGGAAAGA ATGAGAGAAG AACCCCTTTC
 151 TCTCAAGGAG ACAGCCAAGG GCATGGANNN NNNNNNNNNN NNNNNNNNNN
 201 NNNNNNNNNN NNNNNNNNNN NNNNNNNNNN NNNNNNNNNN NNNNNNNNNN
 251 NNNNNNNNNN NNNNNNNNNN NNNNNNNNNN NNNNNNNNNN NNNNNNNNNN
 301 NNNNNNNNNN NNNNNNNNNN NNNNNNNNNN NNNNNNNNNN NNNNNNNNNN
 351 NNNNNNNNNN NNNNNNNNNN NNNNNNNNNN NNNNNNNNNN NNNNNNNNNN
 401 NNNNNNNNNN NNNNNNNNNN NNNNNNNNNN NNNNNNNNNN NNNNNNNNNN
 451 NNNNNNNNNN NNNNNNNNNN NNNNNNNNNN NNNNNNNNNN NNNNNNNNNN
 501 NNNNNNNNNN NNNNNNNNNN NNNNNNNNNN NNNNNNNNNN NNNNNNNNNN
 551 NNNNNNNNNN NNNNNNNNNN NNNNNNNNNN NNNNNNNNNN NNNNNNNNNN
 601 NNNNNNNNNN NNNNNNNNNN NNNNNNNNNN NNNNNNNNNN NNNNNNNNNN
 651 NNNNNNNNNN NNNNNNNNNN NNNNNNNNNN NNNNNNNNNN NNNNNNNNNN
 701 NNNNNNNNNN NNNNNNNNNN NNNNNNNNNN NNNNNNNNNN NNNNNNNNNN
 751 NNNNNNNNNN NNNNNNNNNN NNNNNNNNNN NNNNNNNNNN NNNNNNNNNN
 801 NNNNNNNNNN NNNNNNNNNN NNNNNNNNNN NNNNNNNNNN NNNNNNNNNN
 851 NNNNNNNNNN NNNNNNNNNN NNNNNNNNNN NNNNNNNNNN NNNNNNNNNN
 901 NNNNNNNNNN NNNNNNNNNN NNNNNNNNNN NNNNNNNNNN NGTGCCATTG
 951 CCGCTGCAGC CCCTTTGGGT GGCACCCATG GAGTTGTGTG ATGTACGGCC
1001 TGTAAGGCCT TACGAGGTAG CCCTGTATAG ACTCCTCCCC AGAACTCAAC
1051 TCCAGAAAGA CCAAGCTGGA TTGCTAAAGG AACCATTCC TAGGGGCCCT
1101 GAGACAGCCC CAGGAAGAAG TGCCTGGAGC CCCCTCTCA TCTGCAGCTT
1151 TTCCCTTAGG TGCCCAGAGT CCTGGTCAAC CTCGTGGACT TCCTGAACCC
1201 CACTATCATG CGGCAGGTGT TCCTGGGAAA CCCAGACAAG TGCCCAGTGC
1251 AGCAGGCCAG GTAGGCAGGT CCTGGCTGTC CCCACACTGG AGATGCCCTC
1301 ACCTCCTGGT CTGGCCCACA TGCAGTGGTG ATGCCTCAGG GTCTTTGTGA
1351 CTTGGTCTAT CCATGTGTCC AAGTCTGTAA AGGAGGACTT CTGCCAGAAC
1401 GTCCCCTTCC AGAGGCTGGA GCCATGACTC CCTGTTACC CAACTTCAAG
1451 GTGCCTGGCA GGAACTTCTA TGATACCAGG CAGCCACAGA GGGGAGGGAT
1501 CAAAGTTGGG ACAGAGGCTG GTGTTTGAGA GACAGGATAG CCTAGACTGT
1551 GAACATGGGC AGTGGTTAGG GATGTAGACA TATGTGGTCA AACTGTAACA
1601 GAAAGCAAGG AAAAGGTACA AGCAACTCAG TTACCTTTAG GGGAAGAAGA
1651 GAATTAGGAG GGACACAGGG AGCTTCAAAC TGGGAGTGTT TTGTTTCTTA
1701 AACTGGGCCA TAAGTACATG GATGTGTGTT TTATTATTCT TTATATCTTA
1751 CACATCTATT TACTCAGCAA ATCTTACAGA ACTTCCTGTG TACCAGGCAT
1801 TGTTTCAAGT GCTTTAGAAA TCTCTCTCTT AAGTAGATGT GATGGGTGTG
1851 AAATAATTCA TGATGAAACC AAAGGGGACA CAGTAGGGCA CTCATGTGAA
1901 AGAAGGAGAG GTCTAAGGCA TAGCATCAGA GGCCCAAAA TATCAGCTCC
1951 AACACCAGAG GATGCATTTT CTTTTTAATT AAACACTAAA TTTTCACTGC
2001 CCAAATTCAT TTGCTCAGCT GAATAATCGG TTGCAGGCCC AGCACCTGCA
2051 GTCCAACACT TGTGCTCTGT TGGTATGAGA GGGTGCTCAT TCCCACGCTG
2101 GCTCCCTCCC TCGGGCCATC TCCAGTGCCC CTGCCAGGCC TGAAGCCTGC
2151 CCCTGAGCAT GTGCGCCAGA GCCTCAAGGC TTGAGTGCTC CTAAACCAGG
2201 GCGGGAGGGA GCCTCTCCAC CCCTCCCCTG AACCTGGGCA ATCAGAACCA
2251 GCCCCTGATG GAAGCCTGAG CTCTGGGCC TCCTGCCTCC CCCTCTTTGT
2301 GCAGCGTTTT GTGTAACTGC GTTCTGACCC TGCGGGAGAA CTCCCAAGAG
2351 CTAGCCAGGC TGGAGGCCTT CAGCCGAGCC TACCGGGTAA GACCAAGAAG
2401 GGCACCATGC TGTGTCCTCT CCCCTACGTT CACTCTAACA CACAGCCCAG
2451 AGCCCCTAGA GGAGGCACAC AGGGAAGGAA AAGCTGGTCA GGGATTGTGG
2501 GGAGACGGGG AGCAGCCTGG GTGCCTTCCT CTGTCTCACG TGACTGTGGT
2551 GTCTCAGGTG CCCTGGTTGG AATCATCCCA GTAGGATCCA GGTGGAAAAG
2601 CCCTCATGGC CCAGCTACCG TTGAGGGCTT AACCCCAACT CCTGGCCCGT
2651 AGCCCTGGAT GCCTCATGAG ACCACCTTTC CCTCCCCAC TCCCACTCCA
2701 AAGGCAGGTG CCGAGCCTCT GGAGGTTCTT CCCAGGTTTT TATCCCTTTT
2751 GGGACTTCCT GCCTAGCCCT TCAGAGAGAG TAGTCTACTT ACAATCAAAA
2801 CAAAAAGGTG ACCCAACCTG TTTCCAAATT CTCTGGAAAA GGACTTGCCC
2851 TCAGGTGATT TGTGTTCTCA AGGGAAAGGC TGAGTCGGCC CCTCCATCCA
2901 GGGAGATGGA CTGCCCACCA CCCCTACTCT TGCCTCACTG GGTCCTGGGC
2951 CCACCCAGGG CCTGGGCTGA AGACCCTGTG CATGTGTCCC CAGAGCAGCA
3001 TGCGCGAGCT GGTGGGGTCA GGCCGCTATG ACACGCAGGA GGACTTCTCT
3051 GTGGTGCTGC AGCCCTTCTT CCAGAACATC CAGCTCCCTG TCCTGGTGGT
3101 ATGTCCCCTG CCCTCGCCCA TGGTACTCTT TTAGAGGAAG AAATGCAAGG
```

FIGURE 3, page 1 of 33

```
3151 CAGAATTGCC AGTTGCTTCC ACGAGCATGT GCATAAAATG GGAAAGACAC
3201 AGCTCTCCAG ACGCTGNNNN NNNNNNNNNN NNNNNNNNNN NNNNNNNNNN
3251 NNNNNNNNNN NNNNNNNNNN NNNNNNNNNN NNNNNNNNNN NNNNNNNNNN
3301 NNNNNNNNNN NNNNNNNNNN NNNNNNNNNN NNNNNNNNNN NNNNNNNNNN
3351 NNNNNNNNNN NNNNNNNNNN NNNNNNNNNN NNNNNNNNNN NNNNNNNNNN
3401 NNNNNNNNNN NNNNNNNNNN NNNNNNNNNN NNNNNNNNNN NNNNNNNNNN
3451 NNNNNNNNNN NNNNNNNNNN NNNNNNNNNN NNNNNNNNNN NNNNNNNNNN
3501 NNNNNNNNNN NNNNNNNNNN NNNNNNNNNN NNNNNNNNNN NNNNNNNNNN
3551 NNNNNNNNNN NNNNNNNNNN NNNNNNNNNN NNNNNNNNNN NNNNNNNNNN
3601 NNNNNNNNNN NNNNNNNNNN NNNNNNNNNN NNNNNNNNNN NNNNNNNNNN
3651 NNNNNNNNNN NNNNNNNNNN NNNNNNNNNN NNNNNNNNNN NNNNNNNNNN
3701 NNNNNNNNNN NNNNNNNNNN NNNNNNNNNN NNNNNNNNNN NNNNNNNNNN
3751 TTGTGGGATC GCTCTGATCT CTCTGTTAAG TGAATGGGCC CTGTGGTGGC
3801 TGGTGACCTG GAGCACTCCA GGGGAAGGAA GGTGTTGAGT GGTCAGTCCC
3851 AGGGCCAAGT CCGCTGGTGG TGGCTCCCTC TGAACCAATA GGATCTTGAG
3901 GGGGTATATT GGTCTCTTTC AGGATGGGCT CCCAGATACG TCCTTCTTTG
3951 CCCCAGACTG CATCCACCCA AATCAGAAAT TCCACTCCCA GCTGGCCAGA
4001 GCCCTTTGGA CCAATATGGT AAAATAAGTG GGGTGTTCCT TGTTCTCTGG
4051 GGTTCTAGTC TAGGGCAGGG CACCAGCCCC TATAGAATGG AGTCTTGCAA
4101 GTGAGGCTGA GGGGGCAGTG GCTGGTACAT CTATAAACGT CTATGCAGTT
4151 GGAAATGCGG AGTCCTTAAG AGTCTGCTCA GCCTGGGCTC AACTGCACCC
4201 TCTCCTCAGA GCTTTGAACT CTGAGGAGGG ACCTCTCTAC AGAAATGCAA
4251 GCCCAAAACC CCATATTCAT TCCACTTTCC CTATGTGCCG GCCACCATGT
4301 TAGGCAGTTT AAGCCACGTT ATCTCATTTA AGGCTCTGCA TATCCCTGCT
4351 AGAGAAGCAT GACGAGTCTC CAAGGAAGCT ACTCCCAGAG AAGCAAAGCG
4401 ACTGGCCCAA AACCCCACGG CTGGCAACTG GCAGAGCCAG AAGTGGGAGC
4451 CAAGCCCCCT GAAATCGAGT TCTGAGCTTT CCCCACTGCA GGATTCTGCC
4501 AGGGAATGTT CACTTCCATG GAAACAAACT ACTACACCCG TGTCTCTCTT
4551 TTCTTCCCTG ATCAGCTTGA ACCACTTGGA AGCAAAACAG AGACCCTGGA
4601 CCTGAGAGCA GAGATGCCCA TCACCTGTCC CACTCAGGTA GTAGGGGAGG
4651 ACCTGCCTGG CTCCTCTCCA CAAACCAGGG CACACAGCTC GCCCTACCCA
4701 CTTCGTCCTC CACCACAGCT TCCTCAGTAC CCATCTTGCC CCCTTACTGA
4751 GGCCTGAGAG ATTTGGAGGA TGGAGGGGAG TCCATGAGGA TGGACAGGGG
4801 AGGTGAGAGG GGAGACAAGA GTGCAGCTGT CATTGGGAAC AGGAGATGCA
4851 GCAGGGAGAG GAGGCCTGGG CCCCAGCAGA GGGAGAGGAT CCCGGTGAGA
4901 AAAGTGGGCT CCTGAGAGAG GAAATCAGGA TGCCAGGAAA ATGGCAGGAG
4951 GGCTTCTCTT AGCAGTGGTG TTTGGGGCAG ATGAAAAAAT CTGACTGCAG
5001 GTTAGAGGGC CCAGGCAGGA GCCAGGCAGG CTTAAGAGCT GTGGTTGGAG
5051 AGAGGAGAGC CTGGATTAGG GAGATTCCAC AAGGAAAGGA TCACAGAGGA
5101 CAGCAGCAAA GGGCAGAGCC CAGAGCTGTA TGGAGGAGGG ACGAGGGTGG
5151 GCCTACCAGG ACACGGCAGC TCCAGGCTCC TTTTAAGGAG GAATCCGTAA
5201 GTGGTTGTTA AGCTTGACTT CAGGCCTGGG GTGGGGGCAG GTTCTCATTG
5251 TCTTCAGCTC CTGTTTCTAG GCCCGGTCTT ATGGCTTTTT AACCAAATAA
5301 GGCCAAGGCC AGAAAACCCT CAGCAGCAAT AAAAGCAGAA GGCCTGACCC
5351 AATCTGGGAG GCTGGGTTTC CCTCCTAGGT CGGCCACACC ACCCTCTCCC
5401 ACCCTCCCTG CTGGGGAATG GACCTGCAGC TCCCCCATGT GTCTGCTCCC
5451 AATCCTGAGA GAGTGGGCAC CCCTGTTCAC ATGCCTGCTC CCTGTCTGCT
5501 GCCTGCCCTA CCCCAGTCTT GGGCTCAGGC TCAGTCTTGT GTGCCATCAG
5551 CCCCATCAGG AGAGCAAGAA TGGCAGGAAG AAGGGATGGG AAGTGAAGAC
5601 AGTCGTAGCA GAGGGCTCAG TTGCTGGGTC TTGTGCTTGG AGCTAAGGAG
5651 ATTGTCAGAT TCTGCAACAG CTAGTGCAAC ACAGATGCCT CTAGTCCAGG
5701 TGGTCAGGTG CTGGCCAAAG GCCTGGAGCA AAACCTTAGA GGCCCCTACT
5751 GTGCCAGGTG TAAACTCTTT AACTGCTTTC CTAAGGATGC CTTGGGGGTT
5801 CTAGGGAGC AGCCAGGGAC CGTGGATAGT GGGGGCATTT GGGGACTCAG
5851 AAATAGCCAT ATTGTAGATA TTTCAATATT TTACCAACCC TATAGCCATA
5901 CTGAATATCA GCCATGGAGG GCCCTTTCCA AACTGTCCAC TCCCCTTCCA
5951 TTACATAACA AAAGCAGCCA TCATTTGCTC TTTCTTTCAA CAAACGTGTA
6001 TTGAGTACTG AGTTGGAGCC TAAGCACTGG GTCAGGGAGA GCCCTGTCAC
6051 CCTGGGCTTC GAGGCAACCA CTTCCAGGCT TTACCCCAGA TCAGGCAGAG
6101 ACCCCCAAAA GGAGGCTGCT CCACCCAGCA GCATCTTAAG CTGAGTGGGC
6151 TCAGTGCCTC CCTTCTAGAC AGAGCCCAAT GGAGCCACTG CACTGATTTG
6201 CAGAGGTGAG CAGATCCAGC CTCGTGGAAC CAGTAGAAGC CCAGCCCTGG
6251 TGAAGCTGTT GCTAAGCAAC ATTGGAGCCC ATTCTGAAAG GGTCCATCTG
```

FIGURE 3, page 2 of 33

```
6301 TTGGCCAGCC CAACTTCACT GTGTTCTGAG CATTCTGCAT TCCTCAGTCC
6351 CATCTGCTCC CTCCCATGTG CCTTGGAGTG ATATAAAAGT CCACCAGCAT
6401 CTCAGTGTGA GCTGACAGGG GCCAGGCAGC ACCTATTTTT GTCCTAGATG
6451 TGTCTAAACA TAGAGGCAAC AGGCAACAGG CAAGACGCAG TGGGGGGCGG
6501 GAGGCAGGAG GCCGAGATGG CTGTGAGCAT GAGCTTTCTC AGCCTCCTCC
6551 CTTCTCCCAT CCGCAGTCTA ACTGCTCATA CGTTCTGTGT GCCAGGTAGG
6601 GTGACTTAAC AGCACGCCAT GGATTTCTGT TGTAGTTTCA AGTTGGACAA
6651 ATTCTTTTAC AGACAACTTT TGACTAGCCT TCTGTGGACT GAGCCTATAC
6701 TCTGCCTTAA TGGGCTCTCT GCCCACTCCT TTCCTAACCC CAGGGCAGCT
6751 GGCTGAACAC CTGGTCCTTT TCTTAGGTTT CATTCTTTTT GACCTCTCTG
6801 AAGCCCTTGT CAAAAGTCAC CACCTCCCCC TTGAAATTCA CTCCTTCCTG
6851 GGTTTGTGGA CACTAAATCG CCTTGATTTT TCTGGTCTTC TGTTTGCTTG
6901 CCTTTAATGA CCCTCCTCCT CCCTTTCCCC AGTCTTGAAA ATGTAGATAT
6951 TCTCCAATTT TCATGTCTCC ATTCTATTTT CTTTCCTTTT TCACTCACTT
7001 TTTGAAACAG GGTCTTGCTC CGTCTCCCAG GCTGGAAGTG CAGTGGCGCA
7051 ATCACAGCTC TCTGCAGCTT TCAACTCCTA GGCTCAAGCC ATCCTCCCAC
7101 CTCAGCTTCC TGAGTAGTTG GGACTGCAGG CATGCACCAC CATGCCCAGC
7151 TAATTTTGGT TTATTTGTTT TGGTAGAGGG GGGGTCTTGC CATTTTGGCT
7201 CAGGCTGATT TTGAACTCTG GNNNNNNNNN NNNNNNNNNN NNNNNNNNNN
7251 NNNNNNNNNN NNNNNNNNNN NNNNNNNNNN NNNNNNNNNN NNNNNNNNNN
7301 NNNNNNNNNN NNNNNNNNNN NNNNNNNNNN NNNNNNNNNN NNNNNNNNNN
7351 NNNNNNNNNN NNNNNNNNNN NNNNNNNNNN NNNNNNNNNN NNNNNNNNNN
7401 NNNNNNNNNN NNNNNNNNNN NNNNNNNNNN NNNNNNNNNN NNNNNNNNNN
7451 NNNNNNNNNN NNNNNNNNNN NNNNNNNNNN NNNNNNNNNN NNNNNNNNNN
7501 NNNNNNNNNN NNNNNNNNNN NNNNNNNNNN NNNNNNNNNN NNNNNNNNNN
7551 NNNNNNNNNN NNNNNNNNNN NNNNNNNNNN NNNNNNNNNN NNNNNNNNNN
7601 NNNNNNNNNN NNNNNNNNNN NNNNNNNNNN NNNNNNNNNN NNNNNNNNNN
7651 NNNNNNNNNN NNNNNNNNNN NNNNNNNNNN NNNNNNNNNN NNNNNNNNNN
7701 NNNNNNNNNN NNNNNNNNNN NNNNNNNNNN NNNNNNNNNN NNNNNNNNNN
7751 NNNNNNNNNN NNNNNNNNNN NNNNNNNNNN NNNNNNNNNN NNNNNNNNNN
7801 NNNNNNNNNN NNNNNNNNNN NNNNNNNNNN NNNNNNNNNN NNNNNNNNNN
7851 NNNNNNNNNN NNNNNNNNNN NNNNNNNNNN NNNNNNNNNN NNNNNNNNNN
7901 NNNNNNNNNN NNNNNNNNNN NNNNNNNNNN NNNNNNNNNN NNNNNNNNNN
7951 NNNNNNNNNN NNNNNNNNNN NNNNNNNNNN NNNNNNNNNN NNNNNNNNNN
8001 NNNNNNNNNN NNNNNNNNNN NNNNNNNNNN NNNNNNNNNN NNNNNNNNNN
8051 NNNNNNNNNN NNNNNNNNNN NNNNNNNNNN NNNNNNNNNN NNNNNNNNNN
8101 NNNNNNNNNN NNNNNNNNNN NNNNNNNNNN NNNNNNNNNN NNNNNNNNNN
8151 NNNNNNNNNN NNNNNNNNNN NNNNNNNNNN NNNNNNNNNN NNNNNNNNNN
8201 NNNNNNNNNN NNNNNNNNNN NNNNNNNNNN NNNNNNNNNN NNNNNNNNNN
8251 NNNNNNNNNN NNNNNNNNNN NNNNNNNNNN NNNNNNNNNN NNNNNNNNNN
8301 NNNNNNNNNN NNNNNNNNNN NNNNNNNNNN NNNNNNNNNN NNNNNNNNNN
8351 NNNNNNNNNN NNNNNNNNNN NNNNNNNNNN NNNNNNNNNN NNNNNNNNNN
8401 NNNNNNNNNN NNNNNNNNNN NNNNNNNNNN NNNNNNNNNN NNNNNNNNNN
8451 NNNNNNNNNN NNNNNNNNNN NNNNNNNNNN NNNNNNNNNN NNNNNNNNNN
8501 NNNNNNNNNN NNNNNNNNNN NNNNNNNNNN NNNNNNNNNN NNNNNNNNNN
8551 NNNNNNNNNN NNNNNNNNNN NNNNNNNNNN NNNNNNNNNN NNNNNNNNNN
8601 NNNNNNNNNN NNNNNNNNNN NNNNNNNNNN NNNNNNNNNN NNNNNNNNNN
8651 NNNNNNNNNN NNNNNNNNNN NNNNNNNNNN NNNNNNNNNN NNNNNNNNNN
8701 NNNNNNNNNN NNNNNNNNNN NNNNNNNNNN NNNNNNNNNN NNNNNNNNNN
8751 NNNNNNNNNN NNNNNNNNNN NNNNNNNNNN NNNNNNNNNN NNNNNNNNNN
8801 NNNNNNNNNN NNNNNNNNNN NNNNNNNNNN NNNNNNNNNN NNNNNNNNNN
8851 NNNNNNNNNN NNNNNNNNNN NNNNNNNNNN NNNNNNNNNN NNNNNNNNNN
8901 NNNNNNNNNN NNNNNNNNNN NNNNNNNNNN NNNNNNNNNN NNNNNNNNNN
8951 NNNNNNNNNN NNNNNNNNNN NNNNNNNNNN NNNNNNNNNN NNNNNNNNNN
9001 NNNNNNNNNN NNNNNNNNNN NNNNNNNNNN NNNNNNNNNN NNNNNNNNNN
9051 NNNNNNNNNN NNNNNNNNNN NNNNNNNNNN NNNNNNNNNN NNNNNNNNNN
9101 NNNNNNNNNN NNNNNNNNNN NNNNNNNNNN NNNNNNNNNN NNNNNNNNNN
9151 NNNNNNNNNN NNNNNNNNNN NNNNNNNNNN NNNNNNNNNN NNNNNNNNNN
9201 NNNNNNNNNN NNNNNNNNNN NNNNNNNNNN NNNNNNNNNN NNNNNNNNNN
9251 NNNNNNNNNN NNNNNNNNNN NNNNNNNNNN NNNNNNNNNN NNNNNNNNNN
9301 NNNNNNNNNN NNNNNNNNNN NNNNNNNNNN NNNNNNNNNN NNNNNNNNNN
9351 NNNNNNNNNN NNNNNNNNNN NNNNNNNNNN NNNNNNNNNN NNNNNNNNNN
9401 NNNNNNNNNN NNNNNNNNNN NNNNNNNNNN NNNNNNNNNN NNNNNNNNNN
```

FIGURE 3, page 3 of 33

```
 9451 NNNNNNNNNN NNNNNNNNNN NNNNNNNNNN NNNNNNNNNN NNNNNNNNNN
 9501 NNNNNNNNNN NNNNNNNNNN NNNNNNNNNN NNNNNNNNNN NNNNNNNNNN
 9551 NNNNNNNNNN NNNNNNNNNN NNNNCAATAA ACCCAGCTAA AAACAAGCCC
 9601 AATAAAACCC AATAAAACCC ATTAGACAGG AACATAGGAG TTGGAAAAAA
 9651 AAGAAAAGAA GGGGAGGGGG AAGAAAGCCC TGAGGCACCC CGGCTGCCTG
 9701 TCTGCCACAA CCCTGGGCTG TAATTGTTCT TGCCATGGCC TCAGTCTGCA
 9751 ACACATTCTA GTGTCTCCTT GACCTCTAGC CCTCTAGCTC TGCCTCCCTT
 9801 TCCCCAACCT GTAGATCTTG TGATCAAATA GATTCAATGA AACACATTGT
 9851 CCAGTTGCAC TCGCAGCACT TCCAAAAAGG TCAAGTTTGT CCTTCCCTCA
 9901 GTGCCTCCCA TTCTGGTCAC GGTAGGACTG ACTCCAGCCC CTGGACCCTA
 9951 AGCTGAGTCT GGGCTCCTTT GACGTGCAGG GAGAATGCCA CTGAGTCTTG
10001 TCTCTGAGGA CCCTACCTCT CCAAATCTTG CCTCAGTTCC TCAGCAGGTA
10051 CTACACTGAC TGGCCATGCC ATTCTCTGAT GCTTCACTGC CTCAGCTTCT
10101 CAAGTCTGTC TCCCCACCTG AGCCAATTGT GAGTTTCTCT CTCTCCTCCT
10151 CTCATCCTGG CACCTAGAAA TGCTCTCTAA CGCTTGAGCT GCTCAACCAG
10201 CATGGGTCAC TTGTTTATAG CATGCTCCCA GATCGCCCTC TTTGTTGGTG
10251 AATGCTCAGG GAATGCTTAC TGTTAACCCG AGACAAGCCC AAGTAGCTAC
10301 ATGGACCTGC CACCATAAGC CCTCTCCTGT CTTATGCTGT TGTAGAGGGT
10351 CCAGGGCTCA CTTCTCCCAC TTGGCCCTGA GTACCTCTCC TTGAAAGGAT
10401 GTCAGGGGCT GGGCGCAGTG GCTCACGTCT GTAACCCCAG CACTTTGGGA
10451 GGCTGAGGCG GCGGATCAC CAGGTCAGGA GATCGAGACC ATCCTGGCTA
10501 ACATGGTGAA CCCCCGTCT CTACTAAAAA TACAAAAAAT AAAAATAGCC
10551 ATTTGTGGTG GCAGGTGCCT GTAGTCCCAG CTACTCGGGA GGCTGAGGCA
10601 GGAAAATGGC ATGAACCCAG AAGGCAGAGC TTGCAGTGAG CCGAGATCGC
10651 GCCACTGCAC TCCAGCCTGG GCAACAGAGC AAGACTCCGT CTCAAAAAAG
10701 CAAGCAAGAA AGAAAGGATA TCGGTTACCT GTTTCAGACA GGAATGCTGA
10751 GACCAGGGAA AGGGGAGACT TGTCGGGTGC CTCAGGGAAC CAGTATCTGA
10801 GCTGGGGGCT GAGAGCTCTG TGTGGGTGGA CTCTGTCCTC CCAGTCGCTG
10851 CTGAGTCCCT CTCTTCCTTT CCCGCTGTCT GACCAACAGG GTTTTGTTG
10901 GCCTGACCTC CAGTGTGAGG AACGGAACCA GGCAAGAGGC TTGTCCAGTC
10951 AGCTCTGGCC CCAGTTTGGC ATTCATCACT TGTTCCCTAA CCTGGAACCC
11001 GTCCCTTCCT CACTCTGGGG CTCAGCAGCT GCTCATCTAT AAAGTGGGGC
11051 ATTTGGGGGT TGCAAAGTCA GTCATCTACA ATGCCAGGCA AGAACATGGT
11101 TGCGTACATG TGGTCAGGTA TGAGACGAGA TCACTTTTCC AACATTCTGG
11151 TTTTCCCTTT TTTTTTTTT TTTGAAACAG AGTCTTGCTC TGTTACCCAG
11201 ACTGGAGTGA ACTGGCATGA TCTCATCTTA CTGCAACCCC TGCCTCCCAG
11251 GTTCAAACAA TTCTCATGCC TCAACCTCTC AAGTAGCTGA GATTACAGAT
11301 GTGTACCACA CCTGGATTTT TTTTTTTTT TTTTTGTAT TTTTAGTAGA
11351 GACAGGGTTT CACCATGTTG TCCAGGCTGG TCTTGAACTC TTGGCCTCAT
11401 GTGATGAACC CCCCCTTGGC CTCCAAAGT GCTGGGGTTA CAGGTGTGAG
11451 CCACTGTGCC CAGACTAATT TTTTTTTTT TATTGAAACA GAGTCTCACT
11501 CTGTTGCCCA GGCTGGAGTG CACTGGCACA ATTATAGCTC ACTGTAACCA
11551 CAAACTCCTG GGTTCAAGCA ATCCTTCTGC TTCAGCCTCT TGAGTAGCTA
11601 GGATTACAGG CACATGCCAC CATGTTGAGC TAATTTATTT TTTTAATTTG
11651 TCGTAGAGAT GGGGTCTTGC TATGCTTCCC AAGCTGGTAT TAAACTCTTG
11701 GCCCCAAGCA ATCCTCCTAC CCTGGCCTCC CAAACGCTG GGAATACAGG
11751 CATGGGCCAC TGTGCCAGCC TGGTTTTTTC TTCTTGTTCC CATTTTATTC
11801 TCACATTTTC AGACCATGGG CTTACTACTC CACTGAGCAC ATTTTGTGAG
11851 AGTGCTCACA GCCCTGGGCC CGGTTGCTGT TTCCTGATCT CAGTCTTATC
11901 AACTTGATCT TGCTTTGCTG TCATTTATAC ATTTTCTCAT TAGCTTTCTC
11951 CCCATTTCTT CTTTGTCTGC TTCCTTCTTC CTTCTTTAAC TAACTCCTCA
12001 CCTGCAACTG GGGGACTTG GATTCTTGAC TGGGCTTGTG TGAAAACTGA
12051 TTGTAAAACA GATAGGTAAG TAGGGAATGA GGAGGGTGTT TTACAAGAAA
12101 AAAAAAATGA CTAAGATACA GGAACCCAAC CTAAAGAGGA AAAGACATAC
12151 AGTTCAAAGG AGGCAGAAAG AAAAACATTA CAGATACTCA AATATATTGA
12201 TAATCATAAC ACTTTCTGGA AGATTAAAAA AATGCTGAAA CATGAATCCC
12251 TTGCTAGAGA AATTACAAAG CCAAGAAAAT AGATAGGTCT GAGGATTAGG
12301 GAGCTGTTCA GTTGCTAGGA GGAACACAAA AGCACAGACC CCAGACTACA
12351 ATGGGTATGA AACCCTCTGC ACGCCTTTTG TTGTCCATCC CTTGCCAAAG
12401 CTGTTATGTA AAACCCTCCG GGGGAATGAA TGAAATTATG TTTATACAGT
12451 TCTTTCTATA TAAGTGCAGA AGAATCATGT TAAATAAATC TACAGGGCAG
12501 GATTGTTAGT TTTTCTCCTT CTCAAGCAAA CTTCAGTGCT GTCAGATAAC
12551 TTCTCCATGT GTTTTTTTTT TCTCTTAGAA TGAGCCCTTC CTGAGAACCC
```

FIGURE 3, page 4 of 33

```
12601 CTCGGAATAG TAACTACACG TACCCCATCA AGCCAGCCAT TGAGGTAACC
12651 CCTGACTCAC ATCTGCCTCT CTCAGACACA AACCATTTCC ACCTGCCAGG
12701 GGCTCGGGTG TGGTACAGGT TTCAGAGTAT TCACTGAAGC AGAAATGTAC
12751 TTCTTACATA CTGGGGATTG GAATGTACAG AAAAGGCTCC CGGACCACGA
12801 AGCCCCAGGA TTGTCCTAAC ATCTTCTCAA GTTGCTTACC TGACGTCAGC
12851 CCCCAAGCAG AGGAAGTGTC TATGGATCGA TTTTCTTTGA CCTTGGCAAT
12901 CCTGGGCTCA CAGACGTGGT TACTGCTTAG GCAGCTCAGC CTCTCAAGAG
12951 GGAGAGGCAG CTGGTGTGAT GTGGCGTTGA CTTCTTGGAA GGTGGAGGCT
13001 GAGTGGGAGG GAACTACAAT TCTGGGGATG GGACCCAAAA GGAAGTGGAG
13051 GCACGTTGTT CATGTTCCTG TGGCCCCTA GGCCTTGTTT GGTTCAAGTC
13101 AATCATTCTA GTGCTGAGGA TTCAGAGCCC ATGGTTAATT CCATTGGATT
13151 AACCATGTCT GTGAGCCTAG GACGGCCACT GCAAAGACGG CCTGGAGGAC
13201 CCCGGACTAT ACCATGACTG GCAGTCAGGC CTGGTCCGGA TCAGGTCTGT
13251 TGGTCACCAG GATGGGGTTT GACCCGCAGT TTCAGTTTCA CACCTATATT
13301 ATATCCAGTC TCATGTTAGG GGCTAGAAGG CATGCAGAGA AGTATCGAAC
13351 ATGGTCCGGA CCAAGGGAAG TGAGAGCCCA GTAGAATTTC ACAATTATTG
13401 AGCACATACT ATGTGCCAGA CACTATTCCA GGAAGACAGA AATGTTAACC
13451 AGACAGATGG ATCCCGGCCC TCACGTAGCT TACAATCTAC TGAGAAAGGT
13501 GTCTTATATA CATGGCTAGG CATGGTCATT TCAGATAGTG ATGACAGCTC
13551 TGAGGAGCGT GATGGGGCTG GGCAAGGGA GGCAAATTCA GGTGCACCAT
13601 GCAGGCCAGG CCTTCCTGAG GTGAGATTTA AACTGAGACA TGCATAATGA
13651 GGAGACACTT GCTATACAGG GAGCCAGGAA CACAGTCCCA GGCAGAAGGA
13701 CCATGGACCA CACAGGCTCA GAAGTGGGAC TGTGTTGGGT GTATTTGGGG
13751 AAGAGAAAGA AGGTCAGAGT GGCTGGGGGC ATGAGAATGA GGTGGAGAGT
13801 GGGGAAATG AGATCAGGAG TGCCAAGGAG CCAGATCACA CAAAGCCTGA
13851 ATTACTGAGT AAAACCACTG GATTTCAAGT GGAGAAAGAT GGGAAGGCAT
13901 TGGCGGTCTC AGGAGAGAGT GACATGATCT GGTTCACGTC TTTCAAAGAT
13951 CTCCCTGACT GCTATGTGTA GAATGGGTTG GCCATCAGCA GGAGTGATTG
14001 GGGAAAGACA TTTTATAAGC CAGCTGAAGA AACTAACCCA TATGAAATCA
14051 TTAAGAACTA TTGGATGCTA AGCTCTGGGG TGCAAGCAAT ACCAGATTGC
14101 TGGCTGCGGG TTATGCTGTG TCCAGCCTCT CTGAATTTTC TCAGGCTCAC
14151 GTTAGCCCAG TGGAGGCTTG TCCTCATTGA ACCAGTGACC AAATTCCCTG
14201 AGAATTGAAA CGTCAGCTGC ATCTTGTGAA TCAGGCATTT CTTCATTTAT
14251 TCATTTACCT ATTGGATGCC TATGTAGAGT GGGCACTGCA CTAAGTGCTC
14301 GGTAGACAGT GGTGAGCCGA ATGGGTCTGG ATCTGCCCTC TTGGTTCTTC
14351 AGTCTCATGC ATCTTTGCTT TTGCTGCTGG AAGAGCTAAA AATCCCAGAG
14401 CTAGAAGGGC GTGTGTTTGT TTTAACAGCT TTCTACTCAA AGTAACCACA
14451 GAAACAAAAT TCTGTCATCT GAGGTAACGT GAATGAGCCT AGAGGACATT
14501 ACGTTAAGTG AAATAAGTCA GGCACAGAAA GACAAATACT ACATGTTCTC
14551 ACCATATGCG GAAGCTTAAG AAGTTGACTT CACAGAAGTA GAGTATAAAT
14601 AGTGGTTATT AGAGGCTGGG AAGGGTGGAT GGTGGTTGGG GAGTAGAGAT
14651 AGCAGAAATT GATTAACAGA AAATTACAGC TATATAGGAA GGAGAATTTC
14701 TAGTGTTTTA TAGCACAGTA GGGTGACTAT AGTTAACAGT TTACCATATA
14751 TTTTCAAATA GCTAGAACAG CAGATTTTGA ATGTTCCCAA CACAAAGAAA
14801 TGGTAAATAT TTGAAGTGAG GGATAGGCTA ATTACCCTGA TTTGATCACT
14851 GCACATTGTA GAGATGTATC AAAATATCAC ACTATGCCTC ATAAGTATGT
14901 ACACTTAATA TGTCAATTAA AAATAATAAA AGCAAAACTA ATAAAGTGGC
14951 CACAAAGAGG CTTTACCTGG GAGCTTTTTA GAAATGCAGA GTCCTGGGCA
15001 CCACCCCAAA CCTGCTGAAT CAGAATCTGC AGCTTAAGAT CTTCAGGGGA
15051 TTTGGATGCA CTGATTTTGG GTGTGGTGCA TGGTTCTTCC CTTGTGACGG
15101 ATGAGCACGT TCAATTCCA ACCAGGATCT GTTAATCTAC ATGGAATATG
15151 CTTATCTCTG GTTCACCAAC TATCTGAGAT ATATCTCATG TGCTGATGGC
15201 TGAATAACTT TTTACGTTGC ATTTTCTGTG AGTATTTGTC ATCTGCACAC
15251 AAGCATGCTC TTGAGTTCAT TAAACCTTTA AACAGAAGAA ATCCATCAGA
15301 ATGATGAATT GAGCAATCCC TTGGGAAAAA ACCAAATTCC ATAGGATTAA
15351 GCAAATAATA TTTAAAAGAA GTTCCATTTT TGCTCTCTCA TGATAGGAAT
15401 ATTTCAACAA GTCTTATCTT CATCATCTGA CTGAACAGAT GAGATGAGTT
15451 TTCATAGCAT CTGGCAGTCA GACTCCTGGA CAGTCAATCT GCTGGTCAAG
15501 CCCTACTCCA TACTCAGTAT GCATATATTT GAGACTTTGG GAAGATACTC
15551 AATTTTCCCC CAGATTTCTG GTACTAATCA TTTCTATGCC CTCTGCTTCC
15601 CATCCCACTC CTTTCCCCAG CACCTGGAAA ATATGTTCTG TATTAGAGAC
15651 AAAGAAAATT GACTAAAAGC ATCCAGGGTT GCTTACATCA ATTTAAAAAC
15701 ATATAAGGAA TAAGGCTGTT AAGTTAAATA TGCAAAAAGA CATACAGGTA
```

FIGURE 3, page 5 of 33

```
15751 TCCAGAAAAG ACAGGCAGAA ACCAGGAGCT TTACAATTTT AAAATATTTT
15801 GTGTTATTAT TCTAAAAATA TTTTAATTAT TGTCTAGGTT CTACCATTAT
15851 AATTAGTGTC AGTTAGCTTA ATTTTATAAA ACACACATAC CTGTAATCTC
15901 ATGTTAGGCA TCCAAATGCT GTGTTCCTTT GGGAGACCCA CCTGTGTAGG
15951 ACTTCATGGT TTTCTTCCCT GCTTTGGGGC AGCCACTGGC TCCATTCAAA
16001 GCATAGATAT ATGGGGATAA GAAAGGTTGT GTGTGGGTGC ACATGTGGAG
16051 ACATGCACTA TGGGTTGTGC ATAGGGGTAG CTAGACACAC CCATTTCTCC
16101 CCCTTTAATT TCCCTCCTAG CCCACCTATA ACTCACAGTT CTTTCCCTCA
16151 CATGATCCTG TATGGTGACT CATTTCTAGC CTCCATCAAA AATCCCTTAG
16201 CTGGTTCTTC TTGGGCTGAA GCTTATCTCC CTGCACAATG AGTGTTGGGC
16251 ACTGAATCTT TTCTCCTGTT GATTTAGAAC TGGGGCAGTG ACTTCCTGTG
16301 TACAGAGTGG AAGGCTTCCA ATAGTGTTCC AACCTCTGGT GAGTGAAAAC
16351 ATCATCATCT CCTTCAATTA AGGGCCTTGC CGAATATCAG GTTGTGGGGA
16401 GACCCTGCAA ACATACCCTG GAGCTTTAAG CAGGACTTGC TAATTCCCCT
16451 GCAGTGCAGA CCTAGATCCT GCGGCCTGCC GCCACAGCTG GGCTTCCATG
16501 TGGAGGTGCA CAGAGCTCTC CATTGGATGC TACTTCTTGT CTCCTTATAG
16551 TCCCAGTGGC AGTCCCTTAG GCCTCCCTGC CCAGTGAGGC AGGTAGAGTC
16601 AGGGATTGGG ATCTACCTGC CTGTGCTACA TGACCCTGCA GCTGGAACTT
16651 TCCTGGACCA CCCCAATGTC AATCAGGCTC TTCTGAGGGT GGATGATAGC
16701 CATGAAACCC ATTCCCTGCA GTGCCTTGGT TGGTCTGAAT GAATGGGAGG
16751 GGCAAAACTG CTAAAGCCTT AAGCTGAAAA TAAGTACAAT GGGGAGCAGT
16801 GGGACAGAGT TATAGACTTC TGGTAAAATG TGTACTTTAA GAGGTAGATA
16851 CCCCCAGCCC CCACAACCAC CTCTCTGCTT GTCTCCCCTA GTCCACCAGC
16901 TCCGACCAGC AGACATCAAA GTGGTGGCCG CCCTGGGTGA CTCTCTGACT
16951 GTGAGTAGTG AGCCATGAAC CAGGATGGGC AGCTCAGAGT CCAGCCAGGC
17001 CCTGCGCAGA ATCTGTGCTT CCCCAGCATT GGCTCCGCTT TCAGTGCTGA
17051 GCCCGTGTTA CTGAGGGCCT ACCCATGTCA GGCACTGAAA CACAGCCAGG
17101 AGATGTAGAA TGCCCTGTCT CGCCACCTTC CCAGTTCTGC TCAAAGCCCC
17151 CTCGTCCATG AGGCCTCCCC TCAATTCCCC AGGGAGAAGC AATCCCCGCC
17201 TTCCCCACTG TTCACAGGCG TTTTGTTGGT GTGTGATGGC ACTCATTCAA
17251 GTCTGCCTGC CTTCATCAGG GGACTCATCT CCATCTACCC AGACTCAGAG
17301 TGGCAGGTCT TACACACACA CTGCCCCATG CTCCCTACTC CATTTAAGGA
17351 CATGTGCTTT GGGGCAGAGG GAGCCCGGTT CCTCACACAT AGCACAGTCT
17401 TGCTAAGTGA ATTGTGTTCG CCAATTACTT AGCCATTGTT GTGTACACCA
17451 ACACTCTATT AGCAATTCTA AGGGAAATGA GGTATGAAAC ACAGTCATAG
17501 CCCCCCAGCA ACCTGTCTGG CTGGAAAAAC AAGAAACGTA CACAGAAAGA
17551 AATGCATAGT CACATAGATG ACATATAGGA CTTGGATGTT TTATTTTTAT
17601 TTTTTAACTT CTAAGTTCAG GGGTACATGT GCAGGTTTGT TACACAGGTA
17651 AACTTGTGGC ATGGNNNNNN NNNNNNNNNN NNNNNNNNNN NNNNNNNNNN
17701 NNNNNNNNNN NNNNNNNNNN NNNNNNNNNN NNNNNNNNNN NNNNNNNNNN
17751 NNNNNNNNNN NNNNNNNNNN NNNNNNNNNN NNNNNNNNNN NNNNNNNNNN
17801 NNNNNNNNNN NNNNNNNNNN NNNNNNNNNN NNNNNNNNNN NNNNNNNNNN
17851 NNNNNNNNNN NNNNNNNNNN NNNNNNNNNN NNNNNNNNNN NNNNNNNNNN
17901 NNNNNNNNNN NNNNNNNNNN NNNNNNNNNN NNNNNNNNNN NNNNNNNNNN
17951 NNNNNNNNNN NNNNNNNNNN NNNNNNNNNN NNNNNNNNNN NNNNNNNNNN
18001 NNNNNNNNNN NNNNNNNNNN NNNNNNNNNN NNNNNNNNNN NNNNNNNNNN
18051 NNNNNNNNNN NNNNNNNNNN NNNNNNNNNN NNNNNNNNNN NNNNNNNNNN
18101 NNNNNNNNNN NNNNNNNNNN NNNNNNNNNN NNNNNNNNNN NNNNNNNNNN
18151 NNNNNNNNNN NNNNNNNNNN NNNNNNNNNN NNNNNNNNNN NNNNNNNNNN
18201 NNNNNNNNNN NNNNNNNNNN NNNNNNNNNN NNNNNNNNNN NNNNNNNNNN
18251 NNNNNNNNNN NNNNNNNNNN NNNNNNNNNN NNNNNNNNNN NNNNNNNNNN
18301 NNNNNNNNNN NNNNNNNNNN NNNNNNNNNN NNNNNNNNNN NNNNNNNNNN
18351 NNNNNNNNNN NNNNNNNNNN NNNNNNNNNN NNNNNNNNNN NNNNNNNNNN
18401 NNNNNNNNNN NNNNNNNNNN NNNNNNNNNN NNNNNNNNNN NNNNNNNNNN
18451 NNNNNNNNNN NNNNNNNNNN NNNNNNNNNN NNNNNNNNNN NNNNNNNNNN
18501 NNNNNNNNNN NNNNNNNNNN NNNNNNNNNN NNNNNNNNNN NNNNNNNNNN
18551 NNNNNNNNNN NNNNNNNNNN NNNNNNNNNN NNNNNNNNNN NNNNNNNNNN
18601 NNNNNNNNNN NNNNNNNNNN NNNNNNNNNN NNNNNNNNNN NNNNNNNNNN
18651 NNNNNNNNNN NNNNNNNNNN NNNNNNNNNN NNNNNNNNNN NNNNNNNNNN
18701 NNNNNNNNNN NNNNNNNNNN NNNNNNNNNN NNNNNNNNNN NNNNNNNNNN
18751 NNNNNNNNNN NNNNNNNNNN NNNNNNNNNN NNNNNNNNNN NNNNNNNNNN
18801 NNNNNNNNNN NNNNNNNNCT CCAAGTTTAA TATGGCCTGG AGAAAAGCCG
18851 GTACTATTTT TAGAAAAGGC AAATCCAGGT CCTAGCTGCT ACCCCAGGGC
```

FIGURE 3, page 6 of 33

```
18901 CAGAGGAAGG CTCTTCCAGT GCCCTCAGCC TATACCCCAG CCCTGAACTT
18951 TCTTTTTGCT TTTTACAGAC AGCAGTGGGA GCTCGACCAA ACAACTCCAG
19001 TGACCTACCC ACATCTTGGA GGGGACTCTC TTGGAGGTGA GGATGTTCTT
19051 GATGCATGCT CTATTGATGA TGCTCTCTCA GAGAGGTGTG AGTAGTGTGT
19101 TTCCTGTCAC CCCTCCAGGG ATGCAGTTGG GTCCCCAGGT CCCAGCGCTG
19151 AGACAGGAGA CTCAATGCTT GCATTACCCC TGAGGGTGAT GGGAGAGACG
19201 CCCCAGGGGC CCAGAACCCG GTTCCGGTTC TGGCTTGTGC ATATGTTGAC
19251 ACAGGGAGCA GCATGTTGGT GTGAGTTTAA CAAATATGCT TTCTCCTCCC
19301 CAGCATTGGA GGGGATGGGA ACTTGGAGAC TCACACCACA CTGCCCAGTA
19351 AGTAGCAGCC CAGAGAGGCA CCATCACTGT GGCCGTCCTC CCTGGGGCCA
19401 GGGCCTTCCT GCTGGAGGAG GGGAAGAGGA GGTTATCTGC AAGAAGGGAA
19451 GTCAGCCAGC CCTGAAAAGC CCCAGACTTC CTGTGTCCCA CCCATGTCCC
19501 CACCCTGCAT GCTCATCTCA GTTACTGTGA GGGTCCTGCA GGCTCTCACC
19551 TGTGCTCTTC TCCTCCTCCT CCTCCTCTAA AGACATTCTG AAGAAGTTCA
19601 ACCCTTACCT CCTTGGCTTC TCTACCAGCA CCTGGGAGGG GACAGCAGGA
19651 CTAAATGTGG CAGCGGAAGG GGCCAGAGCT AGGTGAGTAG ATGCCGTACA
19701 GGAGGGCGAG NNNNNNNNNN NNNNNNNNNN NNNNNNNNNN NNNNNNNNNN
19751 NNNNNNNNNN NNNNNNNNNN NNNNNNNNNN NNNNNNNNNN NNNNNNNNNN
19801 NNNNNNNNNN NNNNNNNNNN NNNNNNNNNN NNNNNNNNNN NNNNNNNNNN
19851 NNNNNNNNNN NNNNNNNNNN NNNNNNNNNN NNNNNNNNNN NNNNNNNNNN
19901 NNNNNNNNNN NNNNNNNNNN NNNNNNNNNN NNNNNNNNNN NNNNNNNNNN
19951 NNNNNNNNNN NNNNNNNNNN NNNNNNNNNN NNNNNNNNNN NNNNNNNNNN
20001 NNNNNNNNNN NNNNNNNNNN NNNNNNNNNN NNNNNNNNNN NNNNNNNNNN
20051 NNNNNNNNNN NNNNNNNNNN NNNNNNNNNN NNNNNNNNNN NNNNNNNNNN
20101 NNNNNNNNNN NNNNNNNNNN NNNNNNNNNN NNNNNNNNNN NNNNNNNNNN
20151 NNNNNNNNNN NNNNNNNNNN NNNNNNNNNN NNNNNNNNNN NNNNNNNNNN
20201 NNNNNNNNNN NNNNNNNNNN NNNNNNNNNN NNNNNNNNNN NNNNNNNNNN
20251 NNNNNNNNNN NNNNNNNNNN NNNNNNNNNN NNNNNNNNNN NNNNNNNNNN
20301 NNNNNNNNNN NNNNNNNNNN NNNNNNNNNN NNNNNNNNNN NNNNNNNNNN
20351 NNNNNNNNNN NNNNNNNNNN NNNNNNNNNN NNNNNNNNNN NNNNNNNNNN
20401 NNNNNNNNNN NNNNNNNNNN NNNNNNNNNN NNNNNNNNNN NNNNNNNNNN
20451 NNNNNNNNNN NNNNNNNNNN NNNNNNNNNN NNNNNNNNNN NNNNNNNNNN
20501 NNNNNNNNNN NNNNNNNNNN NNNNNNNNNN NNNNNNNNNN NNNNNNNNNN
20551 NNNNNNNNNN NNNNNNNNNN NNNNNNNNNN NNNNNNNNNN NNNNNNNNNN
20601 NNNNNNNNNN NNNNNNNNNN NNNNNNNNNN NNNNNNNNNN NNNNNNNNNN
20651 NNNNNNNNNN NNNNNNNNNN NNNNNNNNNN NNNNNNNNNN NNNNNNNNNN
20701 NNNNNNNNNN NNNNNNNNNN NNNNNNNNNN NNNNNNNNNN NNNNNNNNNN
20751 NNNNNNNNNN NNNNNNNNNN NNNNNNNNNN NNNNNNNNNN NNNNNNNNNN
20801 NNNNNNNNNN NNNNNNNNNN NNNNNNNNNN NNNNNNNNNN NNNNNNNNNN
20851 NNNNNNNNNN NNNNNNNNNN NNNNNNNNNN NNNNNNNNNN NNNNNNNNNN
20901 NNNNNNNNNN NNNNNNNNNN NNNNNNNNNN NNNNNNNNNN NNNNNNNNNN
20951 NNNNNNNNNN NNNAAAATCA AAAATTAGCT GGGTGTGATG GTACACGCCT
21001 GTAATCCCAG CTACTCGGGA GGCTGAGGCA GGAGAATCAC TTGAACCCAG
21051 GAAGTGGAGG CTGCAGTGAG CCAAGATCGT GCCATTGCAC TCCAGCCCGG
21101 ATAACAAGAA TGAATCTCCA TCTCCAAAAA TAATAATAAT TAAAAATAAA
21151 TAAAAGATAC AAAGGAATCA AAAGATGAAC TCCCTGGCCA CGAAGAGCTT
21201 GCACTCTAGG TAAGGAGGCT AAACAAATGG GAAATAACTT TCTGAAAAAG
21251 ACAATGCTGG GTATGGCAAC AATGCAGTGC TTCGCATGGA GTACAATTAA
21301 GAGAACAGAA GAGCACACAG TATGAACTGC ACTGTCTAAA GACAGATGCA
21351 GACCCAGAAG GGACCCCTGA AATCATCCAG TCCAACCTCT TCCTTTAAAA
21401 GATGGGAAAA GTCAATCCTA GCAAGATTCA GCAACTTGTA CAAGCTCAAC
21451 AGCAAGTTGG TAGCAGAGCT GAAAGTAGAA CCACTGGTCC CTGGGGTAAA
21501 AAAGGAAATG CAAGATGTGT GGATCAGGGA GCCCAGAGAG GAGGCTCAAG
21551 GGAAAGTAGG ACTTGGTCTG GGCCTGAAGG ATGGGAAGAA GATGGCTAGG
21601 AAGAGGGGAA GAAGCGGCAT TTGTAACTTC CCCTCCTACC CACGAGGGCT
21651 TATTGCCCAT GGATTCTCTT AGTCACACCT TGAACCTGTT AAAAGGTTAA
21701 AGGCACTTCT GTGGTCACCT TTGACCAGAA AAGTCTTTCT TTATAGCTTT
21751 CTGGTATACT CATCAATAGC AATAATGTAT GGGATACAAT CCTAGATCTG
21801 TAAATTCTCC TTAATGAGAA ACAAGGGTAG GGATGGTACC ATGTGTGTTT
21851 GGCCACGTAC CTAGCTTACC GTGGCCACCC AAAGATTTTC AGTGGCCAGC
21901 TCGCACTGGT TGCTGCTTTT ATGGCTTCTT CCATGGACGC TTTCATTGGC
21951 TATATCCCCT TTGCTGACCT AACTTCTCAC AGACATTTCT TTAAACACAG
22001 CTTTATTGAG GTATAAATGA CATGCAATAA ACGTCACATG TTAAAAGGAT
```

FIGURE 3, page 7 of 33

```
22051 ATAATTTGGC TGGGTGCGGT GGCTCACGCC TCTAATCCCA GCACTTTGGG
22101 AGGCCAAGGT AGGCAGATTG CCCAGGAGTT GGAGACCAGT CTGAGCAACT
22151 TGGTGAAACC CTGTCTCTAC CAAAAATACA AAAAATTAGC CGGGCATGGT
22201 GGCATGGACC TGTAGTCCCA GCTACTCGGA AGGCTGAGAT GGGAGGATCA
22251 CTTGAGCTCA GAGGGGTTGA GGCTGCAGTG AGCCGTGATC ACACCACTAC
22301 ACTCCAGCCT GGGCAACAGA GCAAGACCCT GTCTCAAAAA GGATACAATT
22351 TAACATTGTA CCTGTGAAAT CATCACCACA ATCAAGATGA AAAATGTGTT
22401 TATCACCCAC AGGAGTTTTC TCAGGCCCCT TGGTAATCTC TCCCTCCTGC
22451 TCCTTCCTGT CCCTACCTCA CACCCCAGGC AACCACTAAC CTTCTTTCCA
22501 TCACAATAGA TTAGTTTGCA TTTTTAAAAA TTTTATATAA ATGGGATCAA
22551 AGAGTATATA CTTTTTATCT GACTTATTTA GCAAATGAT TTTGCGATGC
22601 ATCCATGTTA TTCGGTATAC CAATAGTTCG TCCCTTTTTA TGGCTGAGTG
22651 TAGTGTTCCG TTGGCATTCA TATCGTCAT CCAGAACACC AAATGGTATT
22701 GTTTTATTTA TGGCAGACAT CAGGGGATGA AGGGAGAACT AATCCTGTCC
22751 ATCCTGGTTT ATTGGAGAGG GAGAAAAAAA AAAGTGAGGA GATGGGGAAT
22801 GGTGCGGAAA TCTAAGTAAC CACAGAAAAG AAAAACAAAA GGATTAAAGG
22851 AGCAGAGAGC AGGGCTTAGA AGTAAAGGTT AAAGGAGTCA TTAAGCCTGG
22901 AAAGGAGAAA ACTGAGGGAT AATTGTGAGC TGTGACTTTT CTCAAATATA
22951 CAAAAGGTTA TTTTTAAAAC AGGCAACTGA AGAAGAAATG AACAGGCTTG
23001 GCTTACGAAG AAAGAGCTTG AGGAAGTATA AGGGAAAGTC CCTGAGGGGA
23051 GGCTTGACGG GATCCCAACC CGAGTGGCCG ATGAGACTAT TGGGTGGCAG
23101 GGGCTAGATC AATGTGGCTC CAGGGTCCAG GGCAGCCATG TGATTGTTAC
23151 TAAGCTGAGA TTTCTTGAGA ATGGAATGAC CTTTGTACTG GTAACATCAT
23201 TCTTCTTGAA ACACCTCTCT TCCTAGGCCA AAATCCCATG TCGTGAGTCC
23251 TCGCTCCTGA GCCGGCACTA ACGCCCCTCT CTCTACCCCC CACCTAGGGA
23301 CATGCCAGCC CAGGCCTGGG ACCTGGTAGA GCGAATGAAA AACAGCCCCG
23351 TGAGTACAGG CCCCCAGGCC ACCCCTGAAA GGTGCCCATC TCCTGCTGGC
23401 TGGGGAGGGG ACAGCCCCAT AAGGGTCCCT CTCACCACAG CACTTCCTGC
23451 TTTGGGCTAG CCAAAAGATC CTCGGAGAAG CAGTCCTTAC CAAGGAGGCG
23501 CCTGCCCTGG CCACACTCCT AGACGCAGGC TGTGGCACCC CTCACCCCAG
23551 GGCCGGCTGC GGGAGGGCAA GGTGGAACAG GGAGTTGGCT GAGGTGGTGG
23601 CCTTGGCCTC TGACAGCTTC CTGCTTTAAC CAAGAGGTGG CTTCCCAGAG
23651 CCCTATTATG TAAATGCAAG GTTCTAAAAA TAGGCTTCTC ATTCCAATCC
23701 AGTTCTGCCT CCTTCCCCTC ACCCTGCCCC TCTGAAACTT CTCACTAGCA
23751 CTTTTTTTTT TAACCGTTCA GTGTTTATGC CTAGGAATTC AGCTCCGGT
23801 GGGATTCCTA TTATGGAGGT GGCCAAGTGG AAAGCCAACT GCTTAGAGGG
23851 CCTCCCAGCC CCAACCCCGC TTCTCAGTCC ACGCTGGGCT CTTCCTCCAG
23901 TCTCCTTCCC CCGACCCTAA GAACTCATCC CAGGGGCAGC TTAGGGCCTT
23951 TGCTTCTAGC TGCATCCTTT GCCTACAGCT CCCTGGAAGG CCTTCATTTG
24001 GGGGGACGTG GTAATCCCCT CGGCATTTAA TGGGCCAAGG ATATGTGGGA
24051 CACATCCACA TTCTACTTCT CCAGGGACAC AACTTTCTTA AGATTTCAAG
24101 GGGAAAATAG CCCTCCCTTG TGTAAGCAGA ACCCCGTCCC CCGCCAGCGC
24151 CCACCGCCAA AAAAAAAAAA CATCCTCTCT GTGGAGCACC TTATCCTAGC
24201 ACCAATTGAG GGCTGGGAAG CCCCACTTTG TTGCTTTTCT TTTTTTTTT
24251 TTTTTAGACG GAGTCTCGCT CTGTCACCCA GGCTGGAGTG CAGTGGTGCG
24301 ATCTCAGCTC ACTGCAGCAT CTGCCTCCTG GGTTCAAGTG ATTCTCCTGC
24351 CTCAGCCTCC CAAGTAGCTG GGATTACAGG CACCTGCCAC CAGGCCAGGC
24401 TAATTTTTGT ATTTTTAGTG GAGACGGGGT TTCATCATGT TGGCCAGGCT
24451 GGTCTCGAAC TCCTGACCTC AGGTGATCCA CCTGCCTCAG CCTCCCAAAG
24501 TGCTGGGATT ACAGGTGTGA GCCACCGTGC CTGGCCCAAT TTGCTGCTTT
24551 TCTCTGTTAC AGTATAAATA AGACAAAAGG CACTTGGAGG GCGGGCGGGC
24601 TGGCCCAGTA GCAACATTTG TATGTGCCTC CCACCAAGGC CTAAACTCAG
24651 GATCTTCTGT CCCCTCAGGA CATCAACCTG GAGAAAGACT GGAAGCTGGT
24701 CACACTCTTC ATTGGGGTCA ACGACTTGTG TCATTACTGT GAGAATCCGG
24751 TAGGCCCCCG ACCAACCCCA TGGGGACCTG AGAAGGAAGG TGCTGACCTC
24801 TGGCAACACC CTTGCCCATC CATCCCTGGC CCTGCCCCGA GCTCCTCGCT
24851 CATGGGAACC ACATTTGCCT GCTGCCCCAG GCCCTCCCTG GTTTACACAT
24901 GCCAGGCAAG GCCCAGCCTT TTCTACTGCC TGAGCGACCC CTGGAAGAGC
24951 AGGTGCATTG GTTCCCCAAT TCCAGAAGTA AGGCCAAGGT GGACCCACTG
25001 TAGGCACTGC TGAGGTGAGG CCTCTCTTAT CCACACAAAT ATGACCTCTG
25051 GTACCAGATA GGGGACTAGC CATCCTCACC CCATCCCTGC CCTGTTTCAT
25101 TTTGAGGAAG GGCAAAACAA TGTTCTAAAT GGGGTTGGAT GGGTCATCAC
25151 GAGTTAACCA AACCTCAGTG GTGGCCCTGG GAGCCCAAAC CTGTTCCTGA
```

FIGURE 3, page 8 of 33

```
25201 TGTTTCCATG GGGAAATATG TCCAGACTCA CAAACTTCTG GAAGTTGTAA
25251 CTTCCAAAAG TTTTTATTTT GGAATACATC TTGTTCTAAG TTGGGGACAT
25301 TCTGTATTTT ATTTGGCCGG GAAAAGGCAG CTGCCCAGCC TCAGAGATTG
25351 TGGTCGAATG TTTGACAGTC ACAGATGGTG GTGTGGGGGA AAAGGCATTT
25401 ATCACTCCTT GTGGCTCACA GAGGCCAACT ACCAGAGGCT TGATGAGAAG
25451 TATCCTCCCA CACACAGGAG TTGGTTTTCC AAACCTCTTC CCCTCAGTTC
25501 TCTCCCTGAC CACCCACACT CTAGAGGCAG AAGTGACCCT AACTCATGGG
25551 GATTTAAGTA TTGCTGTGTT CTGGACTCCG GGGATACCTG GACCCCAGAG
25601 CTGCGTGGAC ACTGTGGACG CTGGCGTAGG GAAATGCCCT CTACTAGTCC
25651 CAGGATGTGT GTTCTTCATG GGAACAGTCA GGTTTATACT TCCGAGAGCG
25701 TAGTTTAGTT GAAAGGGCTG GGCTGCCCCG ACTAGGATTA ACTCAGACTG
25751 TTTTAAAAAG AAGGAAAGGG GGAAAGGCAG AAACTCTGGG AGACACGAGG
25801 TCCCCTCTCC TCTATTTTAA CTCTTCGGCA TGGATTGTCT ATCTTGTTCC
25851 TTTCCCCTTC TTCCCAACTC CCAGTACCCC TTCTGGTGGC TGTGGCCAGA
25901 AACTCAGCGA ACAGCACTTG TCCTATGCCC ATCAGTGTGC TGGAATTGAG
25951 TGCACGGTAT CTCACCTGGC CTCAGCTCTT CGTCTCCAGA AAAAATAATG
26001 GGCTGCCTGA GCTCTCCCCT CCTGCCTGAG TGGTGCTGCT TTGTGGGTGC
26051 CTCAACTCCC ACTTCCTGTG GACATGCTTT CTTCCATGAG TATAACAGCT
26101 TCAGGTTACC ACCCGCACCC CCACTGGTAT CAGCCTGTGA CACCTTCTGG
26151 GCCTGTAGCC CAGAGCCACA TCTAAAAATA GAGGCCCATC TCCCTCTGCT
26201 ATAAAGCAAA GCCCTGAGAT TCAGCCTGCA AGGACTTACT GAGCACCTAC
26251 TATGTACCTT GTTTGCATCA CCCAGGATGC TGTGGACACA CCTCTAAATC
26301 AGCCTCCTAC TGGGGAGATG GTTCAGAGGA AGAGAACCTT ACACTGAGTC
26351 ACAGGGGATA GAAGTTAGGG GAACACAGGA GAGCAAAACA TTTCAGGCAG
26401 TGGGACCAGC ATGGACCAAA GCCCAAAGGA AAAAGGAAGT GTGGCCACCC
26451 AGGGCATGGC AAGGGGCTGG AGAAGGCTGA GGTCAGATGA CGGATGGGAC
26501 TGCCAAGAGC CAAGGCCAAA AAGTGGCAGG ACCCAGCACT GGCAGAGTCC
26551 ACTGTTGGGT CTGAGATTAT GTAGAGCAGG GTGGGGGTTG GGATTGTTCA
26601 TGGTGTCTAG TAGGGACAA GGGATGATTC CTTACAGAGA CTCAGCAGCA
26651 ACAAGAACTG GGCTTCTCAG TTTGACCAGG ACCACCGAAG CCCCTCTGTA
26701 CCCACTCAGT CATTTAGCCC AGGCCCCAGA GCCCTCCTAT GCTCTTGCCA
26751 TTCTCTCAGA GCGGGCACCA GGGGCTAAAG AGAGTACCCT TTTTTCCTTA
26801 CAGGAGGCCC ACTTGGCCAC GGAATATGTT CAGCACATCC AACAGGCCCT
26851 GGACATCCTC TCTGAGGAGG TAGGAGAGGG GTTACGTGTT CCTGGGTCCC
26901 GCCAGCCACC TCCCTGGGAT GCATGTAGGC AGGCTGTGTT CAGTGAGATG
26951 CTCACGGAGC AGAGACCCGC CATGAGTGAG CACCTGGATG GCAGGGAGGG
27001 AGGTGGCTGT CAAGCTCCTC TGCAGGGAAA ATTCTCACTT GGCCAGAGAC
27051 AGGGTTGTGT GGTAGCAATG AGCTTGCCTC TGAACCAATT GGCCCAGGTT
27101 TGCGCCCAGC ACTGTGGCTT CGGGCAAGTG ACTTCCCTGT GTCTCAGTTT
27151 CTCAACCTAT AAAGCGGGGC CACTCAAGAA GATTCAGTGA GATACTACAA
27201 GTTGCATCCC CTCTCTGGGC CTCAGTTTCT TCATTGGTAA AATTGAGGGG
27251 AGTGGGAATT GGATTGTAGA TGACCCCCAG GTTCCTCCCA GCAGTAGCCA
27301 GTGCCCTAAC GAAACCACCC TCCACTCCCT GCAGCTCCCA AGGGCTTTCG
27351 TCAACGTGGT GGAGGTCATG GAGCTGGCTA GCCTGTACCA GGGCCAAGGC
27401 GGGAAATGTG CCATGCTGGC AGCTCAGTAA GTGGACAGGT CACCGTCCCA
27451 AGGCAAGGGC ACCTGGGGTG AGGAGGGCTT GCAGGTGCCA AAGGAGGAGA
27501 CCAGTTGAGG CAGAGCCAGG CAGGCCTGCC AGAGGGTAGA CATGGCTCAG
27551 GGGCTTGGAC AACATCAGGA AGTACCTCTA CATTTGCAAA TGCCTACTGT
27601 ATGCAAGGTG CCTCATTTCT CTGGACCCCC TTTTGCTTTT CTGTGAAAGG
27651 AGACAGACCA AATGATCCTT AAGGCTCCCT GACATTGTCA GTGATTGCCA
27701 AGGCAAACCT TGGCACGCTG CTCCCTGTTG AGAAGCAGCA TGGGGCCATG
27751 AGCTTTCAAG GCTGCTACAT CCAGCCTTGA CTGTTCTGCC ATTTAGGAGC
27801 TATGGGACCT TGAACAAACC ACATAACCTC TATGAGCCTC TGTGTTCCTC
27851 ATCTGTAAAG TGGGGTGAT GACACCTTCC CTGCAAGGTA GATGTGAGGT
27901 CAAGAGGAAA CAAGGTACCT GGCCTACCAA GACTACCAAG AGCAGGGTCT
27951 TAGGAAATAG CTCTTATTCC ATCCTTGATG GGGCCTGTCC TTGATAGCTG
28001 GGCTTGGAGG CAAGGTGCTA ATGGGCAAGA CAAGAACTCC TATCGGGGC
28051 TGGAAGTCAT TAAAGCTCTT GAACCCTGGT AGGAAGTTGC CATGTTCTGA
28101 GGGCACAGGG CCTCCCACAG TTTGAGTGAT TATTGCTATG AGAGAGGAGG
28151 TTCTCCAGGG AGCTGAGGAG TCCTACACCT GGGCTCAAAT GGATTTGCTG
28201 CAAAGGTGAC CAGCTGGTTC CCATTCTTGC AGGGAACCCT GCTCTCTCGC
28251 AGGGAACGGC TCCTCCAGAG TCTGTCTGTA TCGTGTTCCA TGTTGTCAGG
28301 GTTGCTTCCA GCCGGTTGGC CCTCCCAGC TTTCCCACAG ACTTCCCACA
```

FIGURE 3, page 9 of 33

```
28351 CTGGAGCCCT GAGGGAGGGT CCTAAGCAGT TGCAGGAAGA GCTGAGAGGC
28401 CCCCGGAACT TGAGGAGCGA TTCCAAACCC AGGGACAGAG CCATCGTGGC
28451 TGGTTTCCTA AACTCCAGTC TCCTGTCTAC CCAGTCCTGC TCTGGAGAAA
28501 TCCCAGGGAC CACAGGCTTG GGAAGGAGGA AGGGGAATAG GCGTTCTGTC
28551 CACAGGGAGG TCCAGGCAAC AGCTTTCCCT CTTTCTCTAT GAACAATCAT
28601 CCTCTGGACC TCAGGGCTCC TGAGTTAGCA TTCTGTAACC TGGGTCCAAG
28651 AATCAGCCAA AGGTGTATTG TGGGGATACT TGTGTGTCAC CCCCCGCCCT
28701 AGGTAAGGCA GCACAGGCTG CAGGCCCCTG GGGTAGTGGC CTGCTCTGTG
28751 TGTCAGAGCC AGCCTCCCAG GAGGACAGAG CCACAGTGCC CCAGGCAGCC
28801 TCAATACAAC ACTCCCTGTC TCACAGGAAC AACTGCACTT GCCTCAGACA
28851 CTCGCAAAGC TCCCTGGAGA AGCAAGAACT GAAGAAAGTG AACTGGAACC
28901 TCCAGGTAAG CCCTGCAGCC CTTCTCTTAC TGACCCAGCT GGGGGGCCCC
28951 CTGTACTCCA AGGACTGGGA AATCGAATGC CCAGCAGGAT GTGGCCAAGA
29001 GCAAGCCACT CCCTAAAAGC AGATTGCAGC CCCTGAAATA CTTACCCCTG
29051 CAAATTGAAC ACCAAGGCCA GGGAAGGGAG TGAGAGACCC CAAAGTGGAA
29101 GCTGAGAAAA TCCCCTTCTC CCAGCGGGTA GGCAGCAAGA GATTCCCAGA
29151 GTAGACTCCT TGTGGTAGGG CCCATTCCCC ACCCAGAGCC ATGTGTAATA
29201 ATTACTACTC ACTTCCTCCC CTCCCTTCAT TAAAAACAAA AGGCTTAGGC
29251 CCGACACAAT GGCTCACGTC TGGTGTCCCA GCTACTCAGG AGGCTGAGAT
29301 GGGAGGACAG CTTGAGCCCA GGAGTTGGAG GCTGCTGTTA GCTATGATGA
29351 TGCCATTGTA CTCTGCCTAG ACAACAGCGT GAGACCCTAT CTCAAAAAAA
29401 AAAAAAAGAA AAAAGAAAA AGGCTTAGCC CTGCCCTACT TAACTCTACC
29451 TCAAATTCTC CTTGCCCTCT CTCTGCCCCC TTCCATCTCC CCACCTCCAC
29501 TCCTGCTTAT GTCTCTGCCT CTATTGTTCC CTCTCAGGCT CAGGTAGCAT
29551 TTCCATTCTG CAAACTGACC CTCCTTCATT CACAAGGCAA GTCTGCTTCC
29601 CTCCTCTAAG GAGCTTCCCC TGCCTGAACT TCACCCGCGG ACATCTCCCC
29651 ATATCACATT CAGTCTGTAC TTGATGGGCC CTAAAAGCCC CAAAGGGTTC
29701 TCATGTTTTC ACATCTTGGC TCATTTTTCC AGATGGATGA TAAACTCCTT
29751 GAAGATAAGT ACATCTAGTC TGTTCCTTTT ACATTCCATG CTTGGGTACT
29801 TAAATCCAGC CACCGTGGAC TCTCCTCCCG CAAAGTTCAT GGGCATTTTG
29851 GGAGCTGGTG TTGAGATGCT CCCCATCTGA CCTGCAGCCC CATGTTCTAA
29901 TTGACCTCTT CGTGCAGTGA GAGGAGGGGA GGACTTTGGC CTATGCAATC
29951 TGGTCAGTGG CTCAGACCCA GCCTTTCAGG CAGAGGCTTT GGAATGGGAC
30001 TGGGTGGAGC TGTGTAGCTA GGGAGCTTCT CCCACCAGGA GCCGCTGGGT
30051 TCAACTCATC TCTGATCCTG AGAACCAGCA TAGGGCTTTG AAATGTCCGT
30101 GCCCATGAAT GGGTGGAGAA TAAAAGTATG TTTGCATCCC ACTAGAGTAG
30151 CCCCTTAAAG TCACTGTCCT TTAGGGTGAG TTGACTCCCG TCAACAACCA
30201 ATCCAAGGCA GCAGGACTGG ACCCTGTCTG TGCAGCCTTG CCAGGAGGGT
30251 TGAGCAGCTT CTCTCTCTGT CCCCAGCATG GCATCTCCAG TTTCTCCTAC
30301 TGGCACCAAT ACACACAGCG TGAGGACTTT GCGGTTGTGG TGCAGCCTTT
30351 CTTCCAAAAC ACACTCACCC CACTGAACGA GGTGAGCTGC AGGTATTTTA
30401 GGGAGGCTCA CGTATGGGGG CCTTATCACA GACGATGGAT GTATTTCCTT
30451 CTCTAAGTGG GCTTTTTTTT TTTTTTAACC ATCTCTCTCC AAGAGGATTC
30501 CTGAGGGTGG CTTTTTCCAC ATTACCTCCT TTTTGTGGGG GCTGGGCTGT
30551 GATTGGAACT CAGATGTACT TTGAAAGGAA ATCAATAGTG ACTAAGCTCC
30601 CAGGCCTGGC CCTGATGTTT TCTGGATTGG GATAGAATGG AAAGCTTCCT
30651 AAAAATGTTA CTCTTTTCAA CTCTTAGGAT AGGGGTGCTG AAAGAAAAGG
30701 GAGAGACTAT GGGTGGGTCC AATTCTTGTC TGTTTAAAAA GAAAATTCCG
30751 GCCGGGTGCA GTGGCTCATG CCTGTAATCT CAGCCTTTGG GAAGCCAAGG
30801 CGGTTGAATC ACGAGGTTAG GAGTTTGAGA CCAGCCTGGC CAACATGGTG
30851 AAACCCCGTT TCTACTAAAA ATACAAAAAG TTAGCTGGGC GTGGTGGCAG
30901 GCACCTGTAA TCCCAGGTAC TCGGGAGGCA GAAGTTGCAG TGAGCTGAGA
30951 TTATGCCACT GCACTCCAGC CTGGCTGACA GTGCGAAACT CCGTCTCAAA
31001 AAAAAAGAAA AAGAAAAAA AGAAATTCTA AATTCTGGGA GTTTTTCCAT
31051 CAGTATCTGA GCAAGTTGGC AGGAAAGTTG AAAGAATGAA AGGAGACATG
31101 CCCAGGGCAC CTGCTGGGAG AGTGAGTGGG GCTCAGGTAG CAGAGCCCTT
31151 TCCCAGGATG ATAACCTCCT TGCCGTTGGT TGCAGAGAGG GGACACTGAC
31201 CTCACCTTCT TCTCCGAGGA CTGTTTTCAC TTCTCAGACC GCGGGCATGC
31251 CGAGATGGCC ATCGCACTCT GGAACAACAT GGTGAGCAGC CAAGGGCCTG
31301 GTGGGCCTTG TCAAGGGGGG ATCTAAGGAT ATTGACACTC TGTCTCACAA
31351 TGGCAAAACT ACTGGAGACA TGGCTCCTTT CTCCCCAAAG CCCAAAGTGG
31401 CAGCACACCT TATTGGTCCT GATAGATTAA TTCCAAAGGG AAAATACCCT
31451 ATATTTATCC AACACCCTTT GAAAGTTATA CAAACACACA CTCACACAAC
```

FIGURE 3, page 10 of 33

```
31501 TTTATTCTTT GTTCCTTCAG CAATGCCCAG GTACTGCGAG GGGATCCCTT
31551 TGTAATCAGA TAGGTTGGCT AGATGAAAAT ACCAACTTCT ACCTCGTACT
31601 GTGTGACCTT GGGCAAACGA TCTCTCTGGC CACCTGTATC AACATCTATA
31651 AAACAGTGAA AACAAGACAG GTCTCAGACA ACGCATTGAG ATCATGTGTA
31701 CATGGCACCT AGCACAATAG TTAGCACTCA GCAAATGTCA CCACCATCAG
31751 CCTTCCAAGC ACTCCGGGCT CAACTCATAC CCAACTCATT TCTCTAAACA
31801 TCGAAAAGTG GAGATCCACA CAGCCTGTTT TCCGAGGCTG ATACCTATTC
31851 CAGTCCTTTC TGATGGGAAG AAGGGACCTT ATGAAATGAA CATACAGTCT
31901 GGGGGTCTTT CAGGGACACC TGCCTGGTGC TTCCACTCTG CCTTCTGTGG
31951 CTGGCCACCA GCAACTGAAC GGTTTCCGCA CAGCACTTGA CCTGTCACCC
32001 CCAACAACTG GATCCTCTTG CACGGAGCAA ATGAAATGCC TTCCCAACCC
32051 AATGGTTTCT TTTAATCCAG GCTCAGTGGG TAACACAATC CCCACCCCAA
32101 CCTGTATGTT CCCTCCTTTG TCCTATGACA ACTAAACAAG CTACATTCCA
32151 GCTCCTTTTA TCACAGTTTC AGGCCCGTAG TGTCTCTGCC AACCACCGCT
32201 GTGCAAACGT TCCCACCCCT GTCAGCTCAT CCAGTATGTC CAGCATCCCA
32251 CTCGGCTGAC TCACAATATT GACTTTCTCC TTAGCTATAC CATCTCCTCC
32301 TCTCTAGCAA CCTCTTCTTT TAAGAACAGC ATGTAAACTG GCTTTATCCT
32351 TGGCCTAGTT AATGGCAGAC TCAGCTTATG TCGACTTCCA TTGTCAGGGG
32401 GTTTTCCTCC TGTGGACATC ACGTACCTGC CCACTCCAAG AACTTCTATT
32451 GTACTCTTTC AGCCCAAGAC TCCGGATTGT AACCAAAATG TCTTTGAGTT
32501 TGCCCCACGA TTTTTAAATC AGTTTATATG GTATAATTCC TGTTTCTTTT
32551 GTGGATTTTG TTTTGAAGGC GGTTGTCTTT CACTGGCTGA ATCATGTGAC
32601 TTTATTCCTT TGTAAAAATC TTCCCAAAGA AAGGGTACCT ATTCCCTGTT
32651 CCTTTTCCCC TGAGACCTCA GGGGATTCCA CAGATGCCCT TGGCCCTTCC
32701 TTCCCAGTTT TTTCATCAAG GTATGGCCTT CCTACCAGGT GGCACTCCAA
32751 GTCTGCTTAA ATCTGGGACC CTCCAGGAAT CTCCTGGGGC TGGATAGCCA
32801 TAGTGACGGC TGGAACATGA AAAAGAGTCC ATTGGTTTCT TTTCTTGTGA
32851 ATTAACAATG TAGCTCTGGC CAGGCACGGT GGCTCATGCC TGTAATCCCA
32901 GCACTTTGGG AGGCCGAGGC AGGTGGATCG CTTGAGCCCA GGAATTAGAC
32951 ACCAACCTGG GCAACACAGG GGAGATTCTG TCTCTACAAA AATAATCAAA
33001 ATATTAGCCA GGTGTGGTGG TGCATGCCTG TAGTCCCAGC TGCTCAGAAG
33051 GCTGACGTGA GAAGATCACT TGAGCATGGG AGGTCAAGGC TGCAATGAGC
33101 CGAGATGGCA CCACCGCACT CCAGCCTGGG CAATAGAGTG AGACCCTATA
33151 TCTCAAAAAA CAAATAGAAA AAAAAAATAT ATGTAGCTCT GGCCTTCTCT
33201 TCTAAAGCAG TTCAGTAGCT CTTCCCATTC ACCCAGGTAA GAGGCCTTTA
33251 TTTCATAAAG ATAAGTGGGA GGAGTTTAGA TATGAAAACA AAACGTAAAC
33301 ACCGCACTGG AGCTATTGTG GAAACAAAAC AAGACTGTCC ATGGTTCCCC
33351 AGCCATTATT ATCTCAGCCA TACCCCGAAT TTCAAAATAA CAAAAACAAA
33401 ACTAAAGCCA TCCAGGGGTT TCTTATCCTA GGCTCTATAA TTTGGGTAAA
33451 TAATTATACA GTCTAATGTT TTCATCCAAA GCCAATCTTA GACATAAAGC
33501 TGTAGCATGA TGCCAACTTT TCAGATCGGC TTCTGGCTGG AATTTCACCC
33551 CTAGAGTAAC AAAAAATAAA TAATAGACCA TTAGAGCTGG AACAGACTGA
33601 GAGGTCATCT AGCCAGAACA TTCTGTAACT AAAGCATAGA AACATGAAGC
33651 AGTTTGCCCA ACATAACACA GACTGTTCAT GGCACAAGGG GGATTACAGA
33701 CCAGGTTTTT CTAGTCCTTT CCTGGTGACC TGGGCATGCC ACCACCCTCC
33751 CCACTGCTCC CAACCTGATA AGCACATATA TACCCGGTGA ATTCATGTCT
33801 CACAATTAGA GTCCTATGAC ATAGTGTCTG CAGGCTTTGG CTGATGTTCC
33851 CATAGTGTCT GCAGGCTTTG GCTGATGTTC CCAGGGTTCC CTACTAGGAA
33901 GCAAAAAGCA CCTTAAACTA TTTCATCTTA TTTCATCTCC TGCCCCTCCT
33951 CTCACGTCCT TCTCGAGACT TTTGCAAAGG CAAAGCCAGA AGCTCCAGCA
34001 GCACCAGGGG ATATTTTCCT CTTCCTCTGC CTTCTTCTGT CTTCTTATCT
34051 GAAGAAGTTT CTCTTTCCCG AGGCCTAGTC CTCTACTGCT GCCTCTACTC
34101 CCTCTTCTGC AGAAATCCTG CTCTCAGCCA GTGTTTGTAT CTCCCCAGGT
34151 GCTGGGTGAC AGCTCCAGCC TCCTAACTGA CATCCCTGTC TTCAGACTTA
34201 GAGCTCTTAG AATCGTGACT CTCAGCTCTG GCTGCATATT AGAATCATTC
34251 AGGGACATTG TGTATGTGTG TATGTATGTG TATATATGTA TGAATGTGTG
34301 TGTATGTGTG TGTGTGTATG TATGTATGTG TATGTGTGTA TGTATGTATG
34351 TATGTATGAC AGAGTCTCAC TCTGTTGCCC AGGTTGGAGA GCAATGGCAC
34401 CATCTCAGTT CACTGCAACC TCCGTCTCCT GGATTCAAGC GATTCTCCTG
34451 CCTCAGTCTC CCAAGTAGCT GGGGTTATAG GTGCATGCCA CCATGACCAG
34501 CTAATTTTTG TATTTTTAGT AGAGACAAGG TTTCGCCATG TTGGCCAGGC
34551 CAGGCTGGTC TTTAACTCCT GACCTCAGGA GATCCACCCA CCTCGGCCTC
34601 CCAAAGTGCT GGGATTATAG GTGTGAGCCA CAATGCTTGG CCATCCAGGG
```

FIGURE 3, page 11 of 33

```
34651 ACTTTTAAAA CAATTAGTGC CTACAGCCAC TTTGGAAAAT TCTTTGGTAT
34701 ATTTAATAAT GCTGAACACA TGTATTTCCT GTGATCCAAG GATTTCACTC
34751 CTAGGTATAT CCCCAAAAGA AAGGTATATA TGTGTCTACC AAAAGATACA
34801 CACAAAAATA TTCACAGCAG CACTATTTAT AAATAGCCCC AAACTAGAAA
34851 CTCCCCAAAT GTCCACTGAC AGTAGGATGG GTGAGTAAAC TGTGGCACAT
34901 TCATACTAAG GAATACCATA CAGGTCTGAC CGCATCTGTG GCTTTAAACA
34951 AAAATCAAGC AGGGTGATGT GACACAGAGT AATGGCTGGG AAGAGGGAGG
35001 CCTCACTGAA GAAGTGACAG CTGAACAAAC TTCAACAACA TACAATAATA
35051 TCTATAAAGT TCAAAAGCAA GCAGCTTGGC ATATGGGTT AGACGTCAGC
35101 ATGATGGTGT AGAGACTCAC TGGGGGATGA ATAGTCCTGG AAGAAGGTGG
35151 AAAGGGGCTT TGAGGACTA TAATAGTCTG TTGCCTGACT GGATGCTGGT
35201 ATGTTCATTT TATCGAAACT TATCTGTTGC TCACTTATGA TTTGTACTCG
35251 TTTCTATGTG TATGTTAGCT TCAATTAAAA GTTTACTTGA GGCCGGGTAC
35301 AGTGGCTCAC ACCTGTAATC CCAGCACTTT GGGAGGCCGA GGCAGGCAGA
35351 TCCCCTGAGG TCAGGAGTTC AATACCAGCC TAGCCAACAT GATGAAACCC
35401 CATCTCTACT AAAAATACAA AATTAGCCAA GCGTGGTGGC ACGTGCCTAT
35451 AATTCCAGCT ACTTGGGAGG CTGAGACAGG AAAATCGCTT GAAACCAGGA
35501 GGCAGGGGTT GCAGTGAGCC AAGATTGCAT CATTGCACTC CAGCCTGGGT
35551 GACAAGAGTA AAACTCTGTC TCAAATTTAA AAAAAAAAAA AAAAAAAAGT
35601 TTACTTGAAA AACAATATCA GTGCCTGACC GGGCTTATCC CCAGAGAGTC
35651 TGACTTAATT GGTCTGGAGT GCGAGCTGGA TTCGGTACTT TGTGAAAGCT
35701 CCTGAGATTA TTTTAATGTG CAGGGTTTAT GAACCGCTGC CTTAGATCTG
35751 GTCCCCACAG AGAAATCAAG TAATCTGTAT AAAAGAAAAC CTGACCCAGT
35801 CACTCCCCTG CTTTCAAACT TCCAAAGCCT CCCACCTCTG AAGGAGGCAG
35851 GCCAGGCCCC ATAGCACAGC ACACTAGGCC TCTGGGACTT GGCCTGGTTC
35901 ACCTGATTAA CCTCTCTGGC TACCATTTCC ACCAGCGTCT GCCTCGCATG
35951 TTACAGTCTA GTGACTCCAG CAGCGTCCTG CACCACCTGT GGTGTTCCAC
36001 ACCTCTGCTA ACTCTTGCTC TCCTCCTTCT CCTGGATTGC CCTTCTCACC
36051 TCCTTGCCCA CTCCACCACT CAACTCAGGT GCCACCTCCT GCAGGAAGCT
36101 ACCTCTGAAT CTCCAGGACA GGCCAGTGGC CCACCCAGGT CCATTACACC
36151 CTGCCCAGTC CTGTCATTTG CTACGTGGTT GGTAGCCACA GTGCCTGGCT
36201 TAGGAAAGAC TGGTTCTAGG AAAAACAATT TCATTCCCTG TGGCCAGCTC
36251 CAAGCCTTCC CCCGCCAAGC TTCTCCATTC AGGTCTCTGT GAATTTAATT
36301 AATTCATCCA TCCATCAAAC AAGTATTTAC TGAGCACTAA TATGTGCTAG
36351 GTACTGCTCC AGGTGCTGAG GACTCAGCAG TGAAAAGATG ACTGCTACTC
36401 TCATGGGACA TACAGGATAG TAGGGAAAAG ACAGATAATC AACAAGGTCA
36451 TTTCTGACCA CATCTGTGGT TTAAGAAAAA GTCAAGCAGA GTGATGTGAT
36501 ACAGAGTAAT GGTGGGGGAG AGGGAGGCCT CCCTGAAGAA GTGACAGTGA
36551 ATTGAGAAGC GCATGTCAAG GGGTTGCCAG GCAGAGGAAA TAGGACCCAC
36601 ATGGGCCTAG AGTCAGGAGT GAGCTTGAAG TGTCTGAGGA ACTTAAAGGC
36651 CAATGTGACC AGAGGGAAGT GAACAAGGTG AAAAAGTTGG GCAGGGGCCA
36701 GGTCCCTAGA TGCTTCTAAG CAGTAGAGTG ATATGCTCTG GCTTACCCCT
36751 GGGTCCGTGT ACCCTGGACT GGAAGAAAGC AAGGGTGGAC CTGGAAAGAC
36801 CACTAGGAGG CTGCTGTTGA TGGGTGAGAG AGGAAGGGGG CTGAGAGTAG
36851 GGTCAGGGCA GAGGAGGAGA GACGCTGTCG TGGGCTGGTCT GATGGATGAT
36901 GGGGAAGAGG AACAAAGGAT GACTTTTTGG TTTGGGGTCT AAGAAACTGG
36951 GTGGATGATT GAGCAGGTAG AGAAAAAATC AGCGTGGGAG GAAAAAAAAT
37001 CAAGACTTCT GTTTTGGACA TGGTGCAAAC TGCCTTCCAG ACATCCACAT
37051 AGAGGTATCA GGATACAGAA GTTTGGAACT CACAGAGGAA GTCAAGGCTG
37101 GAGATTGAAA AAAAAAAAAA AAAAAAAAAA AGTGGGGTTA TTAGCATAGA
37151 GGGCCAATAT GGTGAAACCC TGTCTCTACT GAAAATACAA AAATTATCCA
37201 GGCATGGTGG CATGCACCTG TAATCCCAGC TACTCAGGGA GGCTGAGGCA
37251 GGAGAATTGC TTGAACCCAG AGATGGGGTG GAGGTTGCAG TAAGCTGAGA
37301 TCGTGCCATT GCACTCCAGC CTGGGTGACA GGGCAAGATT CCATCTAAAA
37351 AAAAAAAAAG CCACTACAGG ATCAACTAAG AGCTCCTAGA GAAAGAATAG
37401 GTAGGTAGAA AAGAGTGTAA GGCCAACTAC CTAGCCCTGG GCATTCATTC
37451 CAGCTTTCAA CTCCAGTGAG AGATAGAAG GAGAGTGTGG AGGTAGATGG
37501 GAAATGAGAA ACAATGCTGT GTCCAGAGAG CTAAGAGAAG TCAGTGTTTC
37551 AAGAGAGACA GAGCTGTCAA CTTTGATGGA TGCTTCTGAG AAGCCAAGCA
37601 AGTTGAAGAC AAAAAAAAAA AAAATGATCT TTGGCTCTGC CCATATGGCG
37651 ATCGTTGGTG GCCAGGGCCA GAGCTTCCAT CCAGCGATGG AGACTGCAGA
37701 CTGGCTGGAG CGAGCAGCAG AGAGAAGGAG AGATTAGGAA GTGCTGCCAG
37751 CACCTATAGA CAGCTCTTCC CAGAAGTTAT GAGAAGTAAC AGCCACGGTC
```

FIGURE 3, page 12 of 33

```
37801 ACTGGAGGGG ACATGGATCA AAGAAAGGGC AGGTGAAGGA GGGGAGATGT
37851 CGGAGCAGGT TGTGTACTGA CGAGAAGGAA CCAGTAGAAA GGGAGAAACT
37901 GATGCACTCA TCAAACCCTT GTAATCACGA TCATCTTCTG TGTGAATTAG
37951 TTCTGGGTTC CTGGAATAGC ATCGGGAATC AGCCGCGCTG ACCTTTAGCA
38001 TTTATTCTGT CACTGTTACG ATAGACTTGA GTTTCCTCAG TTCTTAAGAA
38051 AGTGGAAATA ATACTACCTT ATGTATGTAA GCCACCCCAA TCACACGTGC
38101 TTTCATGCCA TCTTCTCATT TGATGCTCAC AACAAACCAA GGTGTCAGGA
38151 CAGGATGTCA TGCCTGTCCC TAACCTCAGA GAAGTAGCCA GCCCAGCACT
38201 GCACAGCTCG TTACCAGCAG AGCCTGGATC CCAGCCATCT GCCCATCGTG
38251 CTCAGTCTAG TCACCCTAGC ATCTCTCCCA GGAACAGAAC TGCCCTCCCT
38301 CCTCCAATTG TGTTACTAAG GAACGGGTGT AAAAGGCCTT CAGACAACAG
38351 AAAGTGAGAT CATGGGCCAG GTGTGGTCAT GAGCTCAGAT AGTGAACTTT
38401 CACCTCCCTC CCTGGCAATA CCCTGTGGTC AGGAGCAGGC AGATTACACA
38451 AAGAGTGGAG GCTAGACGTT CCAAACAGAC TCTGAATAGG TGACAGTGCC
38501 AGGGGCTCAT TCTTCTCAGT GCTGGCCACA GGTTGGGCCT GGCTGCTGGC
38551 TAAAAGGTGC CGGGGAGGGG GATACAGCAG CTCCCAGCTC ATCCTCAGAG
38601 GGTCCTGGGA TCAAAGGTAT TTACACCCAG GGATATTTCA GATAAATCTT
38651 TTCATCTATG TGGAAAACAT ACAAAGTGGC GCAAGTGAGA AACTCCGATT
38701 TCCTAAGGTT GACAAGTCAA GTGCAGTAAT GATGTCATGG TAACCAATAT
38751 GTTTCCAAAC TTTCCTAAGG TTGACTAGCC CCATGCACTT TGAGAAGTTG
38801 GTAAATAGGA TTGTCGTCGT TTTATAAAAT TGAAAACACG GTGTCTTGCA
38851 ATCACAGCCA CTCACAAAGG AAGCCAGAGA TGGTCCCAGC CCCTCCGCAG
38901 ACTTCCTGTG GACTCAGGAC TGGTGGTCTC TCCTGGGCCT TGCTGTACCC
38951 GGCAAATCCA GGGGCACAGA CTCAGGGTTC TGCCCTGCCG ACAGATGCTG
39001 CCTAGCCTTC TGTGTGTCAT AAGTCAACTC CCGCTCAGCC CCAGGCTGCT
39051 GGGTCCCTGC TGTGGGCCAA AAACCAGCCA CTTCGCTGGT TTCTATCCCC
39101 CACCCCGTTC CCGAGGGAGG GGCTCTGGTG TGAGACACCC CCTCAGAGAG
39151 GAAAGTGTCT CCCAGCTTTG GAGAGAATCG AGGTGTCCTT TCTCTCTCTC
39201 CAGCTGGAAC CAGTGGGCCG CAAGACTACC TCCAACAACT TCACCCACAG
39251 CCGAGCCAAA CTCAAGTGCC CCTCTCCTGT GAGTAAACGT CCTGCCTGCC
39301 CCAGGTGGAA CAGATGCCTG GGGTGGGGGT TGTCCTGTCC CCTGGAAGCA
39351 CAGAGGAGTC CCCGGGGATG CTCCCTCAAA TGCGGCTTCA CTCACTGCCG
39401 TCTTCTCAAA TCCCACCTGT CCCCAGTGCC ACGGAAACTT CTCAGTGTGT
39451 GGGCAGCCAT GGAGGGAGGG GAGAGGACGT TCAACAGCTC CAACCGAAGG
39501 GAGGACAGTC GCTCAGGGAG GCAGATGAGC ACTGGCGGGT GTCTCGGGTC
39551 ACCCATTCCT TCCGAAAGCT CTGATGCATC CTCAGTCTTA AAAGTGCACC
39601 AAGGCCAGGC GTGGTGGCTC ACGCCTATAA TCCCAGCACT TTGGGAGGCC
39651 GAGGCGGTCA GATCACCTGA GGTCTGGAGT ACAAGACCAG CCTGGCCAAC
39701 ATAGTGAAAC CCCGTCTCTA GTAAAAATCC AAAAGTCAGC CGGGCATGGT
39751 GGCGGGCGCC TGTCATCCCA GCTACTCAGG AGGCTGAGGC AGGAGAATCA
39801 CTTGAACCCG GGAGGCAGAG GTTGCAGTGA GCTGAGGTCA TGCCACTGCA
39851 CTCCAGACTG AGTGACAGAG TGAGACTGTC TCAAAAATAA AGTGCATCAA
39901 GCAGCTGTCC CGTGCCAGGC AGTATACTAG GATCTGGGA TCGGGAGGCA
39951 AAGATAAAAT AGACTCAGTG TCTGTTCCTG GAGCCTGCAA TGGTCTTCCT
40001 CCCTCGCCAC ACCCACTGCC CTTGCCTGGC CCACCTTCGA AGCCTGTGAC
40051 TTGTCTCCCC AGCTCTCCTC TCCCTCTTCT CCATCCACCC TACACTTGCT
40101 GCCAGACACA GATAGACCTT CCTGGAAATA ACTTGCCCCA TCAAGGCTGC
40151 TTGAAATCCT TGCCTGATCC CTACTGCCCA TTGACCAGAG TCTGGAGGGA
40201 GGGTCACCTC CCTCCATGAT ACACACTGCA CTCCTGGCCG GTGGATCCAT
40251 CTCCCAGGAA GCCCACGAC TGCCCGCATC CAGGCCTTTC CTTTTGCCAT
40301 CTGTTCCTGG AGGTTCATCT TCCATCTGCT ATGAGAACAT CCGCCTCCCT
40351 CCAGGTCCAG ATGTTGCCTT TACTAAGCGA TGGTTTCACC GTCTCTTACC
40401 TACCATTCCT GTCTCCAGAC ACTGACCCAT GTGGGTCTCC TTTTCTATTT
40451 GTACCTCTCA TGAGACACCG ACCCAGTCTC CTTTATGATG TGATTGTTTC
40501 TGCACATCTC AACTTCCTCC TGGGCCACAA GAAAAGATGT CACATCTTAA
40551 CCCTCCAGTC TCATCACAGC TTCCAGCAAG GGGCTAAAC ACAGCACGTG
40601 CCCAATTCAC ATTCACTGAG AGGAGAGTGG AGAGGGCAT AGGAAGGCAA
40651 GAACGCACAC GATCTGCCCA CATGCCTCCC CTCCCGGCCC TTCTGATTTG
40701 GGGATCTTTC ATCTACTACA AAACCAGCTG TCCTTCCATG CTGCCCTTCC
40751 CTGATTTCTG GGTAGTCCTG GGATGGGAGA ATGGGGACAG TTGTGACCAC
40801 GAGGAAGCAG AGGTGGGAGT TCTACAGGCC CCACAGGGCT CTCTGCCATT
40851 GGTCACCTAT CAGTTCCCAA TCTTTCAAAA TCAGGTTTGA TGGCCAAGGA
40901 AACGCTGGTG AGAAACCAAA AGAAGGTTCT AGCTGGGTGT TGACCTCTTT
```

FIGURE 3, page 13 of 33

```
40951 AGAGGCCCAT CCCGCTAAAG AGGGTTTGGG CACAGCCTAA ATGAGGGAGC
41001 TTTACAAAAG GGAAGCTCTG TGAAAACGTG CAGGGTTATC GCAGCATCTC
41051 AGGAATGGGG ACTAGGCAAG TCTTGGCTTG GTGATGGATG GTTCACGGAG
41101 ATCCTTTCCA CTGACCCCCG CTCCTCCTCC ACAGGAGAGC CCTTACCTCT
41151 ACACCCTGCG GAACAGCCGA TTGCTCCCAG ACCAGGCTGA AGAAGCCCCC
41201 GAGGTGCTCT ACTGGGCTGT CCCAGTGGCA GCGGGAGTCG GCCTTGTGGT
41251 GGGCATCATC GGGACAGTGG TCTGGAGGTG CAGGAGAGGT GGCCGGAGGG
41301 AAGATCCTCC AATGAGCCTG CGCACTGTGG CCCTCTAGGC CCGGGGGTGG
41351 GTCCTCACCC TAAACTCCCT ATAGCCACTC TCTTCACCGC CCTCTGCCCC
41401 AGCCACTCCC GGCCACCAGG ACATGCTTCA ATGCCTGGTG CCATAGGAAG
41451 CCCAGGGGAC AGTCACAACT TCTTGGGGCC TGGGCTTCTT CCAGGCCTAT
41501 GCTCCTGGAA TGGATACATT TAAATAAAGT CCAAAGCTAT TTTATTCCTG
41551 GGTTTGCCTG CGTGAAGCAC TCACCTTCCA TCTCTTGTGC AGCCCAGGTG
41601 TGGGAGCTGC CACTTTTTGT GGCCTGCCTC AGCAGGGCT GCCCAAGCCA
41651 CGACCAACCA GAGCCCAAAC TGCCTGCCAC CACGAGCATA TCCTCAAGTC
41701 ACCAAACCCA CTATTTCAAA GGCAGAAAAA ATGCTGGTCA CCAGGTGGTG
41751 GCTGGAATTT TGGAGCTGGC TGGTTGCCAT TCAGTCCAAT CCAACACATA
41801 CCTATTAAGC AACTGTTTTG TATCCAGGAC AATGCGAAGC ACTGAGGTGC
41851 CTCCTAGGCT GTGCATGTCG CAGCCTGGCA GAGAGGTCAA ACTCCTTCAA
41901 TAACCAAGAA GCCACGTGAT GATGTGTAAC TACTAGGGCA TCAGTAGGTA
41951 AATGTGTCTG ATTGTTTTAA AGAATAGAAA GGGTTCTTCG GGGAAAGTTT
42001 CTTGGGGGAG AGCAACCTTC ACATGTCATT TTGGGAAAAG GAATAAAAAA
42051 TGATTGGGAC ACAAATACCT CCTATATTCT CAACCTGATT TTCTCAAGGT
42101 GCTAAATTTA GGAAAAAATT CCTATTTCTA TATGCCCAGG TTTCTGAGGG
42151 AAAACTAGAG AGAGTCTGAA AATATGGGCT GCATTCACTG AGCCCCTGCT
42201 AGGGGCGAGG CCCCGTGCTG GAGGCCTTCC ACAGATGGTC TCTTTTATGC
42251 TGCACAAAAG CCCAGGGAGG GGGTAAAAGG AAAATCTTTG AAAATAGAAG
42301 TGATGCTTGC GCAACACCGT GAATGTACTA AACGCCGCGA ATTGTTCCAT
42351 TTAAAATGAT TAATTGTGTA TCATGTGAAT TTCACTTCAA TAAAAAAGAA
42401 TCCAGGGAGG TAGACATCAT CTGCATTGTA AACCTCTCTC TGATCCTGAA
42451 GTCCGGGATG ATAAAGAGCC TGAGTCACAA TCCGGATGC AACACTGAAA
42501 TGCTGTGCCC TGAAGCTGCC TTCGCCAGCC TGAGCCCAGT GTCCCAGGCT
42551 CTGCATCTGT AAAAACTGGA GTAAGAGTAC ACATTTTGCT TATCTCACGG
42601 CGCTGCTGAA AATAAGGAA CCGTGTGTGA ACCTCTAACT CTAAAATGCT
42651 GCACAACTGA AAATGGCCTT TTTCCTCGGT GAAGAGTTGG GATAAGGCCC
42701 AGACTGTTGG GGAAGATGTG AGACCCAGAG ATGAGTTTGG GGAAATGGGG
42751 TAATAACATA TGGGTGGAGA GTGCCCGCCT TCCTCTCAGG GAGGTTCATC
42801 ACCTTATCTC TTTCTGTCAC AACAGAGAAC CCGGAGGACC TATACCCAGT
42851 TCCGTGTTCT TCTGGGCTTC AGTGTCTGTT TCTATACAAT GGGAACAGCA
42901 TGCATTCCCC TGCTTTTTCC TATAGACTGG AAAACGTGGT GACCAAGTCA
42951 CACATCCCAG CTTATGCTCC CGGCTTAAGA CAGTGTAACG ACAAAGGTAA
43001 CCCTTACACT CCTGGTTTGA GACAGTATAA CGACAAAGGT AACATAGGAA
43051 GTCAAGGAGT TCGCTTCACC GCCCCTCCCC CCACCCCACC CTTTTTTTTT
43101 CCTGCAAGTT TCTATTCTTC CCGCAGCTCC TACCTCAAAG CAGCATGGAT
43151 TCATAACCAC AGGCTCCCCT CATTAGGGCT TGGGGAGGGA GGGTGTTGGA
43201 ATCCACACTG CCAGAGTAAT CCAGACTAAA ACATCAACAA ATGGTCCCAG
43251 CTGGTTCACC AAGGAACACT TGGCAAAACA AAGAAATCCT GTCTGGAGCG
43301 ACACGGACAC AGCCACAAAC CAGTCACCAA ATTCCCAGCA AGTATGTGCT
43351 AAGAAGCCAA AAATTAAAAA TACGTGAGAA GCACCCACTT GAAATTGGTG
43401 GTATTACATA CATACACTGG CTGTGCGCCA TGGGGTTTTT CTGTAGGAAA
43451 ATGTCCAGTC TAGCTAGAAC GGCACCCACA GCCACACCAT GAGCAAAGCC
43501 ACCAAATACC TGAGGAAGCC ACAGTCCATG GCACTCCCCA TGG
```

FEATURES:
Start: 3000
Exon: 3000-3098
Intron: 3099-4565
Exon: 4566-4637
Intron: 4638-12578
Exon: 12579-12644
Intron: 12645-16277
Exon: 16278-16338
Intron: 16339-16891

FIGURE 3, page 14 of 33

```
Exon:     16892-16950
Intron:   16951-18968
Exon:     18969-19036
Intron:   19037-19303
Exon:     19304-19347
Intron:   19348-19582
Exon:     19583-19682
Intron:   19683-23297
Exon:     23298-23349
Intron:   23350-24668
Exon:     24669-24749
Intron:   24750-26803
Exon:     26804-26869
Intron:   26870-27334
Exon:     27335-27426
Intron:   27427-28826
Exon:     28827-28905
Intron:   28906-30276
Exon:     30277-30381
Intron:   30382-31185
Exon:     31186-31281
Intron:   31282-39203
Exon:     39204-39278
Intron:   39279-41134
Exon:     41135-41335
Stop:     41336
```

CHROMOSOME MAP POSITION:
Chromosome 2

ALLELIC VARIANTS (SNPs):

| DNA Position | Major | Minor | Domain | Protein Position | Major | Minor |
|---|---|---|---|---|---|---|
| 1573 | A | T | Beyond ORF(5') | | | |
| 1737 | T | G | Beyond ORF(5') | | | |
| 2498 | T | C | Beyond ORF(5') | | | |
| 3097 | C | T | Exon | 33 | A | V |
| 3116 | A | G | Intron | | | |
| 4823 | G | A | Intron | | | |
| 4924 | A | G | Intron | | | |
| 4989 | A | G | Intron | | | |
| 5274 | C | T | Intron | | | |
| 5792 | - | T | Intron | | | |
| 5871 | G | T | Intron | | | |
| 6562 | C | T | Intron | | | |
| 9859 | G | A | Intron | | | |
| 9875 | A | G | Intron | | | |
| 10279 | C | T | Intron | | | |
| 10474 | - | G | Intron | | | |
| 10566 | C | T | Intron | | | |
| 12038 | G | A | Intron | | | |
| 12159 | G | A | Intron | | | |
| 12979 | A | G | Intron | | | |
| 13865 | C | A | Intron | | | |
| 13964 | A | G | Intron | | | |
| 14087 | C | A | Intron | | | |
| 14309 | G | A | Intron | | | |
| 16028 | G | T | Intron | | | |
| 16375 | C | T | Intron | | | |
| 16705 | G | A | Intron | | | |
| 19708 | G | C | Intron | | | |

FIGURE 3, page 15 of 33

| | | | | | | |
|---|---|---|---|---|---|---|
| 21406 | G | A | Intron | | | |
| 22401 | T | C | Intron | | | |
| 22926 | A | T | Intron | | | |
| 23007 | G | A | Intron | | | |
| 23180 | C | G | Intron | | | |
| 26490 | A | G | Intron | | | |
| 26505 | A | G | Intron | | | |
| 29336 | T | C | Intron | | | |
| 29829 | C | T | Intron | | | |
| 29830 | G | T | Intron | | | |
| 29840 | C | T | Intron | | | |
| 29944 | C | T | Intron | | | |
| 30468 | T | - | Intron | | | |
| 30471 | T | - | Intron | | | |
| 30802 | G | A | Intron | | | |
| 30894 | G | A | Intron | | | |
| 30907 | G | A | Intron | | | |
| 31447 | C | A | Intron | | | |
| 31603 | G | A | Intron | | | |
| 31685 | A | G | Intron | | | |
| 31833 | C | T | Intron | | | |
| 31970 | C | T | Intron | | | |
| 32177 | A | G | Intron | | | |
| 33018 | T | C | Intron | | | |
| 33090 | T | C | Intron | | | |
| 33993 | C | T | Intron | | | |
| 34284 | G | A | Intron | | | |
| 34314 | G | A | Intron | | | |
| 35392 | A | G | Intron | | | |
| 35599 | T | A G | Intron | | | |
| 35997 | C | A | Intron | | | |
| 36085 | C | T | Intron | | | |
| 36270 | C | T | Intron | | | |
| 36481 | G | A | Intron | | | |
| 36619 | G | A | Intron | | | |
| 37088 | G | C | Intron | | | |
| 37204 | G | A | Intron | | | |
| 37485 | G | A | Intron | | | |
| 37624 | - | A | Intron | | | |
| 37685 | C | T | Intron | | | |
| 37769 | C | T | Intron | | | |
| 38897 | G | A | Intron | | | |
| 40155 | A | G | Intron | | | |
| 40355 | G | C | Intron | | | |
| 40486 | T | C | Intron | | | |
| 40512 | A | C | Intron | | | |
| 40622 | - | A G | Intron | | | |
| 40654 | T | C | Intron | | | |
| 40933 | C | G | Intron | | | |
| 41171 | T | C | Exon | 418 | L | L |
| 41379 | T | C | Beyond ORF(3') | | | |
| 41388 | C | T | Beyond ORF(3') | | | |
| 41880 | A | C | Beyond ORF(3') | | | |
| 42278 | G | A | Beyond ORF(3') | | | |
| 42339 | G | A | Beyond ORF(3') | | | |
| 42612 | A | G | Beyond ORF(3') | | | |
| 42817 | T | G | Beyond ORF(3') | | | |

FIGURE 3, page 16 of 33

Context:

DNA
Position

1573
TGGCTGTCCCCACACTGGAGATGCCCTCACCTCCTGGTCTGGCCCACATGCAGTGGTGAT
GCCTCAGGGTCTTTGTGACTTGGTCTATCCATGTGTCCAAGTCTGTAAAGGAGGACTTCT
GCCAGAACGTCCCCTTCCAGAGGCTGGAGCCATGACTCCCCTGTTACCCAACTTCAAGGT
GCCTGGCAGGAACTTCTATGATACCAGGCAGCCACAGAGGGGAGGGATCAAAGTTGGGAC
AGAGGCTGGTGTTTGAGAGACAGGATAGCCTAGACTGTGAACATGGGCAGTGGTTAGGGA
[A,T]
GTAGACATATGTGGTCAAACTGTAACAGAAAGCAAGGAAAAGGTACAAGCAACTCAGTTA
CCTTTAGGGGAAGAAGAGAATTAGGAGGGACACAGGGAGCTTCAAACTGGGAGTGTTTTG
TTTCTTAAACTGGGCCATAAGTACATGGATGTGTGTTTTATTATTCTTTATATCTTACAC
ATCTATTTACTCAGCAAATCTTACAGAACTTCCTGTGTACCAGGCATTGTTTCAAGTGCT
TTAGAAATCTCTCTCTTAAGTAGATGTGATGGGTGTGAAATAATTCATGATGAAACCAAA

1737
TACCCAACTTCAAGGTGCCTGGCAGGAACTTCTATGATACCAGGCAGCCACAGAGGGGAG
GGATCAAAGTTGGGACAGAGGCTGGTGTTTGAGAGACAGGATAGCCTAGACTGTGAACAT
GGGCAGTGGTTAGGGATGTAGACATATGTGGTCAAACTGTAACAGAAAGCAAGGAAAAGG
TACAAGCAACTCAGTTACCTTTAGGGGAAGAAGAGAATTAGGAGGGACACAGGGAGCTTC
AAACTGGGAGTGTTTTGTTTCTTAAACTGGGCCATAAGTACATGGATGTGTGTTTTATTA
[T,G]
TCTTTATATCTTACACATCTATTTACTCAGCAAATCTTACAGAACTTCCTGTGTACCAGG
CATTGTTTCAAGTGCTTTAGAAATCTCTCTCTTAAGTAGATGTGATGGGTGTGAAATAAT
TCATGATGAAACCAAAGGGGACACAGTAGGGCACTCATGTGAAAGAAGGAGAGGTCTAAG
GCATAGCATCAGAGGCCCCAAAATATCAGCTCCAACACCAGAGGATGCATTTTCTTTTTA
ATTAAACACTAAATTTTCACTGCCCAAATTCATTTGCTCAGCTGAATAATCGGTTGCAGG

2498
AGGGCGGGAGGGAGCCTCTCCACCCCTCCCCTGAACCTGGGCAATCAGAACCAGCCCCTG
ATGGAAGCCTGAGCTCTGGGGCCTCCTGCCTCCCCCTCTTTGTGCAGCGTTTTGTGTAAC
TGCGTTCTGACCCTGCGGGAGAACTCCCAAGAGCTAGCCAGGCTGGAGGCCTTCAGCCGA
GCCTACCGGGTAAGACCAAGAAGGGCACCATGCTGTGTCCTCTCCCCTACGTTCACTCTA
ACACACAGCCCAGAGCCCCTAGAGGAGGCACACAGGGAAGGAAAAGCTGGTCAGGGATTG
[T,C]
GGGGAGACGGGGAGCAGCCTGGGTGCCTTCCTCTGTCTCACGTGACTGTGGTGTCTCAGG
TGCCCTGGTTGGAATCATCCCAGTAGGATCCAGGTGGAAAAGCCCTCATGGCCCAGCTAC
CGTTGAGGGCTTAACCCCAACTCCTGGCCCGTAGCCCTGGATGCCTCATGAGACCACCTT
TCCCTCCCCACTCCCACTCCAAAGGCAGGTGCCGAGCCTCTGGAGGTTCTTCCCAGGTT
TTTATCCCTTTTGGGACTTCCTGCCTAGCCCTTCAGAGAGAGTAGTCTACTTACAATCAA

3097
AAAACAAAAAGGTGACCCAACCTGTTTCCAAATTCTCTGGAAAGGGACTTGCCCTCAGGT
GATTTGTGTTCTCAAGGGAAAGGCTGAGTCGGCCCCTCCATCCAGGGAGATGGACTGCCC
ACCACCCTACTCTTGCCTCACTGGGTCCTGGGCCCACCCAGGGCCTGGGCTGAAGACCC
TGTGCATGTGTCCCCAGAGCAGCATGCGCGAGCTGGTGGGGTCAGGCCGCTATGACACGC
AGGAGGACTTCTCTGTGGTGCTGCAGCCCTTCTTCCAGAACATCCAGCTCCCTGTCCTGG
[C,T]
GGTATGTCCCCTGCCCTCGCCCATGGTACTCTTTTAGAGGAAGAAATGCAAGGCAGAATT
GCCAGTTGCTTCCACGAGCATGTGCATAAAATGGGAAAGACACAGCTCTCCAGACGCTG

3116
ACCTGTTTCCAAATTCTCTGGAAAGGGACTTGCCCTCAGGTGATTTGTGTTCTCAAGGGA
AAGGCTGAGTCGGCCCCTCCATCCAGGGAGATGGACTGCCCACCACCCCTACTCTTGCCT
CACTGGGTCCTGGGCCCACCCAGGGCCTGGGCTGAAGACCCTGTGCATGTGTCCCCAGAG
CAGCATGCGCGAGCTGGTGGGGTCAGGCCGCTATGACACGCAGGAGGACTTCTCTGTGGT
GCTGCAGCCCTTCTTCCAGAACATCCAGCTCCCTGTCCTGGTGGTATGTCCCCTGCCCTC
[A,G]
CCCATGGTACTCTTTTAGAGGAAGAAATGCAAGGCAGAATTGCCAGTTGCTTCCACGAGC
ATGTGCATAAAATGGGAAAGACACAGCTCTCCAGACGCTG

4823
AACAAACTACTACACCCGTGTCTCTCTTTTCTTCCCTGATCAGCTTGAACCACTTGGAAG
CAAAACAGAGACCCTGGACCTGAGAGCAGAGATGCCCATCACCTGTCCCACTCAGGTAGT
AGGGGAGGACCTGCCTGGCTCCTCTCCACAAACCAGGGCACACAGCTCGCCCTACCCACT
TCGTCCTCCACCACAGCTTCCTCAGTACCCATCTTGCCCCCTTACTGAGGCCTGAGAGAT
TTGGAGGATGGAGGGGAGTCCATGAGGATGGACAGGGGAGGTGAGAGGGGAGACAAGAGT

```
      [G,A]
      CAGCTGTCATTGGGAACAGGAGATGCAGCAGGGAGAGGAGGCCTGGGCCCCAGCAGAGGG
      AGAGGATCCCGGTGAGAAAAGTGGGCTCCTGAGAGAGGAAATCAGGATGCCAGGAAAATG
      GCAGGAGGGCTTCTCTTAGCAGTGGTGTTTGGGGCAGATGAAAAAATCTGACTGCAGGTT
      AGAGGGCCCAGGCAGGAGCCAGGCAGGCTTAAGAGCTGTGGTTGGAGAGAGGAGAGCCTG
      GATTAGGGAGATTCCACAAGGAAAGGATCACAGAGGACAGCAGCAAAGGGCAGAGCCCAG

4924  CCTGTCCCACTCAGGTAGTAGGGGAGGACCTGCCTGGCTCCTCTCCACAAACCAGGGCAC
      ACAGCTCGCCCTACCCACTTCGTCCTCCACCACAGCTTCCTCAGTACCCATCTTGCCCCC
      TTACTGAGGCCTGAGAGATTTGGAGGATGGAGGGGAGTCCATGAGGATGGACAGGGGAGG
      TGAGAGGGGAGACAAGAGTGCAGCTGTCATTGGGAACAGGAGATGCAGCAGGGAGAGGAG
      GCCTGGGCCCCAGCAGAGGGAGAGGATCCCGGTGAGAAAAGTGGGCTCCTGAGAGAGGAA
      [A,G]
      TCAGGATGCCAGGAAAATGGCAGGAGGGCTTCTCTTAGCAGTGGTGTTTGGGGCAGATGA
      AAAAATCTGACTGCAGGTTAGAGGGCCCAGGCAGGAGCCAGGCAGGCTTAAGAGCTGTGG
      TTGGAGAGAGGAGAGCCTGGATTAGGGAGATTCCACAAGGAAAGGATCACAGAGGACAGC
      AGCAAAGGGCAGAGCCCAGAGCTGTATGGAGGAGGGACGAGGGTGGGCCTACCAGGACAC
      GGCAGCTCCAGGCTCCTTTTAAGGAGGAATCCGTAAGTGGTTGTTAAGCTTGACTTCAGG

4989  TCGCCCTACCCACTTCGTCCTCCACCACAGCTTCCTCAGTACCCATCTTGCCCCCTTACT
      GAGGCCTGAGAGATTTGGAGGATGGAGGGGAGTCCATGAGGATGGACAGGGGAGGTGAGA
      GGGGAGACAAGAGTGCAGCTGTCATTGGGAACAGGAGATGCAGCAGGGAGAGGAGGCCTG
      GGCCCCAGCAGAGGGAGAGGATCCCGGTGAGAAAAGTGGGCTCCTGAGAGAGGAAATCAG
      GATGCCAGGAAAATGGCAGGAGGGCTTCTCTTAGCAGTGGTGTTTGGGGCAGATGAAAAA
      [A,G]
      TCTGACTGCAGGTTAGAGGGCCCAGGCAGGAGCCAGGCAGGCTTAAGAGCTGTGGTTGGA
      GAGAGGAGAGCCTGGATTAGGGAGATTCCACAAGGAAAGGATCACAGAGGACAGCAGCAA
      AGGGCAGAGCCCAGAGCTGTATGGAGGAGGGACGAGGGTGGGCCTACCAGGACACGGCAG
      CTCCAGGCTCCTTTTAAGGAGGAATCCGTAAGTGGTTGTTAAGCTTGACTTCAGGCCTGG
      GGTGGGGGCAGGTTCTCATTGTCTTCAGCTCCTGTTTCTAGGCCCGGTCTTATGGCTTTT

5274  GGGGCAGATGAAAAAATCTGACTGCAGGTTAGAGGGCCCAGGCAGGAGCCAGGCAGGCTT
      AAGAGCTGTGGTTGGAGAGAGGAGAGCCTGGATTAGGGAGATTCCACAAGGAAAGGATCA
      CAGAGGACAGCAGCAAAGGGCAGAGCCCAGAGCTGTATGGAGGAGGGACGAGGGTGGGCC
      TACCAGGACACGGCAGCTCCAGGCTCCTTTTAAGGAGGAATCCGTAAGTGGTTGTTAAGC
      TTGACTTCAGGCCTGGGGTGGGGGCAGGTTCTCATTGTCTTCAGCTCCTGTTTCTAGGCC
      [C,T]
      GGTCTTATGGCTTTTTAACCAAATAAGGCCAAGGCCAGAAAACCCTCAGCAGCAATAAAA
      GCAGAAGGCCTGACCCAATCTGGGAGGCTGGGTTTCCCTCCTAGGTCGGCCACACCACCC
      TCTCCCACCCTCCCTGCTGGGGAATGGACCTGCAGCTCCCCCATGTGTCTGCTGGGAATC
      CTGAGAGAGTGGGCACCCCTGTTCACATGCCTGCTCCCTGTCTGCTGCCTGCCCTACCCC
      AGTCTTGGGCTCAGGCTCAGTCTTGTGTGCCATCAGCCCCATCAGGAGAGCAAGAATGGC

5792  CTGTCTGCTGCCTGCCCTACCCCAGTCTTGGGCTCAGGCTCAGTCTTGTGTGCCATCAGC
      CCCATCAGGAGAGCAAGAATGGCAGGAAGAAGGGATGGGAAGTGAAGACAGTCGTAGCAG
      AGGGCTCAGTTGCTGGGTCTTGTGCTTGGAGCTAAGGAGATTGTCAGATTCTGCAACAGC
      TAGTGCAACACAGATGCCTCTAGTCCAGGTGGTCAGGTGCTGGCCAAAGGCCTGGAGCAA
      AACCTTAGAGGCCCCTACTGTGCCAGGTGTAAACTCTTTAACTGCTTTCCTAAGGATGCC
      [-,T]
      TGGGGGTTCTAGGGGAGCAGCCAGGGACCGTGGATAGTGGGGGCATTTGGGGACTCAGAA
      ATAGCCATATTGTAGATATTTCAATATTTTACCAACCCTATAGCCATACTGAATATCAGC
      CATGGAGGGCCCTTTCCAAACTGTCCACTCCCCTTCCATTACATAACAAAAGCAGCCATC
      ATTTGCTCTTTCTTTCAACAAACGTGTATTGAGTACTGAGTTGGAGCCTAAGCACTGGGT
      CAGGGAGAGCCCTGTCACCCTGGGCTTCGAGGCAACCACTTCCAGGCTTTACCCCAGATC

5871  TGGCAGGAAGAAGGGATGGGAAGTGAAGACAGTCGTAGCAGAGGGCTCAGTTGCTGGGTC
      TTGTGCTTGGAGCTAAGGAGATTGTCAGATTCTGCAACAGCTAGTGCAACACAGATGCCT
      CTAGTCCAGGTGGTCAGGTGCTGGCCAAAGGCCTGGAGCAAAACCTTAGAGGCCCCTACT
      GTGCCAGGTGTAAACTCTTTAACTGCTTTCCTAAGGATGCCTTGGGGGTTCTAGGGGAGC
      AGCCAGGGACCGTGGATAGTGGGGGCATTTGGGGACTCAGAAATAGCCATATTGTAGATA
      [G,T]
      TTCAATATTTTACCAACCCTATAGCCATACTGAATATCAGCCATGGAGGGCCCTTTCCAA
      ACTGTCCACTCCCCTTCCATTACATAACAAAAGCAGCCATCATTTGCTCTTTCTTTCAAC
```

FIGURE 3, page 18 of 33

```
         AAACGTGTATTGAGTACTGAGTTGGAGCCTAAGCACTGGGTCAGGGAGAGCCCTGTCACC
         CTGGGCTTCGAGGCAACCACTTCCAGGCTTTACCCCAGATCAGGCAGAGACCCCCAAAAG
         GAGGCTGCTCCACCCAGCAGCATCTTAAGCTGAGTGGGCTCAGTGCCTCCCTTCTAGACA

6562   CTAAGCAACATTGGAGCCCATTCTGAAAGGGTCCATCTGTTGGCCAGCCCAACTTCACTG
         TGTTCTGAGCATTCTGCATTCCTCAGTCCCATCTGCTCCCTCCCATGTGCCTTGGAGTGA
         TATAAAAGTCCACCAGCATCTCAGTGTGAGCTGACAGGGGCCAGGCAGCACCTATTTTTG
         TCCTAGATGTGTCTAAACATAGAGGCAACAGGCAACAGGCAAGACGCAGTGGGGGGCGGG
         AGGCAGGAGGCCGAGATGGCTGTGAGCATGAGCTTTCTCAGCCTCCTCCCTTCTCCCATC
         [C,T]
         GCAGTCTAACTGCTCATACGTTCTGTGTGCCAGGTAGGGTGACTTAACAGCACGCCATGG
         ATTTCTGTTGTAGTTTCAAGTTGGACAAATTCTTTTACAGACAACTTTTGACTAGCCTTC
         TGTGGACTGAGCCTATACTCTGCCTTAATGGGCTCTGCCCACTCCTTTCCTAACCCCA
         GGGCAGCTGGCTGAACACCTGGTCCTTTTCTTAGGTTTCATTCTTTTTGACCTCTCTGAA
         GCCCTTGTCAAAAGTCACCACCTCCCCCTTGAAATTCACTCCTTCCTGGGTTTGTGGACA

9859   CAATAAACCCAGCTAAAAACAAGCCCAATAAAACCCAATAAAACCCATTAGACAGGAACA
         TAGGAGTTGGAAAAAAAAGAAAAGAAGGGGAGGGGGAAGAAAGCCCTGAGGCACCCCGGC
         TGCCTGTCTGCCACAACCCTGGGCTGTAATTGTTCTTGCCATGGCCTCAGTCTGCAACAC
         ATTCTAGTGTCTCCTTGACCTCTAGCCCTCTAGCTCTGCCTCCCTTTCCCCAACCTGTAG
         ATCTTGTGATCAAATAGATTCAATGAAACACATTGTCCAGTTGC
         [G,A]
         CTCGCAGCACTTCCAAAAAGGTCAAGTTTGTCCTTCCCTCAGTGCCTCCCATTCTGGTCA
         CGGTAGGACTGACTCCAGCCCCTGGACCCTAAGCTGAGTCTGGGCTCCTTTGACGTGCAG
         GGAGAATGCCACTGAGTCTTGTCTCTGAGGACCCTACCTCTCCAAATCTTGCCTCAGTTC
         CTCAGCAGGTACTACACTGACTGGCCATGCCATTCTCTGATGCTTCACTGCCTCAGCTTC
         TCAAGTCTGTCTCCCCACCTGAGCCAATTGTGAGTTTCTCTCTC

9875   CAATAAACCCAGCTAAAAACAAGCCCAATAAAACCCAATAAAACCCATTAGACAGGAACA
         TAGGAGTTGGAAAAAAAAGAAAAGAAGGGGAGGGGGAAGAAAGCCCTGAGGCACCCCGGC
         TGCCTGTCTGCCACAACCCTGGGCTGTAATTGTTCTTGCCATGGCCTCAGTCTGCAACAC
         ATTCTAGTGTCTCCTTGACCTCTAGCCCTCTAGCTCTGCCTCCCTTTCCCCAACCTGTAG
         ATCTTGTGATCAAATAGATTCAATGAAACACATTGTCCAGTTGCACTCGCAGCACTTCCA
         [A,G]
         AAAGGTCAAGTTTGTCCTTCCCTCAGTGCCTCCCATTCTGGTCACGGTAGGACTGACTCC
         AGCCCCTGGACCCTAAGCTGAGTCTGGGCTCCTTTGACGTGCAGGGAGAATGCCACTGAG
         TCTTGTCTCTGAGGACCCTACCTCTCCAAATCTTGCCTCAGTTCCTCAGCAGGTACTACA
         CTGACTGGCCATGCCATTCTCTGATGCTTCACTGCCTCAGCTTCTCAAGTCTGTCTCCCC
         ACCTGAGCCAATTGTGAGTTTCTCTCTCTCCTCCTCTCATCCTGGCACCTAGAAATGCTC

10279   GGGAGAATGCCACTGAGTCTTGTCTCTGAGGACCCTACCTCTCCAAATCTTGCCTCAGTT
         CCTCAGCAGGTACTACACTGACTGGCCATGCCATTCTCTGATGCTTCACTGCCTCAGCTT
         CTCAAGTCTGTCTCCCCACCTGAGCCAATTGTGAGTTTCTCTCTCTCCTCCTCTCATCCT
         GGCACCTAGAAATGCTCTCTAACGCTTGAGCTGCTCAACCAGCATGGGTCACTTGTTTAT
         AGCATGCTCCCAGATCGCCCTCTTTGTTGGTGAATGCTCAGGGAATGCTTACTGTTAACC
         [C,T]
         GAGACAAGCCCAAGTAGCTACATGGACCTGCCACCATAAGCCCTCTCCTGTCTTATGCTG
         TTGTAGAGGGTCCAGGGCTCACTTCTCCCACTTGGCCCTGAGTACCTCTCCTTGAAAGGA
         TGTCAGGGGCTGGGCGCAGTGGCTCACGTCTGTAACCCCAGCACTTTGGGAGGCTGAGGC
         GGGCGGATCACCAGGTCAGGAGATCGAGACCATCCTGGCTAACATGGTGAACCCCCGTC
         TCTACTAAAAATACAAAAAATAAAAATAGCCATTTGTGGTGGCAGGTGCCTGTAGTCCCA

10474   TCTCTAACGCTTGAGCTGCTCAACCAGCATGGGTCACTTGTTTATAGCATGCTCCCAGAT
         CGCCCTCTTTGTTGGTGAATGCTCAGGGAATGCTTACTGTTAACCCGAGACAAGCCCAAG
         TAGCTACATGGACCTGCCACCATAAGCCCTCTCCTGTCTTATGCTGTTGTAGAGGGTCCA
         GGGCTCACTTCTCCCACTTGGCCCTGAGTACCTCTCCTTGAAAGGATGTCAGGGGCTGGG
         CGCAGTGGCTCACGTCTGTAACCCCAGCACTTTGGGAGGCTGAGGCGGGCGGATCACCAG
         [-,G]
         TCAGGAGATCGAGACCATCCTGGCTAACATGGTGAACCCCCGTCTCTACTAAAAATACA
         AAAAATAAAAATAGCCATTTGTGGTGGCAGGTGCCTGTAGTCCCAGCTACTCGGGAGGCT
         GAGGCAGGAAAATGGCATGAACCCAGAAGGCAGAGCTTGCAGTGAGCCGAGATCGCGCCA
         CTGCACTCCAGCCTGGGCAACAGAGCAAGACTCCGTCTCAAAAAAGCAAGCAAGAAAGAA
         AGGATATCGGTTACCTGTTTCAGACAGGAATGCTGAGACCAGGGAAAGGGGAGACTTGTC
```

FIGURE 3, page 19 of 33

10566   CTTACTGTTAACCCGAGACAAGCCCAAGTAGCTACATGGACCTGCCACCATAAGCCCTCT
        CCTGTCTTATGCTGTTGTAGAGGGTCCAGGGCTCACTTCTCCCACTTGGCCCTGAGTACC
        TCTCCTTGAAAGGATGTCAGGGGCTGGGCGCAGTGGCTCACGTCTGTAACCCCAGCACTT
        TGGGAGGCTGAGGCGGGCGGATCACCAGGTCAGGAGATCGAGACCATCCTGGCTAACATG
        GTGAACCCCCGTCTCTACTAAAAATACAAAAAATAAAAATAGCCATTTGTGGTGGCAGG
        [C,T]
        GCCTGTAGTCCCAGCTACTCGGGAGGCTGAGGCAGGAAAATGGCATGAACCCAGAAGGCA
        GAGCTTGCAGTGAGCCGAGATCGCGCCACTGCACTCCAGCCTGGGCAACAGAGCAAGACT
        CCGTCTCAAAAAAGCAAGCAAGAAAGAAAGGATATCGGTTACCTGTTTCAGACAGGAATG
        CTGAGACCAGGGAAAGGGGAGACTTGTCGGGTGCCTCAGGGAACCAGTATCTGAGCTGGG
        GGCTGAGAGCTCTGTGTGGGTGGACTCTGTCCTCCCAGTCGCTGCTGAGTCCCTCTCTTC

12038   CTGGGAATACAGGCATGGGCCACTGTGCCAGCCTGGTTTTTTCTTCTTGTTCCCATTTTA
        TTCTCACATTTTCAGACCATGGGCTTACTACTCCACTGAGCACATTTGTGAGAGTGCTC
        ACAGCCCTGGGCCCGGTTGCTGTTTCCTGATCTCAGTCTTATCAACTTGATCTTGCTTTG
        CTGTCATTTATACATTTTCTCATTAGCTTTCTCCCCATTTCTTCTTTGTCTGCTTCCTTC
        TTCCTTCTTTAACTAACTCCTCACCTGCAACTGGGGGACTTGGATTCTTGACTGGGCTT
        [G,A]
        TGTGAAAACTGATTGTAAAACAGATAGGTAAGTAGGGAATGAGGAGGGTGTTTTACAAGA
        AAAAAAAAATGACTAAGATACAGGAACCCAACCTAAAGAGGAAAAGACATACAGTTCAAA
        GGAGGCAGAAAGAAAAACATTACAGATACTCAAATATATTGATAATCATAACACTTTCTG
        GAAGATTAAAAAAATGCTGAAACATGAATCCCTTGCTAGAGAAATTACAAAGCCAAGAAA
        ATAGATAGGTCTGAGGATTAGGGAGCTGTTCAGTTGCTAGGAGGAACACAAAAGCACAGA

12159   CAGCCCTGGGCCCGGTTGCTGTTTCCTGATCTCAGTCTTATCAACTTGATCTTGCTTTGC
        TGTCATTTATACATTTTCTCATTAGCTTTCTCCCCATTTCTTCTTTGTCTGCTTCCTTCT
        TCCTTCTTTAACTAACTCCTCACCTGCAACTGGGGGACTTGGATTCTTGACTGGGCTTG
        TGTGAAAACTGATTGTAAAACAGATAGGTAAGTAGGGAATGAGGAGGGTGTTTTACAAGA
        AAAAAAAAATGACTAAGATACAGGAACCCAACCTAAAGAGGAAAAGACATACAGTTCAAA
        [G,A]
        GAGGCAGAAAGAAAAACATTACAGATACTCAAATATATTGATAATCATAACACTTTCTGG
        AAGATTAAAAAAATGCTGAAACATGAATCCCTTGCTAGAGAAATTACAAAGCCAAGAAAA
        TAGATAGGTCTGAGGATTAGGGAGCTGTTCAGTTGCTAGGAGGAACACAAAAGCACAGAC
        CCCAGACTACAATGGGTATGAAACCCTCTGCACGCCTTTTGTTGTCCATCCCTTGCCAAA
        GCTGTTATGTAAAACCCTCCGGGGAATGAATGAAATTATGTTTATACAGTTCTTTCTAT

12979   CAAACCATTTCCACCTGCCAGGGGCTCGGGTGTGGTACAGGTTTCAGAGTATTCACTGAA
        GCAGAAATGTACTTCTTACATACTGGGGATTGGAATGTACAGAAAAGGCTCCCGGACCAC
        GAAGCCCCAGGATTGTCCTAACATGTTCTCAAGTTGCTTACCTGACGTCAGCCCCCAAGC
        AGAGGAAGTGTCTATGGATCGATTTTCTTTGACCTTGGCAATCCTGGGCTCACAGACGTG
        GTTACTGCTTAGGCAGCTCAGCCTCTCAAGAGGGAGAGGCAGCTGGTGTGATGTGGCGTT
        [A,G]
        ACTTCTTGGAAGGTGGAGGCTGAGTGGGAGGGAACTACAATTCTGGGGATGGGACCCAAA
        AGGAAGTGGAGGCACGTTGTTCATGTTCCTGTGGGCCCCTAGGCCTTGTTTGGTTCAAGT
        CAATCATTCTAGTGCTGAGGATTCAGAGCCCATGGTTAATTCCATTGGATTAACCATGTC
        TGTGAGCCTAGGACGGCCACTGCAAAGACGGCCTGGAGGACCCCGGACTATACCATGACT
        GGCAGTCAGGCCTGGTCCGGATCAGGTCTGTTGGTCACCAGGATGGGGTTTGACCCGCAG

13865   GGGCTGGGGCAAGGGAGGCAAATTCAGGTGCACCATGCAGGCCAGGCCTTCCTGAGGTGA
        GATTTAAACTGAGACATGCATAATGAGGAGACACTTGCTATACAGGGAGCCAGGAACACA
        GTCCCAGGCAGAAGGACCATGGACCACACAGGCTCAGAAGTGGGACTGTGTTGGGTGTAT
        TTGGGGAAGAGAAAGAAGGTCAGAGTGGCTGGGGGCATGAGAATGAGGTGGAGAGTGGGG
        GAAATGAGATCAGGAGTGCCAAGGAGCCAGATCACACAAAGCCTGAATTACTGAGTAAAA
        [C,A]
        CACTGGATTTCAAGTGGAGAAAGATGGGAAGGCATTGGCGGTCTCAGGAGAGAGTGACAT
        GATCTGGTTCACGTCTTTCAAAGATCTCCCTGACTGCTATGTGTAGAATGGGTTGGCCAT
        CAGCAGGAGTGATTGGGGAAAGACATTTTATAAGCCAGCTGAAGAAACTAACCCATATGA
        AATCATTAAGAACTATTGGATGCTAAGCTCTGGGGTGCAAGCAATACCAGATTGCTGGCT
        GCGGGTTATGCTGTGTCCAGCCTCTCTGAATTTTCTCAGGCTCACGTTAGCCCAGTGGAG

13964   ATACAGGGAGCCAGGAACACAGTCCCAGGCAGAAGGACCATGGACCACACAGGCTCAGAA
        GTGGGACTGTGTTGGGTGTATTTGGGGAAGAGAAAGAAGGTCAGAGTGGCTGGGGGCATG

```
        AGAATGAGGTGGAGAGTGGGGGAAATGAGATCAGGAGTGCCAAGGAGCCAGATCACACAA
        AGCCTCAATTACTGAGTAAAACCACTGGATTTCAAGTGGAGAAAGATGGGAAGGCATTGG
        CGGTCTCAGGAGAGAGTGACATGATCTGGTTCACGTCTTTCAAAGATCTCCCTGACTGCT
        [A,G]
        TGTGTAGAATGGGTTGGCCATCAGCAGGAGTGATTGGGGAAAGACATTTTATAAGCCAGC
        TGAAGAAACTAACCCATATGAAATCATTAAGAACTATTGGATGCTAAGCTCTGGGGTGCA
        AGCAATACCAGATTGCTGGCTGCGGGTTATGCTGTGTCCAGCCTCTCTGAATTTTCTCAG
        GCTCACGTTAGCCCAGTGGAGGCTTGTCCTCATTGAACCAGTGACCAAATTCCCTGAGAA
        TTGAAACGTCAGCTGCATCTTGTGAATCAGGCATTTCTTCATTTATTCATTTACCTATTG

14087   ATGAGGTGGAGAGTGGGGGAAATGAGATCAGGAGTGCCAAGGAGCCAGATCACACAAAGC
        CTGAATTACTGAGTAAAACCACTGGATTTCAAGTGGAGAAAGATGGGAAGGCATTGGCGG
        TCTCAGGAGAGAGTGACATGATCTGGTTCACGTCTTTCAAAGATCTCCCTGACTGCTATG
        TGTAGAATGGGTTGGCCATCAGCAGGAGTGATTGGGGAAAGACATTTTATAAGCCAGCTG
        AAGAAACTAACCCATATGAAATCATTAAGAACTATTGGATGCTAAGCTCTGGGGTGCAAG
        [C,A]
        AATACCAGATTGCTGGCTGCGGGTTATGCTGTGTCCAGCCTCTCTGAATTTTCTCAGGCT
        CACGTTAGCCCAGTGGAGGCTTGTCCTCATTGAACCAGTGACCAAATTCCCTGAGAATTG
        AAACGTCAGCTGCATCTTGTGAATCAGGCATTTCTTCATTTATTCATTTACCTATTGGAT
        GCCTATGTAGAGTGGGCACTGCACTAAGTGCTCGGTAGACAGTGGTGAGCCGAATGGGTC
        TGGATCTGCCCTCTTGGTTCTTCAGTCTCATGCATCTTTGCTTTTGCTGCTGGAAGAGCT

14309   CATTTTATAAGCCAGCTGAAGAAACTAACCCATATGAAATCATTAAGAACTATTGGATGC
        TAAGCTCTGGGGTGCAAGCAATACCAGATTGCTGGCTGCGGGTTATGCTGTGTCCAGCCT
        CTCTGAATTTTCTCAGGCTCACGTTAGCCCAGTGGAGGCTTGTCCTCATTGAACCAGTGA
        CCAAATTCCCTGAGAATTGAAACGTCAGCTGCATCTTGTGAATCAGGCATTTCTTCATTT
        ATTCATTTACCTATTGGATGCCTATGTAGAGTGGGCACTGCACTAAGTGCTCGGTAGACA
        [G,A]
        TGGTGAGCCGAATGGGTCTGGATCTGCCCTCTTGGTTCTTCAGTCTCATGCATCTTTGCT
        TTTGCTGCTGGAAGAGCTAAAAATCCCAGAGCTAGAAGGGCGTGTGTTTGTTTTAACAGC
        TTTCTACTCAAAGTAACCACAGAAACAAAATTCTGTCATCTGAGGTAACGTGAATGAGCC
        TAGAGGACATTACGTTAAGTGAAATAAGTCAGGCACAGAAAGACAAATACTACATGTTCT
        CACCATATGCGGAAGCTTAAGAAGTTGACTTCACAGAAGTAGAGTATAAATAGTGGTTAT

16028   ATATGCAAAAAGACATACAGGTATCCAGAAAAGACAGGCAGAAACCAGGAGCTTTACAAT
        TTTAAAATATTTTGTGTTATTATTCTAAAAATATTTTAATTATTGTCTAGGTTCTACCAT
        TATAATTAGTGTCAGTTAGCTTAATTTTATAAAACACACATACCTGTAATCTCATGTTAG
        GCATCCAAATGCTGTGTTCCTTTGGGAGACCCACCTGTGTAGGACTTCATGGTTTTCTTC
        CCTGCTTTGGGGCAGCCACTGGCTCCATTCAAAGCATAGATATATGGGGATAAGAAAGGT
        [G,T]
        GTGTGTGGGTGCACATGTGGAGACATGCACTATGGGTTGTGCATAGGGGTAGCTAGACAC
        ACCCATTTCTCCCCCTTTAATTTCCCTCCTAGCCCACCTATAACTCACAGTTCTTTCCCT
        CACATGATCCTGTATGGTGACTCATTTCTAGCCTCCATCAAAAATCCCTTAGCTGGTTCT
        TCTTGGGCTGAAGCTTATCTCCCTGCACAATGAGTGTTGGGCACTGAATCTTTTCTCCTG
        TTGATTTAGAACTGGGGCAGTGACTTCCTGTGTACAGAGTGGAAGGCTTCCAATAGTGTT

16375   GGGTAGCTAGACACACCCATTTCTCCCCCTTTAATTTCCCTCCTAGCCCACCTATAACTC
        ACAGTTCTTTCCCTCACATGATCCTGTATGGTGACTCATTTCTAGCCTCCATCAAAAATC
        CCTTAGCTGGTTCTTCTTGGGCTGAAGCTTATCTCCCTGCACAATGAGTGTTGGGCACTG
        AATCTTTTCTCCTGTTGATTTAGAACTGGGGCAGTGACTTCCTGTGTACAGAGTGGAAGG
        CTTCCAATAGTGTTCCAACCTCTGGTGAGTGAAAACATCATCATCTCCTTCAATTAAGGG
        [C,T]
        CTTGCCGAATATCAGGTTGTGGGGAGACCCTGCAAACATACCCTGGAGCTTTAAGCAGGA
        CTTGCTAATTCCCCTGCAGTGCAGACCTAGATCCTGCGGCCTGCCGCCACAGCTGGGCTT
        CCATGTGGAGGTGCACAGAGCTCTCCATTGGATGCTACTTCTTGTCTCCTTATAGTCCCA
        GTGGCAGTCCCTTAGGCCTCCCTGCCCAGTGAGGCAGGTAGAGTCAGGGATTGGGATCTA
        CCTGCCTGTGCTACATGACCCTGCAGCTGGAACTTTCCTGGACCACCCCAATGTCAATCA

16705   CTGCAAACATACCCTGGAGCTTTAAGCAGGACTTGCTAATTCCCCTGCAGTGCAGACCTA
        GATCCTGCGGCCTGCCGCCACAGCTGGGCTTCCATGTGGAGGTGCACAGAGCTCTCCATT
        GGATGCTACTTCTTGTCTCCTTATAGTCCCAGTGGCAGTCCCTTAGGCCTCCCTGCCCAG
        TGAGGCAGGTAGAGTCAGGGATTGGGATCTACCTGCCTGTGCTACATGACCCTGCAGCTG
        GAACTTTCCTGGACCACCCCAATGTCAATCAGGCTCTTCTGAGGGTGGATGATAGCCATG
```

FIGURE 3, page 21 of 33

```
              [G,A]
              AACCCATTCCCTGCAGTGCCTTGGTTGGTCTGAATGAATGGGAGGGGCAAAACTGCTAAA
              GCCTTAAGCTGAAAATAAGTACAATGGGGAGCAGTGGGACAGAGTTATAGACTTCTGGTA
              AAATGTGTACTTTAAGAGGTAGATACCCCCAGCCCCCACAACCACCTCTCTGCTTGTCTC
              CCCTAGTCCACCAGCTCCGACCAGCAGACATCAAAGTGGTGGCCGCCCTGGGTGACTCTC
              TGACTGTGAGTAGTGAGCCATGAACCAGGATGGGCAGCTCAGAGTCCAGCCAGGCCCTGC

19708     CCTGCTGGAGGAGGGGAAGAGGAGGTTATCTGCAAGAAGGGAAGTCAGCCAGCCCTGAAA
              AGCCCCAGACTTCCTGTGTCCCACCCATGTCCCCACCCTGCATGCTCATCTCAGTTACTG
              TGAGGGTCCTGCAGGCTCTCACCTGTGCTCTTCTCCTCCTCCTCCTCTAAAGACATT
              CTGAAGAAGTTCAACCCTTACCTCCTTGGCTTCTCTACCAGCACCTGGGAGGGGACAGCA
              GGACTAAATGTGGCAGCGGAAGGGGCCAGAGCTAGGTGAGTAGATGCCGTACAGGAGGGC
              [G,C]
              AG

21406     AAGAATGAATCTCCATCTCCAAAAATAATAATAATTAAAAATAAATAAAAGATACAAAGG
              AATCAAAAGATGAACTCCCTGGCCACGAAGAGCTTGCACTCTAGGTAAGGAGGCTAAACA
              AATGGGAAATAACTTTCTGAAAAAGACAATGCTGGGTATGGCAACAATGCAGTGCTTCGC
              ATGGAGTACAATTAAGAGAACAGAAGAGCACACAGTATGAACTGCACTGTCTAAAGACAG
              ATGCAGACCCAGAAGGGACCCCTGAAATCATCCAGTCCAACCTCTTCCTTTAAAAGATGG
              [G,A]
              AAAAGTCAATCCTAGCAAGATTCAGCAACTTGTACAAGCTCAACAGCAAGTTGGTAGCAG
              AGCTGAAAGTAGAACCACTGGTCCCTGGGGTAAAAAAGGAAATGCAAGATGTGTGGATCA
              GGGAGCCCAGAGAGGAGGCTCAAGGGAAAGTAGGACTTGGTCTGGGCCTGAAGGATGGGA
              AGAAGATGGCTAGGAAGAGGGGAAGAAGCGGCATTTGTAACTTCCCCTCCTACCCACGAG
              GGCTTATTGCCCATGGATTCTCTTAGTCACACCTTGAACCTGTTAAAAGGTTAAAGGCAC

22401     AGGCCAAGGTAGGCAGATTGCCCAGGAGTTGGGAGACCAGTCTGAGCAACTTGGTGAAACC
              CTGTCTCTACCAAAAATACAAAAAATTAGCCGGGCATGGTGGCATGGACCTGTAGTCCCA
              GCTACTCGGAAGGCTGAGATGGGAGGATCACTTGAGCTCAGAGGGGTTGAGGCTGCAGTG
              AGCCGTGATCACACCACTACACTCCAGCCTGGGCAACAGAGCAAGACCCTGTCTCAAAAA
              GGATACAATTTAACATTGTACCTGTGAAATCATCACCACAATCAAGATGAAAAATGTGTT
              [T,C]
              ATCACCCACAGGAGTTTTCTCAGGCCCCTTGGTAATCTCTCCCTCCTGCTCCTTCCTGTC
              CCTACCTCACACCCCAGGCAACCACTAACCTTCTTTCCATCACAATAGATTAGTTTGCAT
              TTTTAAAAATTTTATATAAATGGGATCAAAGAGTATATACTTTTTATCTGACTTATTTAG
              CAAAATGATTTTGCGATGCATCCATGTTATTCGGTATACCAATAGTTCGTCCCTTTTTAT
              GGCTGAGTGTAGTGTTCCGTTGGCATTCATATCGCTCATCCAGAACACCAAATGGTATTG

22926     GTTCGTCCCTTTTTATGGCTGAGTGTAGTGTTCCGTTGGCATTCATATCGCTCATCCAGA
              ACACCAAATGGTATTGTTTTTATTTATGGCAGACATCAGGGGATGAAGGGAGAACTAATCC
              TGTCCATCCTGGTTTATTGGAGAGGGAGAAAAAAAAAAGTGAGGAGATGGGGAATGGTGC
              GGAAATCTAAGTAACCACAGAAAAGAAAAACAAAAGGATTAAAGGAGCAGAGAGCAGGGC
              TTAGAAGTAAAGGTTAAAGGAGTCATTAAGCCTGGAAAGGAGAAAACTGAGGGATAATTG
              [A,T]
              GAGCTGTGACTTTTCTCAAATATACAAAAGGTTATTTTTAAAACAGGCAACTGAAGAAGA
              AATGAACAGGCTTGGCTTACGAAGAAAGAGCTTGAGGAAGTATAAGGGAAAGTCCCTGAG
              GGGAGGCTTGACGGGATCCCAACCCGAGTGGCCGATGAGACTATTGGGTGGCAGGGGCTA
              GATCAATGTGGCTCCAGGGTCCAGGGCAGCCATGTGATTGTTACTAAGCTGAGATTTCTT
              GAGAATGGAATGACCTTTGTACTGGTAACATCATTCTTCTTGAAACACCTCTCTTCCTAG

23007     TTTATGGCAGACATCAGGGGATGAAGGGAGAACTAATCCTGTCCATCCTGGTTTATTGGA
              GAGGGAGAAAAAAAAAAGTGAGGAGATGGGGAATGGTGCGGAAATCTAAGTAACCACAGA
              AAAGAAAAACAAAAGGATTAAAGGAGCAGAGAGCAGGGCTTAGAAGTAAAGGTTAAAGGA
              GTCATTAAGCCTGGAAAGGAGAAAACTGAGGGATAATTGTGAGCTGTGACTTTTCTCAAA
              TATACAAAAGGTTATTTTTAAAACAGGCAACTGAAGAAGAAATGAACAGGCTTGGCTTAC
              [G,A]
              AAGAAAGAGCTTGAGGAAGTATAAGGGAAAGTCCCTGAGGGGAGGCTTGACGGGATCCCA
              ACCCGAGTGGCCGATGAGACTATTGGGTGGCAGGGGCTAGATCAATGTGGCTCCAGGGTC
              CAGGGCAGCCATGTGATTGTTACTAAGCTGAGATTTCTTGAGAATGGAATGACCTTTGTA
              CTGGTAACATCATTCTTCTTGAAACACCTCTCTTCCTAGGCCAAAATCCCATGTCGTGAG
              TCCTCGCTCCTGAGCCGGCACTAACGCCCCTCTCTCTACCCCCCACCTAGGGACATGCCA
```

FIGURE 3, page 22 of 33

23180    TAAAGGAGTCATTAAGCCTGGAAAGGAGAAAACTGAGGGATAATTGTGAGCTGTGACTTT
         TCTCAAATATACAAAAGGTTATTTTTAAAACAGGCAACTGAAGAAGAAATGAACAGGCTT
         GGCTTACGAAGAAAGAGCTTGAGGAAGTATAAGGGAAAGTCCCTGAGGGGAGGCTTGACG
         GGATCCCAACCCGAGTGGCCGATGAGACTATTGGGTCGGCAGGGGCTAGATCAATGTGGCT
         CCAGGGTCCAGGGCAGCCATGTGATTGTTACTAAGCTGAGATTTCTTGAGAATGGAATGA
         [C,G]
         CTTTGTACTGGTAACATCATTCTTCTTGAAACACCTCTCTTCCTAGGCCAAAATCCCATG
         TCGTGAGTCCTCGCTCCTGAGCCGGCACTAACGCCCCTCTCTCTACCCCCCACCTAGGGA
         CATGCCAGCCCAGGCCTGGGACCTGGTAGAGCGAATGAAAAACAGCCCCGTGAGTACAGG
         CCCCCAGGCCACCCCTGAAAGGTGCCCATCTCCTGCTGGCTGGGGAGGGGACAGCCCCAT
         AAGGGTCCCTCTCACCACAGCACTTCCTGCTTTGGGCTAGCCAAAAGATCCTCGGAGAAG

26490    CTCCCTCTGCTATAAAGCAAAGCCCTGAGATTCAGCCTGCAAGGACTTACTGAGCACCTA
         CTATGTACCTTGTTTGCATCACCCAGGATGCTGTGGACACACCTCTAAATCAGCCTCCTA
         CTGGGGAGATGGTTCAGAGGAAGAGAACCTTACACTGAGTCACAGGGGATAGAAGTTAGG
         GGAACACAGGAGAGCAAAACATTTCAGGCAGTGGGACCAGCATGGACCAAAGCCCAAACG
         AAAAAGGAAGTGTGGCCACCCAGGGCATGGCAAGGGGCTGGAGAAGGCTGAGGTCAGATG
         [A,G]
         CGGATGGGACTGCCAAGAGCCAAGGCCAAAAAGTGGCAGGACCCAGCACTGGCAGAGTCC
         ACTGTTGGGTCTGAGATTATGTAGAGCAGGGTGGGGGTTGGGATTGTTCATGGTGTCTAG
         TAGGGGACAAGGGATGATTCCTTACAGAGACTCAGCAGCAACAAGAACTGGGCTTCTCAG
         TTTGACCAGGACCACCGAAGCCCCTCTGTACCCACTCAGTCATTTAGCCCAGGCCCCAGA
         GCCCTCCTATGCTCTTGCCATTCTCTCAGAGCGGGCACCAGGGGCTAAAGAGAGTACCCT

26505    AGCAAAGCCCTGAGATTCAGCCTGCAAGGACTTACTGAGCACCTACTATGTACCTTGTTT
         GCATCACCCAGGATGCTGTGGACACACCTCTAAATCAGCCTCCTACTGGGGAGATGGTTC
         AGAGGAAGAGAACCTTACACTGAGTCACAGGGGATAGAAGTTAGGGGAACACAGGAGAGC
         AAAACATTTCAGGCAGTGGGACCAGCATGGACCAAAGCCCAAAGGAAAAAGGAAGTGTGG
         CCACCCAGGGCATGGCAAGGGCTGGAGAAGGCTGAGGTCAGATGACGGATGGGACTGCC
         [A,G]
         AGAGCCAAGGCCAAAAAGTGGCAGGACCCAGCACTGGCAGAGTCCACTGTTGGGTCTGAG
         ATTATGTAGAGCAGGGTGGGGGTTGGGATTGTTCATGGTGTCTAGTAGGGGACAAGGGAT
         GATTCCTTACAGAGACTCAGCAGCAACAAGAACTGGGCTTCTCAGTTTGACCAGGACCAC
         CGAAGCCCCTCTGTACCCACTCAGTCATTTAGCCCAGGCCCCAGAGCCCTCCTATGCTCT
         TGCCATTCTCTCAGAGCGGGCACCAGGGGCTAAAGAGAGTACCCTTTTTTCCTTACAGGA

29336    AAATACTTACCCCTGCAAATTGAACACCAAGGCCAGGGAAGGGAGTGAGAGACCCCAAAG
         TGGAAGCTGAGAAAATCCCCTTCTCCCAGCGGGTAGGCAGCAAGAGATTCCCAGAGTAGA
         CTCCTTGTGGTAGGGCCCATTCCCCACCCAGAGCCATGTGTAATAATTACTACTCACTTC
         CTCCCCTCCCTTCATTAAAAACAAAAGGCTTAGGCCCGACACAATGGCTCACGTCTGGTG
         TCCCAGCTACTCAGGAGGCTGAGATGGGAGGACAGCTTGAGCCCAGGAGTTGGAGGCTGC
         [T,C]
         GTTAGCTATGATGATGCCATTGTACTCTGCCTAGACAACAGCGTGAGACCCTATCTCAAA
         AAAAAAAAAAGAAAAAAAGAAAAAGGCTTAGCCCTGCCCTACTTAACTCTACCTCAAAT
         TCTCCTTGCCCTCTCTCTGCCCCCTTCCATCTCCCCACCTCCACTCCTGCTTATGTCTCT
         GCCTCTATTGTTCCCTCTCAGGCTCAGGTAGCATTTCCATTCTGCAAACTGACCCTCCTT
         CATTCACAAGGCAAGTCTGCTTCCCTCCTCTAAGGAGCTTCCCCTGCCTGAACTTCACCC

29829    CCCTCTCAGGCTCAGGTAGCATTTCCATTCTGCAAACTGACCCTCCTTCATTCACAAGGC
         AAGTCTGCTTCCCTCCTCTAAGGAGCTTCCCCTGCCTGAACTTCACCCGCGGACATCTCC
         CCATATCACATTCAGTCTGTACTTGATGGGCCCTAAAAGCCCCAAAGGGTTCTCATGTTT
         TCACATCTTGGCTCATTTTTCCAGATGGATGATAAACTCCTTGAAGATAAGTACATCTAG
         TCTGTTCCTTTTACATTCCATGCTTGGGTACTTAAATCCAGCCACCGTGGACTCTCCTCC
         [C,T]
         GCAAAGTTCATGGGCATTTTGGGCAGCTGGTGTTGAGATGCTCCCCATCTGACCTGCAGCC
         CCATGTTCTAATTGACCTCTTCGTGCAGTGAGAGGAGGGGAGGACTTTGGCCTATGCAAT
         CTGGTCAGTGGCTCAGACCCAGCCTTTCAGGCAGAGGCTTTGGAATGGGACTGGGTGGAG
         CTGTGTAGCTAGGGAGCTTCTCCCACCAGGAGCCGCTGGGTTCAACTCATCTCTGATCCT
         GAGAACCAGCATAGGGCTTTGAAATGTCCGTGCCCATGAATGGGTGGAGAATAAAAGTAT

29830    CCTCTCAGGCTCAGGTAGCATTTCCATTCTGCAAACTGACCCTCCTTCATTCACAAGGCA
         AGTCTGCTTCCCTCCTCTAAGGAGCTTCCCCTGCCTGAACTTCACCCGCGGACATCTCCC
         CATATCACATTCAGTCTGTACTTGATGGGCCCTAAAAGCCCCAAAGGGTTCTCATGTTTT

FIGURE 3, page 23 of 33

```
        CACATCTTGGCTCATTTTTCCAGATGGATGATAAACTCCTTGAAGATAAGTACATCTAGT
        CTGTTCCTTTTACATTCCATGCTTGGGTACTTAAATCCAGCCACCGTGGACTCTCCTCCC
        [G,T]
        CAAAGTTCATGGGCATTTTGGGAGCTGGTGTTGAGATGCTCCCCATCTGACCTGCAGCCC
        CATGTTCTAATTGACCTCTTCGTGCAGTGAGAGGAGGGGAGGACTTTGGCCTATGCAATC
        TGGTCAGTGGCTCAGACCCAGCCTTTCAGGCAGAGGCTTTGGAATGGGACTGGGTGGAGC
        TGTGTAGCTAGGGAGCTTCTCCCACCAGGAGCCGCTGGGTTCAACTCATCTCTGATCCTG
        AGAACCAGCATAGGGCTTTGAAATGTCCGTGCCCATGAATGGGTGGAGAATAAAAGTATG

29840   TCAGGTAGCATTTCCATTCTGCAAACTGACCCTCCTTCATTCACAAGGCAAGTCTGCTTC
        CCTCCTCTAAGGAGCTTCCCCTGCCTGAACTTCACCCGCGGACATCTCCCCATATCACAT
        TCAGTCTGTACTTGATGGGCCCTAAAAGCCCCAAAGGGTTCTCATGTTTTCACATCTTGG
        CTCATTTTTCCAGATGGATGATAAACTCCTTGAAGATAAGTACATCTAGTCTGTTCCTTT
        TACATTCCATGCTTGGGTACTTAAATCCAGCCACCGTGGACTCTCCTCCCCGCAAAGTTCA
        [C,T]
        GGGCATTTTGGGAGCTGGTGTTGAGATGCTCCCCATCTGACCTGCAGCCCCATGTTCTAA
        TTGACCTCTTCGTGCAGTGAGAGGAGGGGAGGACTTTGGCCTATGCAATCTGGTCAGTGG
        CTCAGACCCAGCCTTTCAGGCAGAGGCTTTGGAATGGGACTGGGTGGAGCTGTGTAGCTA
        GGGAGCTTCTCCCACCAGGAGCCGCTGGGTTCAACTCATCTCTGATCCTGAGAACCAGCA
        TAGGGCTTTGAAATGTCCGTGCCCATGAATGGGTGGAGAATAAAAGTATGTTTGCATCCC

29944   TCTCCCCATATCACATTCAGTCTGTACTTGATGGGCCCTAAAAGCCCCAAAGGGTTCTCA
        TGTTTTCACATCTTGGCTCATTTTTCCAGATGGATGATAAACTCCTTGAAGATAAGTACA
        TCTAGTCTGTTCCTTTTACATTCCATGCTTGGGTACTTAAATCCAGCCACCGTGGACTCT
        CCTCCCGCAAAGTTCATGGGCATTTTGGGAGCTGGTGTTGAGATGCTCCCCATCTGACCT
        GCAGCCCCATGTTCTAATTGACCTCTTCGTGCAGTGAGAGGAGGGGAGGACTTTGGCCTA
        [C,T]
        GCAATCTGGTCAGTGGCTCAGACCCAGCCTTTCAGGCAGAGGCTTTGGAATGGGACTGGG
        TGGAGCTGTGTAGCTAGGGAGCTTCTCCCACCAGGAGCCGCTGGGTTCAACTCATCTCTG
        ATCCTGAGAACCAGCATAGGGCTTTGAAATGTCCGTGCCCATGAATGGGTGGAGAATAAA
        AGTATGTTTGCATCCCACTAGAGTAGCCCCTTAAAGTCACTGTCCTTTAGGGTGAGTTGA
        CTCCCGTCAACAACCAATCCAAGGCAGCAGGACTGGACCCTGTCTGTGCAGCCTTGCCAG

30468   CCTTTAGGGTGAGTTGACTCCCGTCAACAACCAATCCAAGGCAGCAGGACTGGACCCTGT
        CTGTGCAGCCTTGCCAGGAGGGTTGAGCAGCTTCTCTCTCTGTCCCCAGCATGGCATCTC
        CAGTTTCTCCTACTGGCACCAATACACACAGCGTGAGGACTTTGCGGTTGTGGTGCAGCC
        TTTCTTCCAAAACACACTCACCCCACTGAACGAGGTGAGCTGCAGGTATTTTAGGGAGGC
        TCACGTATGGGGGCCTTATCACAGACGATGGATGTATTTCCTTCTCTAAGTGGGCTTTTT
        [T,-]
        TTTTTTTTAACCATCTCTCTCCAAGAGGATTCCTGAGGGTGGCTTTTTCCACATTACCTC
        CTTTTTGTGGGGGCTGGGCTGTGATTGGAACTCAGATGTACTTTGAAAGGAAATCAATAG
        TGACTAAGCTCCCAGGCCTGGCCCTGATGTTTTCTGGATTGGGATAGAATGGAAAGCTTC
        CTAAAAATGTTACTCTTTTCAACTCTTAGGATAGGGGTGCTGAAAGAAAAGGGAGAGACT
        ATGGGTGGGTCCAATTCTTGTCTGTTTAAAAAGAAAATTCCGGCCGGGTGCAGTGGCTCA

30471   TTAGGGTGAGTTGACTCCCGTCAACAACCAATCCAAGGCAGCAGGACTGGACCCTGTCTG
        TGCAGCCTTGCCAGGAGGGTTGAGCAGCTTCTCTCTCTGTCCCCAGCATGGCATCTCCAG
        TTTCTCCTACTGGCACCAATACACACAGCGTGAGGACTTTGCGGTTGTGGTGCAGCCTTT
        CTTCCAAAACACACTCACCCCACTGAACGAGGTGAGCTGCAGGTATTTTAGGGAGGCTCA
        CGTATGGGGGCCTTATCACAGACGATGGATGTATTTCCTTCTCTAAGTGGGCTTTTTTTT
        [T,-]
        TTTTTAACCATCTCTCTCCAAGAGGATTCCTGAGGGTGGCTTTTTCCACATTACCTCCTT
        TTTGTGGGGGCTGGGCTGTGATTGGAACTCAGATGTACTTTGAAAGGAAATCAATAGTGA
        CTAAGCTCCCAGGCCTGGCCCTGATGTTTTCTGGATTGGGATAGAATGGAAAGCTTCCTA
        AAAATGTTACTCTTTTCAACTCTTAGGATAGGGGTGCTGAAAGAAAAGGGAGAGACTATG
        GGTGGGTCCAATTCTTGTCTGTTTAAAAAGAAAATTCCGGCCGGGTGCAGTGGCTCATGC

30802   TGAGGGTGGCTTTTTCCACATTACCTCCTTTTTGTGGGGGCTGGGCTGTGATTGGAACTC
        AGATGTACTTTGAAAGGAAATCAATAGTGACTAAGCTCCCAGGCCTGGCCCTGATGTTTT
        CTGGATTGGGATAGAATGGAAAGCTTCCTAAAAATGTTACTCTTTTCAACTCTTAGGATA
        GGGGTGCTGAAAGAAAAGGGAGAGACTATGGGTGGGTCCAATTCTTGTCTGTTTAAAAAG
        AAAATTCCGGCCGGGTGCAGTGGCTCATGCCTGTAATCTCAGCCTTTGGGAAGCCAAGGC
        [G,A]
```

FIGURE 3, page 24 of 33

```
           GTTGAATCACGAGGTTAGGAGTTTGAGACCAGCCTGGCCAACATGGTGAAACCCCGTTTC
           TACTAAAAATACAAAAAGTTAGCTGGGCGTGGTGGCAGGCACCTGTAATCCCAGGTACTC
           GGGAGGCAGAAGTTGCAGTGAGCTGAGATTATGCCACTGCACTCCAGCCTGGCTGACAGT
           GCGAAACTCCGTCTCAAAAAAAAAGAAAAAAGAAAAAAAGAAATTCTAAATTCTGGGAGT
           TTTTCCATCAGTATCTGAGCAAGTTGGCAGGAAAGTTGAAAGAATGAAAGGAGACATGCC

30894      AAGCTCCCAGGCCTGGCCCTGATGTTTTCTGGATTGGGATAGAATGGAAAGCTTCCTAAA
           AATGTTACTCTTTTCAACTCTTAGGATAGGGGTGCTGAAAGAAAAGGGAGAGACTATGGG
           TGGGTCCAATTCTTGTCTGTTTAAAAAGAAAATTCCGGCCGGGTGCAGTGGCTCATGCCT
           GTAATCTCAGCCTTTGGGAAGCCAAGGCGGTTGAATCACGAGGTTAGGAGTTTGAGACCA
           GCCTGGCCAACATGGTGAAACCCCGTTTCTACTAAAAATACAAAAAGTTAGCTGGGCGTG
           [G,A]
           TGGCAGGCACCTGTAATCCCAGGTACTCGGGAGGCAGAAGTTGCAGTGAGCTGAGATTAT
           GCCACTGCACTCCAGCCTGGCTGACAGTGCGAAACTCCGTCTCAAAAAAAAAGAAAAAAG
           AAAAAAAGAAATTCTAAATTCTGGGAGTTTTTTCCATCAGTATCTGAGCAAGTTGGCAGGA
           AAGTTGAAAGAATGAAAGGAGACATGCCCAGGGCACCTGCTGGGAGAGTGAGTGGGGCTC
           AGGTAGCAGAGCCCTTTCCCAGGATGATAACCTCCTTGCCGTTGGTTGCAGAGAGGGGAC

30907      TGGCCCTGATGTTTTCTGGATTGGGATAGAATGGAAAGCTTCCTAAAAATGTTACTCTTT
           TCAACTCTTAGGATAGGGGTGCTGAAAGAAAAGGGAGAGACTATGGGTGGGTCCAATTCT
           TGTCTGTTTAAAAAGAAAATTCCGGCCGGGTGCAGTGGCTCATGCCTGTAATCTCAGCCT
           TTGGGAAGCCAAGGCGGTTGAATCACGAGGTTAGGAGTTTGAGACCAGCCTGGCCAACAT
           GGTGAAACCCCGTTTCTACTAAAAATACAAAAAGTTAGCTGGGCGTGGTGGCAGGCACCT
           [G,A]
           TAATCCCAGGTACTCGGGAGGCAGAAGTTGCAGTGAGCTGAGATTATGCCACTGCACTCC
           AGCCTGGCTGACAGTGCGAAACTCCGTCTCAAAAAAAAAGAAAAAAGAAAAAAAGAAATT
           CTAAATTCTGGGAGTTTTTCCATCAGTATCTGAGCAAGTTGGCAGGAAAGTTGAAAGAAT
           GAAAGGAGACATGCCCAGGGCACCTGCTGGGAGAGTGAGTGGGGCTCAGGTAGCAGAGCC
           CTTTCCCAGGATGATAACCTCCTTGCCGTTGGTTGCAGAGAGGGGACACTGACCTCACCT

31447      CCTTTCCCAGGATGATAACCTCCTTGCCGTTGGTTGCAGAGAGGGGACACTGACCTCACC
           TTCTTCTCCGAGGACTGTTTTCACTTCTCAGACCGCGGGCATGCCGAGATGGCCATCGCA
           CTCTGGAACAACATGGTGAGCAGCCAAGGGCCTGGTGGGCCTTGTCAAGGGGGGATCTAA
           GGATATTGACACTCTGTCTCACAATGGCAAAACTACTGGAGACATGGCTCCTTTCTCCCC
           AAAGCCCAAAGTGGCAGCACACCTTATTGGTCCTGATAGATTAATTCCAAAGGGAAAATA
           [C,A]
           CCTATATTTATCCAACACCCTTTGAAAGTTATACAAACACACACTCACACAACTTTATTC
           TTTGTTCCTTCAGCAATGCCCAGGTACTGCGAGGGGATCCCTTTGTAATCAGATAGGTTG
           GCTAGATGAAAATACCAACTTCTACCTCGTACTGTGTGACCTTGGGCAAACGATCTCTCT
           GGCCACCTGTATCAACATCTATAAAACAGTGAAAACAAGACAGGTCTCAGACAACGCATT
           GAGATCATGTGTACATGGCACCTAGCACAATAGTTAGCACTCAGCAAATGTCACCACCAT

31603      GGGCCTTGTCAAGGGGGGATCTAAGGATATTGACACTCTGTCTCACAATGGCAAAACTAC
           TGGAGACATGGCTCCTTTCTCCCCAAAGCCCAAAGTGGCAGCACACCTTATTGGTCCTGA
           TAGATTAATTCCAAAGGGAAAATACCCTATATTTATCCAACACCCTTTGAAAGTTATACA
           AACACACACTCACACAACTTTATTCTTTGTTCCTTCAGCAATGCCCAGGTACTGCGAGGG
           GATCCCTTTGTAATCAGATAGGTTGGCTAGATGAAAATACCAACTTCTACCTCGTACTGT
           [G,A]
           TGACCTTGGGCAAACGATCTCTCTGGCCACCTGTATCAACATCTATAAAACAGTGAAAAC
           AAGACAGGTCTCAGACAACGCATTGAGATCATGTGTACATGGCACCTAGCACAATAGTTA
           GCACTCAGCAAATGTCACCACCATCAGCCTTCCAAGCACTCCGGGCTCAACTCATACCCA
           ACTCATTTCTCTAAACATCGAAAGTGGAGATCCACACAGCCTGTTTTCCGAGGCTGATA
           CCTATTCCAGTCCTTTCTGATGGGAAGAAGGGACCTTATGAAATGAACATACAGTCTGGG

31685      CCAAAGCCCAAAGTGGCAGCACACCTTATTGGTCCTGATAGATTAATTCCAAAGGGAAAA
           TACCCTATATTTATCCAACACCCTTTGAAAGTTATACAAACACACACTCACACAACTTTA
           TTCTTTGTTCCTTCAGCAATGCCCAGGTACTGCGAGGGGATCCCTTTGTAATCAGATAGG
           TTGGCTAGATGAAAATACCAACTTCTACCTCGTACTGTGTGACCTTGGGCAAACGATCTC
           TCTGGCCACCTGTATCAACATCTATAAAACAGTGAAAACAAGACAGGTCTCAGACAACGC
           [A,G]
           TTGAGATCATGTGTACATGGCACCTAGCACAATAGTTAGCACTCAGCAAATGTCACCACC
           ATCAGCCTTCCAAGCACTCCGGGCTCAACTCATACCCAACTCATTTCTCTAAACATCGAA
           AAGTGGAGATCCACACAGCCTGTTTTCCGAGGCTGATACCTATTCCAGTCCTTTCTGATG
```

FIGURE 3, page 25 of 33

```
              GGAAGAAGGGACCTTATGAAATGAACATACAGTCTGGGGGTCTTTCAGGGACACCTGCCT
              GGTGCTTCCACTCTGCCTTCTGTGGCTGGCCACCAGCAACTGAACGGTTTCCGCACAGCA

31833         ACTGCGAGGGGATCCCTTTGTAATCAGATAGGTTGGCTAGATGAAAATACCAACTTCTAC
              CTCGTACTGTGTGACCTTGGGCAAACGATCTCTCTGGCCACCTGTATCAACATCTATAAA
              ACAGTGAAAACAAGACAGGTCTCAGACAACGCATTGAGATCATGTGTACATGGCACCTAG
              CACAATAGTTAGCACTCAGCAAATGTCACCACCATCAGCCTTCCAAGCACTCCGGGCTCA
              ACTCATACCCAACTCATTTCTCTAAACATCGAAAAGTGGAGATCCACACAGCCTGTTTTC
              [C,T]
              GAGGCTGATACCTATTCCAGTCCTTTCTGATGGGAAGAAGGGACCTTATGAAATGAACAT
              ACAGTCTGGGGGTCTTTCAGGGACACCTGCCTGGTGCTTCCACTCTGCCTTCTGTGGCTG
              GCCACCAGCAACTGAACGGTTTCCGCACAGCACTTGACCTGTCACCCCCAACAACTGGAT
              CCTCTTGCACGGAGCAAATGAAATGCCTTCCCAACCCAATGGTTTCTTTTAATCCAGGCT
              CAGTGGGTAACACAATCCCCACCCCAACCTGTATGTTCCCTCCTTTGTCCTATGACAACT

31970         GGTCTCAGACAACGCATTGAGATCATGTGTACATGGCACCTAGCACAATAGTTAGCACTC
              AGCAAATGTCACCACCATCAGCCTTCCAAGCACTCCGGGCTCAACTCATACCCAACTCAT
              TTCTCTAAACATCGAAAAGTGGAGATCCACACAGCCTGTTTTCCGAGGCTGATACCTATT
              CCAGTCCTTTCTGATGGGAAGAAGGGACCTTATGAAATGAACATACAGTCTGGGGGTCTT
              TCAGGGACACCTGCCTGGTGCTTCCACTCTGCCTTCTGTGGCTGGCCACCAGCAACTGAA
              [C,T]
              GGTTTCCGCACAGCACTTGACCTGTCACCCCCAACAACTGGATCCTCTTGCACGGAGCAA
              ATGAAATGCCTTCCCAACCCAATGGTTTCTTTTAATCCAGGCTCAGTGGGTAACACAATC
              CCCACCCCAACCTGTATGTTCCCTCCTTTGTCCTATGACAACTAAACAAGCTACATTCCA
              GCTCCTTTTATCACAGTTTCAGGCCCGTAGTGTCTCTGCCAACCACCGCTGTGCAAACGT
              TCCCACCCCTGTCAGCTCATCCAGTATGTCCAGCATCCCACTCGGCTGACTCACAATATT

32177         CCTTATGAAATGAACATACAGTCTGGGGGTCTTTCAGGGACACCTGCCTGGTGCTTCCAC
              TCTGCCTTCTGTGGCTGGCCACCAGCAACTGAACGGTTTCCGCACAGCACTTGACCTGTC
              ACCCCCAACAACTGGATCCTCTTGCACGGAGCAAATGAAATGCCTTCCCAACCCAATGGT
              TTCTTTTAATCCAGGCTCAGTGGGTAACACAATCCCCACCCCAACCTGTATGTTCCCTCC
              TTTGTCCTATGACAACTAAACAAGCTACATTCCAGCTCCTTTTATCACAGTTTCAGGCCC
              [A,G]
              TAGTGTCTCTGCCAACCACCGCTGTGCAAACGTTCCCACCCCTGTCAGCTCATCCAGTAT
              GTCCAGCATCCCACTCGGCTGACTCACAATATTGACTTTCTCCTTAGCTATACCATCTCC
              TCCTCTCTAGCAACCTCTTCTTTTAAGAACAGCATGTAAACTGGCTTTATCCTTGGCCTA
              GTTAATGGCAGACTCAGCTTATGTCGACTTCCATTGTCAGGGGGTTTTCCTCCTGTGGAC
              ATCACGTACCTGCCCACTCCAAGAACTTCTATTGTACTCTTTCAGCCCAAGACTCCGGAT

33018         AAGGTATGGCCTTCCTACCAGGTGGCACTCCAAGTCTGCTTAAATCTGGGACCCTCCAGG
              AATCTCCTGGGGCTGGATAGCCATAGTGACGGCTGGAACATGAAAAAGAGTCCATTGGTT
              TCTTTTCTTGTGAATTAACAATGTAGCTCTGGCCAGGCACGGTGGCTCATGCCTGTAATC
              CCAGCACTTTGGGAGGCCGAGGCAGGTGGATCGCTTGAGCCCAGGAATTAGACACCAACC
              TGGGCAACACAGGGGAGATTCTGTCTCTACAAAAATAATCAAAATATTAGCCAGGTGTGG
              [T,C]
              GGTGCATGCCTGTAGTCCCAGCTGCTCAGAAGGCTGACGTGAGAAGATCACTTGAGCATG
              GGAGGTCAAGGCTGCAATGAGCCGAGATGGCACCACCGCACTCCAGCCTGGGCAATAGAG
              TGAGACCCTATATCTCAAAAAACAAATAGAAAAAAAAAATATATGTAGCTCTGGCCTTCT
              CTTCTAAAGCAGTTCAGTAGCTCTTCCCATTCACCCAGGTAAGAGGCCTTTATTTCATAA
              AGATAAGTGGGAGGAGTTTAGATATGAAAACAAAACGTAAACACCGCACTGGAGCTATTG

33090         CTGGATAGCCATAGTGACGGCTGGAACATGAAAAAGAGTCCATTGGTTTCTTTTCTTGTG
              AATTAACAATGTAGCTCTGGCCAGGCACGGTGGCTCATGCCTGTAATCCCAGCACTTTGG
              GAGGCCGAGGCAGGTGGATCGCTTGAGCCCAGGAATTAGACACCAACCTGGGCAACACAG
              GGGAGATTCTGTCTCTACAAAAATAATCAAAATATTAGCCAGGTGTGGTGGTGCATGCCT
              GTAGTCCCAGCTGCTCAGAAGGCTGACGTGAGAAGATCACTTGAGCATGGGAGGTCAAGG
              [T,C]
              TGCAATGAGCCGAGATGGCACCACCGCACTCCAGCCTGGGCAATAGAGTGAGACCCTATA
              TCTCAAAAAACAAATAGAAAAAAAAAATATATGTAGCTCTGGCCTTCTCTTCTAAAGCAG
              TTCAGTAGCTCTTCCCATTCACCCAGGTAAGAGGCCTTTATTTCATAAAGATAAGTGGGA
              GGAGTTTAGATATGAAAACAAAACGTAAACACCGCACTGGAGCTATTGTGGAAACAAAAC
              AAGACTGTCCATGGTTCCCCAGCCATTATTATCTCAGCCATACCCCGAATTTCAAAATAA
```

FIGURE 3, page 26 of 33

33993   ATTACAGACCAGGTTTTTCTAGTCCTTTCCTGGTGACCTGGGCATGCCACCACCCTCCCC
        ACTGCTCCCAACCTGATAAGCACATATATACCCGGTGAATTCATGTCTCACAATTAGAGT
        CCTATGACATAGTGTCTGCAGGCTTTGGCTGATGTTCCCATAGTGTCTGCAGGCTTTGGC
        TGATGTTCCCAGGGTTCCCTACTAGGAAGCAAAAAGCACCTTAAACTATTTCATCTTATT
        TCATCTCCTGCCCCTCCTCTCACGTCCTTCTCGAGACTTTTGCAAAGGCAAAGCCAGAAG
        [C,T]
        TCCAGCAGCACCAGGGGATATTTTCCTCTTCCTCTGCCTTCTTCTGTCTTCTTATCTGAA
        GAAGTTTCTCTTTCCCGAGGCCTAGTCCTCTACTGCTGCCTCTACTCCCTCTTCTGCAGA
        AATCCTGCTCTCAGCCAGTGTTTGTATCTCCCCAGGTGCTGGGTGACAGCTCCAGCCTCC
        TAACTGACATCCCTGTCTTCAGACTTAGAGCTCTTAGAATCGTGACTCTCAGCTCTGGCT
        GCATATTAGAATCATTCAGGGACATTGTGTATGTGTGTATGTATGTGTATATATGTATGA

34284   AGCCAGAAGCTCCAGCAGCACCAGGGGATATTTTCCTCTTCCTCTGCCTTCTTCTGTCTT
        CTTATCTGAAGAAGTTTCTCTTTCCCGAGGCCTAGTCCTCTACTGCTGCCTCTACTCCCT
        CTTCTGCAGAAATCCTGCTCTCAGCCAGTGTTTGTATCTCCCCAGGTGCTGGGTGACAGC
        TCCAGCCTCCTAACTGACATCCCTGTCTTCAGACTTAGAGCTCTTAGAATCGTGACTCTC
        AGCTCTGGCTGCATATTAGAATCATTCAGGGACATTGTGTATGTGTGTATGTATGTGTAT
        [G,A]
        TATGTATGAATGTGTGTGTATGTGTGTGTGTGTATGTATGTATGTGTATGTGTGTATGTA
        TGTATGTATGTATGACAGAGTCTCACTCTGTTGCCCAGGTTGGAGAGCAATGGCACCATC
        TCAGTTCACTGCAACCTCCGTCTCCTGGATTCAAGCGATTCTCCTGCCTCAGTCTCCCAA
        GTAGCTGGGGTTATAGGTGCATGCCACCATGACCAGCTAATTTTTGTATTTTTAGTAGAG
        ACAAGGTTTCGCCATGTTGGCCAGGCCAGGCTGGTCTTTAACTCCTGACCTCAGGAGATC

34314   TTTTCCTCTTCCTCTGCCTTCTTCTGTCTTCTTATCTGAAGAAGTTTCTCTTTCCCGAGG
        CCTAGTCCTCTACTGCTGCCTCTACTCCCTCTTCTGCAGAAATCCTGCTCTCAGCCAGTG
        TTTGTATCTCCCCAGGTGCTGGGTGACAGCTCCAGCCTCCTAACTGACATCCCTGTCTTC
        AGACTTAGAGCTCTTAGAATCGTGACTCTCAGCTCTGGCTGCATATTAGAATCATTCAGG
        GACATTGTGTATGTGTGTATGTATGTGTATATATGTATGAATGTGTGTGTATGTGTGTGT
        [G,A]
        TGTATGTATGTATGTGTATGTGTGTATGTATGTATGTATGTATGACAGAGTCTCACTCTG
        TTGCCCAGGTTGGAGAGCAATGGCACCATCTCAGTTCACTGCAACCTCCGTCTCCTGGAT
        TCAAGCGATTCTCCTGCCTCAGTCTCCCAAGTAGCTGGGGTTATAGGTGCATGCCACCAT
        GACCAGCTAATTTTTGTATTTTTAGTAGAGACAAGGTTTCGCCATGTTGGCCAGGCCAGG
        CTGGTCTTTAACTCCTGACCTCAGGAGATCCACCCACCTCGGCCTCCCAAAGTGCTGGGA

35392   GACGTCAGCATGATGGTGTAGAGACTCACTGGGGGATGAATAGTCCTGGAAGAAGGTGGA
        AAGGGGCTTTTGAGGACTATAATAGTCTGTTGCCTGACTGGATGCTGGTATGTTCATTTT
        ATCGAAACTTATCTGTTGCTCACTTATGATTTGTACTCGTTTCTATGTGTATGTTAGCTT
        CAATTAAAAGTTTACTTGAGGCCGGGTACAGTGGCTCACACCTGTAATCCCAGCACTTTG
        GGAGGCCGAGGCAGGCAGATCCCCTGAGGTCAGGAGTTCAATACCAGCCTAGCCAACATG
        [A,G]
        TGAAACCCCATCTCTACTAAAAATACAAAATTAGCCAAGCGTGGTGGCACGTGCCTATAA
        TTCCAGCTACTTGGGAGGCTGAGACAGGAAAATCGCTTGAAACCAGGAGGCAGGGGTTGC
        AGTGAGCCAAGATTGCATCATTGCACTCCAACTCCGGGTGACAAGAGTAAAACTCTGTCTC
        AAATTTAAAAAAAAAAAAAAAAAAAGTTTACTTGAAAAACAATATCAGTGCCTGACCGG
        GCTTATCCCCAGAGAGTCTGACTTAATTGGTCTGGAGTGCGAGCTGGATTCGGTACTTTG

35599   ACAGTGGCTCACACCTGTAATCCCAGCACTTTGGGAGGCCGAGGCAGGCAGATCCCCTGA
        GGTCAGGAGTTCAATACCAGCCTAGCCAACATGATGAAACCCCATCTCTACTAAAAATAC
        AAAATTAGCCAAGCGTGGTGGCACGTGCCTATAATTCCAGCTACTTGGGAGGCTGAGACA
        GGAAAATCGCTTGAAACCAGGAGGCAGGGGTTGCAGTGAGCCAAGATTGCATCATTGCAC
        TCCAGCCTGGGTGACAAGAGTAAAACTCTGTCTCAAATTTAAAAAAAAAAAAAAAAAAAA
        [T,A,G]
        TTTACTTGAAAAACAATATCAGTGCCTGACCGGGCTTATCCCCAGAGAGTCTGACTTAAT
        TGGTCTGGAGTGCGAGCTGGATTCGGTACTTTGTGAAAGCTCCTGAGATTATTTTAATGT
        GCAGGGTTTATGAACCGCTGCCTTAGATCTGGTCCCCACAGAGAAATCAAGTAATCTGTA
        TAAAAGAAAACCTGACCCAGTCACTCCCCTGCTTTCAAACTTCCAAAGCCTCCCACCTCT
        GAAGGAGGCAGGCCAGGCCCCATAGCACAGCACACTAGGCCTCTGGGACTTGGCCTGGTT

35997   AGCTCCTGAGATTATTTTAATGTGCAGGGTTTATGAACCGCTGCCTTAGATCTGGTCCCC
        ACAGAGAAATCAAGTAATCTGTATAAAAGAAAACCTGACCCAGTCACTCCCCTGCTTTCA
        AACTTCCAAAGCCTCCCACCTCTGAAGGAGGCAGGCCAGGCCCCATAGCACAGCACACTA

```
        GGCCTCTGGGACTTGGCCTGGTTCACCTGATTAACCTCTCTGGCTACCATTTCCACCAGC
        GTCTGCCTCGCATGTTACAGTCTAGTGACTCCAGCAGCGTCCTGCACCACCTGTGGTGTT
        [C,A]
        CACACCTCTGCTAACTCTTGCTCTCCTCCTTCTCCTGGATTGCCCTTCTCACCTCCTTGC
        CCACTCCACCACTCAACTCAGGTGCCACCTCCTGCAGGAAGCTACCTCTGAATCTCCAGG
        ACAGGCCAGTGGCCCACCCAGGTCCATTACACCCTGCCCAGTCCTGTCATTTGCTACGTG
        GTTGGTAGCCACAGTGCCTGGCTTAGGAAAGACTGGTTCTAGGAAAAACAATTTCATTCC
        CTGTGGCCAGCTCCAAGCCTTCCCCCGCCAAGCTTCTCCATTCAGGTCTCTGTGAATTTA

36085   GAAAACCTGACCCAGTCACTCCCCTGCTTTCAAACTTCCAAAGCCTCCCACCTCTGAAGG
        AGGCAGGCCAGGCCCCATAGCACAGCACACTAGGCCTCTGGGACTTGGCCTGGTTCACCT
        GATTAACCTCTCTGGCTACCATTTCCACCAGCGTCTGCCTCGCATGTTACAGTCTAGTGA
        CTCCAGCAGCGTCCTGCACCACCTGTGGTGTTCCACACCTCTGCTAACTCTTGCTCTCCT
        CCTTCTCCTGGATTGCCCTTCTCACCTCCTTGCCCACTCCACCACTCAACTCAGGTGCCA
        [C,T]
        CTCCTGCAGGAAGCTACCTCTGAATCTCCAGGACAGGCCAGTGGCCCACCCAGGTCCATT
        ACACCCTGCCCAGTCCTGTCATTTGCTACGTGGTTGGTAGCCACAGTGCCTGGCTTAGGA
        AAGACTGGTTCTAGGAAAAACAATTTCATTCCCTGTGGCCAGCTCCAAGCCTTCCCCCGC
        CAAGCTTCTCCATTCAGGTCTCTGTGAATTTAATTAATTCATCCATCCATCAAACAAGTA
        TTTACTGAGCACTAATATGTGCTAGGTACTGCTCCAGGTGCTGAGGACTCAGCAGTGAAA

36270   GCAGCGTCCTGCACCACCTGTGGTGTTCCACACCTCTGCTAACTCTTGCTCTCCTCCTTC
        TCCTGGATTGCCCTTCTCACCTCCTTGCCCACTCCACCACTCAACTCAGGTGCCACCTCC
        TGCAGGAAGCTACCTCTGAATCTCCAGGACAGGCCAGTGGCCCACCCAGGTCCATTACAC
        CCTGCCCAGTCCTGTCATTTGCTACGTGGTTGGTAGCCACAGTGCCTGGCTTAGGAAAGA
        CTGGTTCTAGGAAAAACAATTTCATTCCCTGTGGCCAGCTCCAAGCCTTCCCCCGCCAAG
        [C,T]
        TTCTCCATTCAGGTCTCTGTGAATTTAATTAATTCATCCATCCATCAAACAAGTATTTAC
        TGAGCACTAATATGTGCTAGGTACTGCTCCAGGTGCTGAGGACTCAGCAGTGAAAAGATG
        ACTGCTACTCTCATGGGACATACAGGATAGTAGGGAAAAGACAGATAATCAACAAGGTCA
        TTTCTGACCACATCTGTGGTTTAAGAAAAAGTCAAGCAGAGTGATGTGATACAGAGTAAT
        GGTGGGGGAGAGGGAGGCCTCCCTGAAGAAGTGACAGTGAATTGAGAAGCGCATGTCAAG

36481   GGTAGCCACAGTGCCTGGCTTAGGAAAGACTGGTTCTAGGAAAAACAATTTCATTCCCTG
        TGGCCAGCTCCAAGCCTTCCCCCGCCAAGCTTCTCCATTCAGGTCTCTGTGAATTTAATT
        AATTCATCCATCCATCAAACAAGTATTTACTGAGCACTAATATGTGCTAGGTACTGCTCC
        AGGTGCTGAGGACTCAGCAGTGAAAAGATGACTGCTACTCTCATGGGACATACAGGATAG
        TAGGGAAAAGACAGATAATCAACAAGGTCATTTCTGACCACATCTGTGGTTTAAGAAAAA
        [G,A]
        TCAAGCAGAGTGATGTGATACAGAGTAATGGTGGGGGAGAGGGAGGCCTCCCTGAAGAAG
        TGACAGTGAATTGAGAAGCGCATGTCAAGGGGTTGCCAGGCAGAGGAAATAGGACCCACA
        TGGGCCTAGAGTCAGGAGTGAGCTTGAAGTGTCTGAGGAACTTAAAGGCCAATGTGACCA
        GAGGGAAGTGAACAAGGTGAAAAAGTTGGGCAGGGGCCAGGTCCCTAGATGCTTCTAAGC
        AGTAGAGTGATATGCTCTGGCTTACCCCTGGGTCCGTGTACCCTGGACTGGAAGAAAGCA

36619   ACAAGTATTTACTGAGCACTAATATGTGCTAGGTACTGCTCCAGGTGCTGAGGACTCAGC
        AGTGAAAAGATGACTGCTACTCTCATGGGACATACAGGATAGTAGGGAAAAGACAGATAA
        TCAACAAGGTCATTTCTGACCACATCTGTGGTTTAAGAAAAAGTCAAGCAGAGTGATGTG
        ATACAGAGTAATGGTGGGGGAGAGGGAGGCCTCCCTGAAGAAGTGACAGTGAATTGAGAA
        GCGCATGTCAAGGGGTTGCCAGGCAGAGGAAATAGGACCCACATGGGCCTAGAGTCAGGA
        [G,A]
        TGAGCTTGAAGTGTCTGAGGAACTTAAAGGCCAATGTGACCAGAGGGAAGTGAACAAGGT
        GAAAAAGTTGGGCAGGGGCCAGGTCCCTAGATGCTTCTAAGCAGTAGAGTGATATGCTCT
        GGCTTACCCCTGGGTCCGTGTACCCTGGACTGGAAGAAAGCAAGGGTGGACCTGGAAAGA
        CCACTAGGAGGCTGCTGTTGATGGGTGAGAGAGGAAGGGGGCTGAGAGTAGGGTCAGGGC
        AGAGGAGGAGAGACGCTGTCGTGGGCTGGCGGATGGATGATGGGGAAGAGGAACAAAGGA

37088   GACCTGGAAAGACCACTAGGAGGCTGCTGTTGATGGGTGAGAGAGGAAGGGGGCTGAGAG
        TAGGGTCAGGGCAGAGGAGGAGAGACGCTGTCGTGGGCTGGCGGATGGATGATGGGGAAG
        AGGAACAAAGGATGACTTTTTGGTTTGGGGTCTAAGAAACTGGGTGGATGATTGAGCAGG
        TAGAGAAAAAATCAGCGTGGGAGGAAAAAAAATCAAGACTTCTGTTTTGGACATGGTGCA
        AACTGCCTTCCAGACATCCACATAGAGGTATCAGGATACAGAAGTTTGGAACTCACAGAG
        [G,C]
```

```
              AAGTCAAGGCTGGAGATTGAAAAAAAAAAAAAAAAAAAAAAAAGTGGGGTTATTAGCATA
              GAGGGCCAATATGGTGAAACCCTGTCTCTACTGAAAATACAAAAATTATCCAGGCATGGT
              GGCATGCACCTGTAATCCCAGCTACTCAGGGAGGCTGAGGCAGGAGAATTGCTTGAACCC
              AGAGATGGGGTGGAGGTTGCAGTAAGCTGAGATCGTGCCATTGCACTCCAGCCTGGGTGA
              CAGGGCAAGATTCCATCTAAAAAAAAAAAAAAGCCACTACAGGATCAACTAAGAGCTCCTA

37204         GAAGAGGAACAAAGGATGACTTTTTGGTTTGGGGTCTAACAAACTGGGTGGATGATTGAG
              CAGGTAGAGAAAAAATCAGCGTGGGAGGAAAAAAAATCAAGACTTCTGTTTTGGACATGG
              TGCAAACTGCCTTCCAGACATCCACATAGAGGTATCAGGATACAGAAGTTTGGAACTCAC
              AGAGGAAGTCAAGGCTGGAGATTGAAAAAAAAAAAAAAAAAAAAAAAAGTGGGGTTATTA
              GCATAGAGGGCCAATATGGTGAAACCCTGTCTCTACTGAAAATACAAAAATTATCCAGGC
              [G,A]
              TGGTGGCATGCACCTGTAATCCCAGCTACTCAGGGAGGCTGAGGCAGGAGAATTGCTTGA
              ACCCAGAGATGGGGTGGAGGTTGCAGTAAGCTGAGATCGTGCCATTGCACTCCAGCCTGG
              GTGACAGGGCAAGATTCCATCTAAAAAAAAAAAAAGCCACTACAGGATCAACTAAGAGCT
              CCTAGAGAAAGAATAGGTAGGTAGAAAAGAGTGTAAGGCCAACTACCTAGCCCTGGGCAT
              TCATTCCAGCTTTCAACTCCAGTGAGAGATGAGAAGGAGAGTGTGGAGGTAGATGGGAAA

37485         ATACAAAAATTATCCAGGCATGGTGGCATGCACCTGTAATCCCAGCTACTCAGGGAGGCT
              GAGGCAGGAGAATTGCTTGAACCCAGAGATGGGGTGGAGGTTGCAGTAAGCTGAGATCGT
              GCCATTGCACTCCAGCCTGGGTGACAGGGCAAGATTCCATCTAAAAAAAAAAAAAGCCAC
              TACAGGATCAACTAAGAGCTCCTAGAGAAAGAATAGGTAGGTAGAAAAGAGTGTAAGGCC
              AACTACCTAGCCCTGGGCATTCATTCCAGCTTTCAACTCCAGTGAGAGATGAGAAGGAGA
              [G,A]
              TGTGGAGGTAGATGGGAAATGAGAAACAATGCTGTGTCCAGAGAGCTAAGAGAAGTCAGT
              GTTTCAAGAGAGACAGAGCTGTCAACTTTGATGGATGCTTCTGAGAAGCCAAGCAAGTTG
              AAGACAAAAAAAAAAAAATGATCTTTGGCTCTGCCCATATGGCGATCGTTGGTGGCCAG
              GGCCAGAGCTTCCATCCAGCGATGGAGACTGCAGACTGGCTGGAGCGAGCAGCAGAGAGA
              AGGAGAGATTAGGAAGTGCTGCCAGCACCTATAGACAGCTCTTCCCAGAAGTTATGAGAA

37624         GGTGACAGGGCAAGATTCCATCTAAAAAAAAAAAAAGCCACTACAGGATCAACTAAGAGC
              TCCTAGAGAAAGAATAGGTAGGTAGAAAAGAGTGTAAGGCCAACTACCTAGCCCTGGGCA
              TTCATTCCAGCTTTCAACTCCAGTGAGAGATGAGAAGGAGAGTGTGGAGGTAGATGGGAA
              ATGAGAAACAATGCTGTGTCCAGAGAGCTAAGAGAAGTCAGTGTTTCAAGAGAGACAGAG
              CTGTCAACTTTGATGGATGCTTCTGAGAAGCCAAGCAAGTTGAAGACAAAAAAAAAAAAA
              [-,A]
              TGATCTTTGGCTCTGCCCATATGGCGATCGTTGGTGGCCAGGGCCAGAGCTTCCATCCAG
              CGATGGAGACTGCAGACTGGCTGGAGCGAGCAGCAGAGAGAAGGAGAGATTAGGAAGTGC
              TGCCAGCACCTATAGACAGCTCTTCCCAGAAGTTATGAGAAGTAACAGCCACGGTCACTG
              GAGGGGACATGGATCAAAGAAAGGGCAGGTGAAGGAGGGGAGATGTCGGAGCAGGTTGTG
              TACTGACGAGAAGGAACCAGTAGAAAGGGAGAAACTGATGCACTCATCAAACCCTTGTAA

37685         CCTAGAGAAAGAATAGGTAGGTAGAAAAGAGTGTAAGGCCAACTACCTAGCCCTGGGCAT
              TCATTCCAGCTTTCAACTCCAGTGAGAGATGAGAAGGAGAGTGTGGAGGTAGATGGGAAA
              TGAGAAACAATGCTGTGTCCAGAGAGCTAAGAGAAGTCAGTGTTTCAAGAGAGACAGAGC
              TGTCAACTTTGATGGATGCTTCTGAGAAGCCAAGCAAGTTGAAGACAAAAAAAAAAAAAA
              TGATCTTTGGCTCTGCCCATATGGCGATCGTTGGTGGCCAGGGCCAGAGCTTCCATCCAG
              [C,T]
              GATGGAGACTGCAGACTGGCTGGAGCGAGCAGCAGAGAGAAGGAGAGATTAGGAAGTGCT
              GCCAGCACCTATAGACAGCTCTTCCCAGAAGTTATGAGAAGTAACAGCCACGGTCACTGG
              AGGGGACATGGATCAAAGAAAGGGCAGGTGAAGGAGGGGAGATGTCGGAGCAGGTTGTGT
              ACTGACGAGAAGGAACCAGTAGAAAGGGAGAAACTGATGCACTCATCAAACCCTTGTAAT
              CACGATCATCTTCTGTGTGAATTAGTTCTGGGTTCCTGGAATAGCATCGGGAATCAGCCG

37769         AGAGATGAGAAGGAGAGTGTGGAGGTAGATGGGAAATGAGAAACAATGCTGTGTCCAGAG
              AGCTAAGAGAAGTCAGTGTTTCAAGAGAGACAGAGCTGTCAACTTTGATGGATGCTTCTG
              AGAAGCCAAGCAAGTTGAAGACAAAAAAAAAAAAAATGATCTTTGGCTCTGCCCATATGG
              CGATCGTTGGTGGCCAGGGCCAGAGCTTCCATCCAGCGATGGAGACTGCAGACTGGCTGG
              AGCGAGCAGCAGAGAGAAGGAGAGATTAGGAAGTGCTGCCAGCACCTATAGACAGCTCTT
              [C,T]
              CCAGAAGTTATGAGAAGTAACAGCCACGGTCACTGGAGGGGACATGGATCAAAGAAAGGG
              CAGGTGAAGGAGGGGAGATGTCGGAGCAGGTTGTGTACTGACGAGAAGGAACCAGTAGAA
              AGGGAGAAACTGATGCACTCATCAAACCCTTGTAATCACGATCATCTTCTGTGTGAATTA
```

FIGURE 3, page 29 of 33

| | |
|---|---|
| | GTTCTGGGTTCCTGGAATAGCATCGGGAATCAGCCGCGCTGACCTTTAGCATTTATTCTG<br>TCACTGTTACGATAGACTTGAGTTTCCTCAGTTCTTAAGAAAGTGGAAATAATACTACCT |
| 38897 | AGAGGGTCCTGGGATCAAAGGTATTTACACCCAGGGATATTTCAGATAAATCTTTTCATC<br>TATGTGGAAAACATACAAAGTGGCGCAAGTGAGAAACTCCGATTTCCTAAGGTTGACAAG<br>TCAAGTGCAGTAATGATGTCATGGTAACCAATATGTTTCCAAACTTTCCTAAGGTTGACT<br>AGCCCCATGCACTTTGAGAAGTTGGTAAATAGGATTGTCGTCGTTTTATAAAATTGAAAA<br>CACGGTGTCTTGCAATCACAGCCACTCACAAAGGAAGCCAGAGATGGTCCCAGCCCCTCC<br>[G,A]<br>CAGACTTCCTGTGGACTCAGGACTGGTGGTCTCTCCTGGGCCTTGCTGTACCCGGCAAAT<br>CCAGGGGCACAGACTCAGGGTTCTGCCCTGCCGACAGATGCTGCCTAGCCTTCTGTGTGT<br>CATAAGTCAACTCCCGCTCAGCCCCAGGCTGCTGGGTCCCTGCTGTGGGCCAAAAACCAG<br>CCACTTCGCTGGTTTCTATCCCCCACCCCGTTCCCGAGGGAGGGGCTCTGGTGTGAGACA<br>CCCCCTCAGAGAGGAAAGTGTCTCCCAGCTTTGGAGAGAATCGAGGTGTCCTTTCTCTCT |
| 40155 | AGACTGAGTGACAGAGTGAGACTGTCTCAAAAATAAAGTGCATCAAGCAGCTGTCCCGTG<br>CCAGGCAGTATACTAGGATCTGGGGATCGGGAGGCAAAGATAAAATAGACTCAGTGTCTG<br>TTCCTGGAGCCTGCAATGGTCTTCCTCCCTCGCCACACCCACTGCCCTTGCCTGGCCCAC<br>CTTCGAAGCCTGTGACTTGTCTCCCCAGCTCTCCTCTCCCTCTTCTCCATCCACCCTACA<br>CTTGCTGCCAGACACAGATAGACCTTCCTGGAAATAACTTGCCCCATCAAGGCTGCTTGA<br>[A,G]<br>ATCCTTGCCTGATCCCTACTGCCCATTGACCAGAGTCTGGAGGGAGGGTCACCTCCCTCC<br>ATGATACACACTGCACTCCTGGCCGGTGGATCCATCTCCCAGGAAGCCCCACGACTGCCC<br>GCATCCAGGCCTTTCCTTTTGCCATCTGTTCCTGGAGGTTCATCTTCCATCTGCTATGAG<br>AACATCCGCCTCCCTCCAGGTCCAGATGTTGCCTTTACTAAGCGATGGTTTCACCGTCTC<br>TTACCTACCATTCCTGTCTCCAGACACTGACCCATGTGGGTCTCCTTTTCTATTTGTACC |
| 40355 | CTCCCCAGCTCTCCTCTCCCTCTTCTCCATCCACCCTACACTTGCTGCCAGACACAGATA<br>GACCTTCCTGGAAATAACTTGCCCCATCAAGGCTGCTTGAAATCCTTGCCTGATCCCTAC<br>TGCCCATTGACCAGAGTCTGGAGGGAGGGTCACCTCCCTCCATGATACACACTGCACTCC<br>TGGCCGGTGGATCCATCTCCCAGGAAGCCCCACGACTGCCCGCATCCAGGCCTTTCCTTT<br>TGCCATCTGTTCCTGGAGGTTCATCTTCCATCTGCTATGAGAACATCCGCCTCCCTCCAG<br>[G,C]<br>TCCAGATGTTGCCTTTACTAAGCGATGGTTTCACCGTCTCTTACCTACCATTCCTGTCTC<br>CAGACACTGACCCATGTGGGTCTCCTTTTCTATTTGTACCTCTCATGAGACACCGACCCA<br>GTCTCCTTTATGATGTGATTGTTTCTGCACATCTCAACTTCCTCCTGGGCCACAAGAAAA<br>GATGTCACATCTTAACCCTCCAGTCTCATCACAGCTTCCAGCAAGGGGGCTAAACACAGC<br>ACGTGCCCAATTCACATTCACTGAGAGGAGAGTGGAGAGGGGCATAGGAAGGCAAGAACG |
| 40486 | CAGAGTCTGGAGGGAGGGTCACCTCCCTCCATGATACACACTGCACTCCTGGCCGGTGGA<br>TCCATCTCCCAGGAAGCCCCACGACTGCCCGCATCCAGGCCTTTCCTTTTGCCATCTGTT<br>CCTGGAGGTTCATCTTCCATCTGCTATGAGAACATCCGCCTCCCTCCAGGTCCAGATGTT<br>GCCTTTACTAAGCGATGGTTTCACCGTCTCTTACCTACCATTCCTGTCTCCAGACACTGA<br>CCCATGTGGGTCTCCTTTTCTATTTGTACCTCTCATGAGACACCGACCCAGTCTCCTTTA<br>[T,C]<br>GATGTGATTGTTTCTGCACATCTCAACTTCCTCCTGGGCCACAAGAAAAGATGTCACATC<br>TTAACCCTCCAGTCTCATCACAGCTTCCAGCAAGGGGGCTAAACACAGCACGTGCCCAAT<br>TCACATTCACTGAGAGGAGAGTGGAGAGGGGCATAGGAAGGCAAGAACGCACACGATCTG<br>CCCACATGCCTCCCCTCCCGGCCCTTCTGATTTGGGGATCTTTCATCTACTACAAAACCA<br>GCTGTCCTTCCATGCTGCCCTTCCCTGATTTCTGGGTAGTCCTGGGATGGGAGAATGGGG |
| 40512 | CTCCATGATACACACTGCACTCCTGGCCGGTGGATCCATCTCCCAGGAAGCCCCACGACT<br>GCCCGCATCCAGGCCTTTCCTTTTGCCATCTGTTCCTGGAGGTTCATCTTCCATCTGCTA<br>TGAGAACATCCGCCTCCCTCCAGGTCCAGATGTTGCCTTTACTAAGCGATGGTTTCACCG<br>TCTCTTACCTACCATTCCTGTCTCCAGACACTGACCCATGTGGGTCTCCTTTTCTATTTG<br>TACCTCTCATGAGACACCGACCCAGTCTCCTTTATGATGTGATTGTTTCTGCACATCTCA<br>[A,C]<br>CTTCCTCCTGGGCCACAAGAAAAGATGTCACATCTTAACCCTCCAGTCTCATCACAGCTT<br>CCAGCAAGGGGGCTAAACACAGCACGTGCCCAATTCACATTCACTGAGAGGAGAGTGGAG<br>AGGGGCATAGGAAGGCAAGAACGCACACGATCTGCCCACATGCCTCCCCTCCCGGCCCTT<br>CTGATTTGGGGATCTTTCATCTACTACAAAACCAGCTGTCCTTCCATGCTGCCCTTCCCT<br>GATTTCTGGGTAGTCCTGGGATGGGAGAATGGGGACAGTTGTGACCACGAGGAAGCAGAG |

FIGURE 3, page 30 of 33

40622    CCATCTGCTATGAGAACATCCGCCTCCCTCCAGGTCCAGATGTTGCCTTTACTAAGCGAT
GGTTTCACCGTCTCTTACCTACCATTCCTGTCTCCAGACACTGACCCATGTGGGTCTCCT
TTTCTATTTGTACCTCTCATGAGACACCGACCCAGTCTCCTTTATGATGTGATTGTTTCT
GCACATCTCAACTTCCTCCTGGGCCACAAGAAAAGATGTCACATCTTAACCCTCCAGTCT
CATCACAGCTTCCAGCAAGGGGGCTAAACACAGCACGTGCCCAATTCACATTCACTGAGA
[-,A,G]
GAGAGTGGAGAGGGGCATAGGAAGGCAAGAACGCACACGATCTGCCCACATGCCTCCCCT
CCCGGCCCTTCTGATTTGGGGATCTTTCATCTACTACAAAACCAGCTGTCCTTCCATGCT
GCCCTTCCCTGATTTCTGGGTAGTCCTGGGATGGGAGAATGGGGACAGTTGTGACCACGA
GGAAGCAGAGGTGGGAGTTCTACAGGCCCCACAGGGCTCTCTGCCATTGGTCACCTATCA
GTTCCCAATCTTTCAAAATCAGGTTTGATGGCCAAGGAAACGCTGGTGAGAAACCAAAAG

40654    GGTCCAGATGTTGCCTTTACTAAGCGATGGTTTCACCGTCTCTTACCTACCATTCCTGTC
TCCAGACACTGACCCATGTGGGTCTCCTTTTCTATTTGTACCTCTCATGAGACACCGACC
CAGTCTCCTTTATGATGTGATTGTTTCTGCACATCTCAACTTCCTCCTGGGCCACAAGAA
AAGATGTCACATCTTAACCCTCCAGTCTCATCACAGCTTCCAGCAAGGGGGCTAAACACA
GCACGTGCCCAATTCACATTCACTGAGAGGAGAGTGGAGAGGGGCATAGGAAGGCAAGAA
[T,C]
GCACACGATCTGCCCACATGCCTCCCCTCCCGGCCCTTCTGATTTGGGGATCTTTCATCT
ACTACAAAACCAGCTGTCCTTCCATGCTGCCCTTCCCTGATTTCTGGGTAGTCCTGGGAT
GGGAGAATGGGGACAGTTGTGACCACGAGGAAGCAGAGGTGGGAGTTCTACAGGCCCCAC
AGGGCTCTCTGCCATTGGTCACCTATCAGTTCCCAATCTTTCAAAATCAGGTTTGATGGC
CAAGGAAACGCTGGTGAGAAACCAAAAGAAGGTTCTAGCTGGGTGTTGACCTCTTTAGAG

40933    AGGGGCATAGGAAGGCAAGAACGCACACGATCTGCCCACATGCCTCCCCTCCCGGCCCTT
CTGATTTGGGGATCTTTCATCTACTACAAAACCAGCTGTCCTTCCATGCTGCCCTTCCCT
GATTTCTGGGTAGTCCTGGGATGGGAGAATGGGGACAGTTGTGACCACGAGGAAGCAGAG
GTGGGAGTTCTACAGGCCCCACAGGGCTCTCTGCCATTGGTCACCTATCAGTTCCCAATC
TTTCAAAATCAGGTTTGATGGCCAAGGAAACGCTGGTGAGAAACCAAAAGAAGGTTCTAG
[C,G]
TGGGTGTTGACCTCTTTAGAGGCCCATCCCGCTAAAGAGGGTTTGGGCACAGCCTAAATG
AGGGAGCTTTACAAAAGGGAAGCTCTGTGAAAACGTGCAGGGTTATCGCAGCATCTCAGG
AATGGGGACTAGGCAAGTCTTGGCTTGGTGATGGATGGTTCACGGAGATCCTTTCCACTG
ACCCCCGCTCCTCCTCCACAGGAGAGCCCTTACCTCTACACCCTGCGGAACAGCCGATTG
CTCCCAGACCAGGCTGAAGAAGCCCCGAGGTGCTCTACTGGGCTGTCCCAGTGGCAGCG

41171    TCTTTCAAAATCAGGTTTGATGGCCAAGGAAACGCTGGTGAGAAACCAAAAGAAGGTTCT
AGCTGGGTGTTGACCTCTTTAGAGGCCCATCCCGCTAAAGAGGGTTTGGGCACAGCCTAA
ATGAGGGAGCTTTACAAAAGGGAAGCTCTGTGAAAACGTGCAGGGTTATCGCAGCATCTC
AGGAATGGGGACTAGGCAAGTCTTGGCTTGGTGATGGATGGTTCACGGAGATCCTTTCCA
CTGACCCCCGCTCCTCCTCCACAGGAGAGCCCTTACCTCTACACCCTGCGGAACAGCCGA
[T,C]
TGCTCCCAGACCAGGCTGAAGAAGCCCCGAGGTGCTCTACTGGGCTGTCCCAGTGGCAG
CGGGAGTCGGCCTTGTGGTGGGCATCATCGGGACAGTGGTCTGGAGGTGCAGGAGAGGTG
GCCGGAGGGAAGATCCTCCAATGAGCCTGCGCACTGTGGCCCTCTAGGCCCGGGGGTGGG
TCCTCACCCTAAACTCCCTATAGCCACTCTCTTCACCGCCCTCTGCCCCAGCCACTCCCG
GCCACCAGGACATGCTTCAATGCCTGGTGCCATAGGAAGCCCAGGGGACAGTCACAACTT

41379    TGGTGATGGATGGTTCACGGAGATCCTTTCCACTGACCCCCGCTCCTCCTCCACAGGAGA
GCCCTTACCTCTACACCCTGCGGAACAGCCGATTGCTCCCAGACCAGGCTGAAGAAGCCC
CGAGGTGCTCTACTGGGCTGTCCCAGTGGCAGCGGGAGTCGGCCTTGTGGTGGGCATCA
TCGGGACAGTGGTCTGGAGGTGCAGGAGAGGTGGCCGGAGGGAAGATCCTCCAATGAGCC
TGCGCACTGTGGCCCTCTAGGCCCGGGGGTGGGTCCTCACCCTAAACTCCCTATAGCCAC
[T,C]
CTCTTCACCGCCCTCTGCCCCAGCCACTCCCGGCCACCAGGACATGCTTCAATGCCTGGT
GCCATAGGAAGCCCAGGGGACAGTCACAACTTCTTGGGGCCTGGGCTTCTTCCAGGCCTA
TGCTTCCTGGAATGGATACATTTAAATAAAGTCCAAAGCTATTTTATTCCTGGGTTTGCCT
GCGTGAAGCACTCACCTTCCATCTCTTGTGCAGCCCAGGTGTGGGAGCTGCCACTTTTTG
TGGCCTGCCTCCAGCAGGGCTGCCCAAGCCACGACCAACCAGAGCCCAAACTGCCTGCCA

41388    ATGGTTCACGGAGATCCTTTCCACTGACCCCCGCTCCTCCTCCACAGGAGAGCCCTTACC
TCTACACCCTGCGGAACAGCCGATTGCTCCCAGACCAGGCTGAAGAAGCCCCGAGGTGC
TCTACTGGGCTGTCCCAGTGGCAGCGGGAGTCGGCCTTGTGGTGGGCATCATCGGGACAG

FIGURE 3, page 31 of 33

```
        TGGTCTGGAGGTGCAGGAGAGGTGGCCGGAGGCAAGATCCTCCAATGAGCCTGCGCACTG
        TGGCCCTCTAGGCCCGGGGGTGGGTCCTCACCCTAAACTCCCTATAGCCACTCTCTTCAC
        [C,T]
        GCCCTCTGCCCCAGCCACTCCCGGCCACCAGGACATGCTTCAATGCCTGGTGCCATAGGA
        AGCCCAGGGGACAGTCACAACTTCTTGGGGCCTGGGCTTCTTCCAGGCCTATGCTCCTGG
        AATGGATACATTTAAATAAAGTCCAAAGCTATTTTATTCCTGGGTTTGCCTGCGTGAAGC
        ACTCACCTTCCATCTCTTGTGCAGCCCAGGTGTGGGAGCTGCCACTTTTTGTGGCCTGCC
        TCCAGCAGGGCTGCCCAAGCCACGACCAACCAGAGCCCAAACTGCCTGCCACCACGAGCA

41880   ATCTCTTGTGCAGCCCAGGTGTGGGAGCTGCCACTTTTTGTGGCCTGCCTCCAGCAGGGC
        TGCCCAAGCCACGACCAACCAGAGCCCAAACTGCCTGCCACCACGAGCATATCCTCAAGT
        CACCAAACCCACTATTTCAAAGGCAGAAAAAATGCTGGTCACCAGGTGGTGGCTGGAATT
        TTGGAGCTGGCTGGTTGCCATTCAGTCCAATCCAACACATACCTATTAAGCAACTGTTTT
        GTATCCAGGACAATGCGAAGCACTGAGGTGCCTCCTAGGCTGTGCATGTCGCAGCCTGGC
        [A,C]
        GAGAGGTCAAACTCCTTCAATAACCAAGAAGCCACGTGATGATGTGTAACTACTAGGGCA
        TCAGTAGGTAAATGTGTCTGATTGTTTTAAAGAATAGAAAGGGTTCTTCGGGGAAAGTTT
        CTTGGGGGAGAGCAACCTTCACATGTCATTTTGGGAAAAGGAATAAAAAATGATTGGGAC
        ACAAATACCTCCTATATTCTCAACCTGATTTTCTCAAGGTGCTAAATTTAGGAAAAAATT
        CCTATTTCTATATGCCCAGGTTTCTGAGGGAAAACTAGAGAGAGTCTGAAAATATGGGCT

42278   AAAGGGTTCTTCGGGGAAAGTTTCTTGGGGGAGAGCAACCTTCACATGTCATTTTGGGAA
        AAGGAATAAAAAATGATTGGGACACAAATACCTCCTATATTCTCAACCTGATTTTCTCAA
        GGTGCTAAATTTAGGAAAAAATTCCTATTTCTATATGCCCAGGTTTCTGAGGGAAAACTA
        GAGAGAGTCTGAAAATATGGGCTGCATTCACTGAGCCCCTGCTAGGGGCGAGGCCCCGTG
        CTGGAGGCCTTCCACAGATGGTCTCTTTTATGCTGCACAAAAGCCCAGGGAGGGGGTAAA
        [G,A]
        GGAAAATCTTTGAAAATAGAAGTGATGCTTGCGCAACACCGTGAATGTACTAAACGCCGC
        GAATTGTTCCATTTAAAATGATTAATTGTGTATCATGTGAATTTCACTTCAATAAAAAAG
        AATCCAGGGAGGTAGACATCATCTGCATTGTAAACCTCTCTCTGATCCTGAAGTCCGGGA
        TGATAAAGAGCCTGAGTCACAATCCCGGATGCAACACTGAAATGCTGTGCCCTGAAGCTG
        CCTTCGCCAGCCTGAGCCCAGTGTCCCAGGCTCTGCATCTGTAAAAACTGGAGTAAGAGT

42339   AGGAATAAAAAATGATTGGGACACAAATACCTCCTATATTCTCAACCTGATTTTCTCAAG
        GTGCTAAATTTAGGAAAAAATTCCTATTTCTATATGCCCAGGTTTCTGAGGGAAAACTAG
        AGAGAGTCTGAAAATATGGGCTGCATTCACTGAGCCCCTGCTAGGGGCGAGGCCCCGTGC
        TGGAGGCCTTCCACAGATGGTCTCTTTTATGCTGCACAAAAGCCCAGGGAGGGGGTAAAA
        GGAAAATCTTTGAAAATAGAAGTGATGCTTGCGCAACACCGTGAATGTACTAAACGCCGC
        [G,A]
        AATTGTTCCATTTAAAATGATTAATTGTGTATCATGTGAATTTCACTTCAATAAAAAAGA
        ATCCAGGGAGGTAGACATCATCTGCATTGTAAACCTCTCTCTGATCCTGAAGTCCGGGAT
        GATAAAGAGCCTGAGTCACAATCCCGGATGCAACACTGAAATGCTGTGCCCTGAAGCTGC
        CTTCGCCAGCCTGAGCCCAGTGTCCCAGGCTCTGCATCTGTAAAAACTGGAGTAAGAGTA
        CACATTTTGCTTATCTCACGGCGCTGCTGAAAAATAAGGAACCGTGTGTGAACCTCTAAC

42612   CAACACCGTGAATGTACTAAACGCCGCGAATTGTTCCATTTAAAATGATTAATTGTGTAT
        CATGTGAATTTCACTTCAATAAAAAAGAATCCAGGGAGGTAGACATCATCTGCATTGTAA
        ACCTCTCTCTGATCCTGAAGTCCGGGATGATAAAGAGCCTGAGTCACAATCCCGGATGCA
        ACACTGAAATGCTGTGCCCTGAAGCTGCCTTCGCCAGCCTGAGCCCAGTGTCCCAGGCTC
        TGCATCTGTAAAAACTGGAGTAAGAGTACACATTTTGCTTATCTCACGGCGCTGCTGAAA
        [A,G]
        ATAAGGAACCGTGTGTGAACCTCTAACTCTAAAATGCTGCACAACTGAAAATGGCCTTTT
        TCCTCGGTGAAGAGTTGGGATAAGGCCCAGACTGTTGGGGAAGATGTGAGACCCAGAGAT
        GAGTTTGGGGAAATGGGGTAATAACATATGGGTGGAGAGTGCCCGCCTTCCTCTCAGGGA
        GGTTCATCACCTTATCTCTTTCTGTCACAACAGAGAACCCGGAGGACCTATACCCAGTTC
        CGTGTTCTTCTGGGCTTCAGTGTCTGTTTCTATACAATGGGAACAGCATGCATTCCCCTG

42817   TGCCTTCGCCAGCCTGAGCCCAGTGTCCCAGGCTCTGCATCTGTAAAAACTGGAGTAAGA
        GTACACATTTTGCTTATCTCACGGCGCTGCTGAAAAATAAGGAACCGTGTGTGAACCTCT
        AACTCTAAAATGCTGCACAACTGAAAATGGCCTTTTTCCTCGGTGAAGAGTTGGGATAAG
        GCCCAGACTGTTGGGGAAGATGTGAGACCCAGAGATGAGTTTGGGGAAATGGGGTAATAA
        CATATGGGTGGAGAGTGCCCGCCTTCCTCTCAGGGAGGTTCATCACCTTATCTCTTTCTG
        [T,G]
```

FIGURE 3, page 32 of 33

```
CACAACAGAGAACCCGGAGGACCTATACCCAGTTCCGTGTTCTTCTGGGCTTCAGTGTCT
GTTTCTATACAATGGGAACAGCATGCATTCCCCTGCTTTTCCTATAGACTGGAAAACGT
GGTGACCAAGTCACACATCCCAGCTTATGCTCCCGGCTTAAGACAGTGTAACGACAAAGG
TAACCCTTACACTCCTGGTTTGAGACAGTATAACGACAAAGGTAACATAGGAAGTCAAGG
AGTTCGCTTCACCGCCCCTCCCCCCACCCCACCCTTTTTTTTTCCTGCAAGTTTCTATTC
```

FIGURE 3, page 33 of 33

ISOLATED HUMAN PHOSPHOLIPASE PROTEINS, NUCLEIC ACID MOLECULES ENCODING HUMAN PHOSPHOLIPASE PROTEINS, AND USES THEREOF

FIELD OF THE INVENTION

The present invention is in the field of phospholipase proteins that are related to the phospholipase B subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Phospholipases

There are three major families of known human phospholipase enzymes: Phospholipase A2, Phospholipase C, and Phospholipase D.

Enzymes in the Phospholipase A2 family ("PlA2") hydrolyze the sn-2 fatty acid acyl ester bond of phosphoglycerides, releasing free fatty acids and lysophospholipids. The PlA2s constitute a diverse family of enzymes with respect to sequence, function, localization and divalent cation requirements. They play an important role in a variety of cellular processes, including the digestion and metabolism of phospholipids as well as the production of precursors for inflammatory reactions. The PlA2s have been classified into at least 5 groups (although different classification schemes exist and up to 10 groups have been identified by some authorities) based on their size, structure and need for divalent cations. Groups I, II and III all contain secreted forms of PlA, which are extracellular enzymes that have a low molecular mass and require calcium ions for catalysis. Groups IV and V contain cytosolic forms of PlA2s that have a high molecular mass and do not necessarily require calcium ions.

Amongst the best characterized of the PlA2 phospholipases are digestive enzymes secreted as zymogens by the pancreas. These enzymes, which are involved in the hydrolysis of dietary phospholipids, have strong homology to the venom phospholipases of snakes. Other PlA2s play important roles in the control of signaling cascades such as the cytosolic PlA2, Group IV A enzyme ("PLA2G4A") which catalyzes the release of arachidonic acid from membrane phospholipids. Arachidonic acid serves as a precursor for a wide spectrum of biological effectors, collectively known as eicosanoids (and including the prostaglandin group of molecules) that are involved in hemodynamic regulation, inflammatory responses and other cellular processes.

Another biologically active phospholipid, platelet-activating factor ("PAF") is hydrolyzed to metabolically-inactive degradation products by the group VII PlA2 known as PAF acetylhydrolase. Deficiency of PAF acetylhydrolase has been reported in patients with systemic lupus erythematosis and increased levels of PAF have been reported in children with acute asthmatic attacks. Elevated levels of the group II PlA2 known as PLA2G2A have been reported in plasma and synovial fluid in patients with inflammatory arthritis. Studies of a mouse colon cancer model showed that alleles of the murine ortholog of this gene were able to modify the number of tumors that developed in animals with multiple intestinal neoplasia (a mouse model of the human disorder known as familial adenomtous polyposis). Subsequent studies in humans showed mutations in PLA2G2A were associated with the risk of developing colorectal cancer. PLA2G2A is presumed to act through altering cellular microenvironments within the intestinal crypts of the colonic mucosa, although the precise mechanism by which this effect is exerted is not clear.

Enzymes in the Phospholipase C ("PLC") family catalyze the hydrolysis of the plasma membrane phospholipids, phosphatidyl inositol phosphate ("PIP") or phosphatidylinositol 4,5-biphosphate ("PIP2"), generating as products the second messengers, 1,4,5-inositol triphosphate ("IP3") and 1,2-diacylglycerol ("DAG"). Molecules belonging to the PLC gene family are divided into subfamilies, PLC-beta, PLC-gamma and PLC-delta. PLC-delta is distinguished from PLC-gamma by lack of the SH2 and SH3 domains that are essential for activation of PLC-gamma by tyrosine protein kinases. PLC-delta is distinguished from PLC-beta by lack of the C-terminal region of PLC-beta that is responsible for binding and activation of G proteins. Various PLC enzymes play important roles in signal transduction cascades throughout the body. Activating signals include hormones, growth factors and neurotransmitters. One of the functions of IP2 is to modulate intracellular calcium levels while DAG is involved in the activation of certain protein kinases and can promote membrane fusion in processes involving vesicular trafficking.

Enzymes in the Phospholipase D ("PLD") family catalyze the hydrolysis of phosphatidylcholine ("PC") and other phospholipids to produce phosphatidic acid. A range of agonists acting through G protein-coupled receptors and receptor tyrosine kinases stimulate this hydrolysis. Phosphatidic acid appears to be important as a second messenger capable of activating a diverse range of signaling pathways. PC-specific PLD activity has been implicated in numerous cellular pathways, including signal transduction, membrane trafficking, the regulation of mitosis, regulated secretion, cytoskeletal reorganization, transcriptional regulation and cell-cycle control. Many proteins are attached to the plasma membrane via a glysylphosphatidylinositol ("GPI") anchor. Phosphatidylinositol-glycan ("PIG")-specific PLDs selectively hydrolyze the inositol phosphate linkage, allowing release of the protein.

Phospholipase B/AdRab-B

The novel human protein, and encoding gene, provided by the present invention is related to the rabbit AdRab-B protein (see Boll et al., *J Biol Chem* 1993 Jun. 15;268(17): 12901–11), which is a member of the GDSL family of lipolytic enzymes and is homologous to guinea pig (see Delagebeaudeuf et al., *J Biol Chem* 1998 May 29;273(22): 13407–14) and rat (see Takemori et al., *J Biol Chem* 1998 Jan. 23;273 (4):2222–31) calcium-independent phospholipase B.

AdRab-B is found at the brush border membranes of intestinal cells of adult rabbits (Boll et al., *J Biol Chem* 1993 Jun. 15;268(17):12901–11). Phospholipase B in rats has been found at the brush border membranes of absorptive cells, Paneth cells, and acrosomes of spermatids (Takemori et al., *J Biol Chem* 1998 Jan. 23;273(4):2222–31). AdRab-B has esterase and phospholipase A/lysophospholipase activity and can convert phosphatidylcholine to fatty acids and glycerophosphocholine. Phospholipase B has phospholipase A2, lysophospholipase, and lipase activity. Phospholipase B and AdRab-B likely play important roles in male reproduction and intestinal digestion, particularly in the uptake of dietary lipids, including long-chain retinyl esters.

Phospholipase proteins, particularly members of the phospholipase B subfamily, are a major target for drug action and development. Accordingly, it is valuable to the field of pharmaceutical development to identify and characterize previously unknown members of this subfamily of phospholipase proteins. The present invention advances the state of the art by providing previously unidentified human phospholipase proteins that have homology to members of the phospholipase B subfamily.

SUMMARY OF THE INVENTION

The present invention is based in part on the identification of amino acid sequences of human phospholipase peptides and proteins that are related to the phospholipase B subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate phospholipase activity in cells and tissues that express the phospholipase. Experimental data as provided in FIG. 1 indicates expression in humans in the kidney, blood, lung, brain glioblastomas, prostate, colon, leukocytes, and a mixed melanocyte/fetal heart/pregnant uterus sample.

DESCRIPTION OF THE FIGURE SHEETS

FIG. 1 provides the nucleotide sequence of a cDNA molecule that encodes the phospholipase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in the kidney, blood, lung, brain glioblastomas, prostate, colon, leukocytes, and a mixed melanocyte/fetal heart/pregnant uterus sample.

FIG. 2 provides the predicted amino acid sequence of the phospholipase of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the phospholipase protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 85 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a phospholipase protein or part of a phospholipase protein and are related to the phospholipase B subfamily. Utilizing these sequences, additional genomic sequences were assembled and transcript and/or cDNA sequences were isolated and characterized. Based on this analysis, the present invention provides amino acid sequences of human phospholipase peptides and proteins that are related to the phospholipase B subfamily, nucleic acid sequences in the form of transcript sequences, cDNA sequences and/or genomic sequences that encode these phospholipase peptides and proteins, nucleic acid variation (allelic information), tissue distribution of expression, and information about the closest art known protein/peptide/domain that has structural or sequence homology to the phospholipase of the present invention.

In addition to being previously unknown, the peptides that are provided in the present invention are selected based on their ability to be used for the development of commercially important products and services. Specifically, the present peptides are selected based on homology and/or structural relatedness to known phospholipase proteins of the phospholipase B subfamily and the expression pattern observed. Experimental data as provided in FIG. 1 indicates expression in humans in the kidney, blood, lung, brain glioblastomas, prostate, colon, leukocytes, and a mixed melanocyte/fetal heart/pregnant uterus sample. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known phospholipase B family or subfamily of phospholipase proteins.

Specific Embodiments

Peptide Molecules

The present invention provides nucleic acid sequences that encode protein molecules that have been identified as being members of the phospholipase family of proteins and are related to the phospholipase B subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the phospholipase peptides of the present invention, phospholipase peptides, or peptides/proteins of the present invention.

The present invention provides isolated peptide and protein molecules that consist of, consist essentially of, or comprise the amino acid sequences of the phospholipase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the phospholipase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated phospholipase peptide can be purified from cells that naturally express it, purified from cells that have been altered to express it (recombinant), or synthesized using known protein synthesis methods. Experimental data as provided in FIG. 1 indicates expression in humans in the kidney, blood, lung, brain glioblastomas, prostate, colon, leukocytes, and a mixed melanocyte/fetal heart/pregnant uterus sample. For example, a nucleic acid molecule encoding the phospholipase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids.

The preferred classes of proteins that are comprised of the phospholipase peptides of the present invention are the naturally occurring mature proteins. A brief description of how various types of these proteins can be made/isolated is provided below.

The phospholipase peptides of the present invention can be attached to heterologous sequences to form chimeric or fusion proteins. Such chimeric and fusion proteins comprise a phospholipase peptide operatively linked to a heterologous protein having an amino acid sequence not substantially homologous to the phospholipase peptide. "Operatively linked" indicates that the phospholipase peptide and the heterologous protein are fused in-frame. The heterologous protein can be fused to the N-terminus or C-terminus of the phospholipase peptide.

In some uses, the fusion protein does not affect the activity of the phospholipase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant phospholipase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., Current Protocols in Molecular Biology, 1992). Moreover, many expression vectors are commercially available that already encode a fusion moiety (e.g., a GST protein). A phospholipase peptide-encoding nucleic acid can be cloned into such an expression vector such that the fusion moiety is linked in-frame to the phospholipase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the phospholipase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)), using a NWSgapdna. CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10(1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the phospholipase peptides of the present invention as well as being encoded by the same genetic locus as the phospholipase peptide provided herein. The gene encoding the novel phospholipase protein of the present invention is located on a genome component that has been mapped to human chromosome 2 (as indicated in FIG. 3), which is supported by multiple lines of evidence, such as STS and BAC map data.

Allelic variants of a phospholipase peptide can readily be identified as being a human protein having a high degree (significant) of sequence homology/identity to at least a portion of the phospholipase peptide as well as being encoded by the same genetic locus as the phospholipase peptide provided herein. Genetic locus can readily be determined based on the genomic information provided in FIG. 3, such as the genomic sequence mapped to the reference human. The gene encoding the novel phospholipase protein of the present invention is located on a genome component that has been mapped to human chromosome 2 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a phospholipase peptide encoding nucleic acid molecule under stringent conditions as more fully described below.

FIG. 3 provides information on SNPs that have been found in the gene encoding the phospholipase protein of the present invention. SNPs were identified at 85 different nucleotide positions, including a non-synonymous coding SNP at position 3097 (protein position 33). The change in the amino acid sequence caused by this SNP is indicated in FIG. 3 and can readily be determined using the universal genetic code and the protein sequence provided in FIG. 2 as a reference. Some of these SNPs, particularly the three SNPs located 5' of the ORF, may affect control/regulatory elements.

Paralogs of a phospholipase peptide can readily be identified as having some degree of significant sequence homology/identity to at least a portion of the phospholipase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a phospholipase peptide encoding nucleic acid molecule under moderate to stringent conditions as more fully described below.

Orthologs of a phospholipase peptide can readily be identified as having some degree of significant sequence homology/identity to at least a portion of the phospholipase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a phospholipase peptide encoding nucleic acid molecule under moderate to stringent conditions, as more fully described below, depending on the degree of relatedness of the two organisms yielding the proteins.

Non-naturally occurring variants of the phospholipase peptides of the present invention can readily be generated using recombinant techniques. Such variants include, but are not limited to deletions, additions and substitutions in the amino acid sequence of the phospholipase peptide. For example, one class of substitutions are conserved amino acid substitution. Such substitutions are those that substitute a given amino acid in a phospholipase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant phospholipase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as phospholipase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the phospholipase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a phospholipase peptide. Such fragments can be chosen based on the ability to retain one or more of the biological activities of the phospholipase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the phospholipase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in phospholipase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the phospholipase peptides of the present invention also encompass derivatives or analogs in which a substituted amino acid residue is not one encoded by the genetic code, in which a substituent group is included, in which the mature phospholipase peptide is fused with another compound, such as a compound to increase the half-life of the phospholipase peptide (for example, polyethylene glycol), or in which the additional amino acids are fused to the mature phospholipase peptide, such as a leader or secretory sequence or a sequence for purification of the mature phospholipase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a phospholipase-effector protein interaction or phospholipase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, phospholipases isolated from humans and their human/mammalian orthologs serve as targets for identifying agents for use in mammalian therapeutic applications, e.g. a human drug, particularly in modulating a biological or pathological response in a cell or tissue that expresses the phospholipase. Experimental data as provided in FIG. 1 indicates that the phospholipase proteins of the present invention are expressed in humans in the kidney, blood, lung, brain glioblastomas, prostate, colon, and a mixed melanocyte/fetal heart/pregnant uterus sample, as indicated by virtual northern blot analysis. In addition, PCR-based tissue screening panels indicate expression in leukocytes. A large percentage of pharmaceutical agents are being developed that modulate the activity of phospholipase proteins, particularly members of the phospholipase B subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in the kidney, blood, lung, brain glioblastomas, prostate, colon, leukocytes, and a mixed melanocyte/fetal heart/pregnant uterus sample. Such uses can readily be determined using the information provided herein, that which is known in the art, and routine experimentation.

The proteins of the present invention (including variants and fragments that may have been disclosed prior to the present invention) are useful for biological assays related to phospholipases that are related to members of the phospholipase B subfamily. Such assays involve any of the known phospholipase functions or activities or properties useful for diagnosis and treatment of phospholipase-related conditions that are specific for the subfamily of phospholipases that the one of the present invention belongs to, particularly in cells and tissues that express the phospholipase. Experimental data as provided in FIG. 1 indicates that the phospholipase proteins of the present invention are expressed in humans in the kidney, blood, lung, brain glioblastomas, prostate, colon, and a mixed melanocyte/fetal heart/pregnant uterus sample, as indicated by virtual northern blot analysis. In addition, PCR-based tissue screening panels indicate expression in leukocytes.

The proteins of the present invention are also useful in drug screening assays, in cell-based or cell-free systems. Cell-based systems can be native, i.e., cells that normally express the phospholipase, as a biopsy or expanded in cell culture. Experimental data as provided in FIG. 1 indicates expression in humans in the kidney, blood, lung, brain glioblastomas, prostate, colon, leukocytes, and a mixed melanocyte/fetal heart/pregnant uterus sample. In an alternate embodiment, cell-based assays involve recombinant host cells expressing the phospholipase protein.

The polypeptides can be used to identify compounds that modulate phospholipase activity of the protein in its natural state or an altered form that causes a specific disease or pathology associated with the phospholipase. Both the phospholipases of the present invention and appropriate variants and fragments can be used in high-throughput screens to assay candidate compounds for the ability to bind to the phospholipase. These compounds can be further screened against a functional phospholipase to determine the effect of the compound on the phospholipase activity. Further, these compounds can be tested in animal or invertebrate systems to determine activity/effectiveness. Compounds can be identified that activate (agonist) or inactivate (antagonist) the phospholipase to a desired degree.

Further, the proteins of the present invention can be used to screen a compound for the ability to stimulate or inhibit interaction between the phospholipase protein and a molecule that normally interacts with the phospholipase protein, e.g. a substrate or a component of the signal pathway that the phospholipase protein normally interacts (for example, another phospholipase). Such assays typically include the steps of combining the phospholipase protein with a candidate compound under conditions that allow the phospholipase protein, or fragment, to interact with the target molecule, and to detect the formation of a complex between the protein and the target or to detect the biochemical consequence of the interaction with the phospholipase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant phospholipases or appropriate fragments containing mutations that affect phospholipase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) phospholipase activity. The assays typically involve an assay of events in the signal transduction pathway that indicate phospholipase activity. Thus, the phosphorylation of a substrate, activation of a protein, a change in the expression of genes that are up- or down-regulated in response to the phospholipase protein dependent signal cascade can be assayed.

Any of the biological or biochemical functions mediated by the phospholipase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the phospholipase can be assayed. Experimental data as provided in FIG. 1 indicates that the phospholipase proteins of the present invention are expressed in humans in the kidney, blood, lung, brain glioblastomas, prostate, colon, and a mixed melanocyte/fetal heart/pregnant uterus sample, as indicated by virtual northern blot analysis. In addition, PCR-based tissue screening panels indicate expression in leukocytes.

Binding and/or activating compounds can also be screened by using chimeric phospholipase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native phospholipase. Accordingly, a different set of signal transduction components is available as an end-point assay for activation. This allows for assays to be performed in other than the specific host cell from which the phospholipase is derived.

The proteins of the present invention are also useful in competition binding assays in methods designed to discover compounds that interact with the phospholipase (e.g. binding partners and/or ligands). Thus, a compound is exposed to a phospholipase polypeptide under conditions that allow the compound to bind or to otherwise interact with the polypeptide. Soluble phospholipase polypeptide is also added to the mixture. If the test compound interacts with the soluble phospholipase polypeptide, it decreases the amount of complex formed or activity from the phospholipase target. This type of assay is particularly useful in cases in which compounds are sought that interact with specific regions of the phospholipase. Thus, the soluble polypeptide that competes with the target phospholipase region is designed to contain peptide sequences corresponding to the region of interest.

To perform cell free drug screening assays, it is sometimes desirable to immobilize either the phospholipase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of phospholipase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a phospholipase-binding protein and a candidate compound are incubated in the phospholipase protein-presenting wells and the amount of complex trapped in the well can be quantitated. Methods for detecting such complexes, in addition to those described above for the GST-immobilized complexes, include immunodetection of complexes using antibodies reactive with the phospholipase protein target molecule, or which are reactive with phospholipase protein and compete with the target molecule, as well as enzyme-linked assays which rely on detecting an enzymatic activity associated with the target molecule.

Agents that modulate one of the phospholipases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of phospholipase protein activity identified according to these drug screening assays can be used to treat a subject with a disorder mediated by the phospholipase pathway, by treating cells or tissues that express the phospholipase. Experimental data as provided in FIG. 1 indicates expression in humans in the kidney, blood, lung, brain glioblastomas, prostate, colon, leukocytes, and a mixed melanocyte/fetal heart/pregnant uterus sample. These methods of treatment include the steps of administering a modulator of phospholipase activity in a pharnaceutical composition to a subject in need of such treatment, the modulator being identified as described herein.

In yet another aspect of the invention, the phospholipase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the phospholipase and are involved in phospholipase activity. Such phospholipase-binding proteins are also likely to be involved in the propagation of signals by the phospholipase proteins or phospholipase targets as, for example, downstream elements of a phospholipase-mediated signaling pathway. Alternatively, such phospholipase-binding proteins are likely to be phospholipase inhibitors.

The two-hybrid system is based on the modular nature of most transcription factors, which consist of separable DNA-binding and activation domains. Briefly, the assay utilizes two different DNA constructs. In one construct, the gene that codes for a phospholipase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a phospholipase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the phospholipase protein.

This invention further pertains to novel agents identified by the above-described screening assays. Accordingly, it is within the scope of this invention to further use an agent identified as described herein in an appropriate animal model. For example, an agent identified as described herein (e.g., a phospholipase-modulating agent, an antisense phospholipase nucleic acid molecule, a phospholipase-specific antibody, or a phospholipase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The phospholipase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in the kidney, blood, lung, brain glioblastomas, prostate, colon, leukocytes, and a mixed melanocyte/fetal heart/pregnant uterus sample. The method involves contacting a biological sample with a compound capable of interacting with the phospholipase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered phospholipase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the phospholipase protein in which one or more of the phospholipase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and phospholipase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in the kidney, blood, lung, brain glioblastomas, prostate, colon, leukocytes, and a mixed melanocyte/fetal heart/pregnant uterus sample. Accordingly, methods for treatment include the use of the phospholipase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the phospholipase proteins. Antibodies can be prepared from any region of the peptide as described herein. However, preferred regions will include those involved in function/activity and/or phospholipase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the phospholipase proteins of the present invention are expressed in humans in the kidney, blood, lung, brain glioblastomas, prostate, colon, and a mixed melanocyte/fetal heart/pregnant uterus sample, as indicated by virtual northern blot analysis. In addition, PCR-based tissue screening panels indicate expression in leukocytes. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in the kidney, blood, lung, brain glioblastomas, prostate, colon, leukocytes, and a mixed melanocyte/fetal heart/pregnant uterus sample. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in the kidney, blood, lung, brain glioblastomas, prostate, colon, leukocytes, and a mixed melanocyte/fetal heart/pregnant uterus sample. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in the kidney, blood, lung, brain glioblastomas, prostate, colon, leukocytes, and a mixed melanocyte/fetal heart/pregnant uterus sample. Thus, where a specific protein has been correlated with expression in a specific tissue, antibodies that are specific for this protein can be used to identify a tissue type.

The antibodies are also useful for inhibiting protein function, for example, blocking the binding of the phospholipase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a phospholipase peptide or protein of the present invention (cDNA, transcript and genomic sequence). Such nucleic acid molecules will consist of, consist essentially of, or comprise a nucleotide sequence that encodes one of the phospholipase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the phospholipase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the phospholipase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel phospholipase protein of the present invention is located on a genome component that has been mapped to human chromosome 2 (as indicated in FIG. 3), which is supported by multiple lines of evidence, such as STS and BAC map data.

FIG. 3 provides information on SNPs that have been found in the gene encoding the phospholipase protein of the present invention. SNPs were identified at 85 different nucleotide positions, including a non-synonymous coding SNP at position 3097 (protein position 33). The change in the amino acid sequence caused by this SNP is indicated in FIG. 3 and can readily be determined using the universal genetic code and the protein sequence provided in FIG. 2 as a reference. Some of these SNPs, particularly the three SNPs located 5' of the ORF, may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45 C, followed by one or more washes in 0.2×SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 85 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel phospholipase protein of the present invention is located on a genome component that has been mapped to human chromosome 2 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that the phospholipase proteins of the present invention are expressed in humans in the kidney, blood, lung, brain glioblastomas, prostate, colon, and a mixed melanocyte/fetal heart/pregnant uterus sample, as indicated by virtual northern blot analysis. In addition, PCR-based tissue screening panels indicate expression in leukocytes. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in phospholipase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a phospholipase protein, such as by measuring a level of a phospholipase-encoding nucleic acid in a sample of cells from a subject e.g., mRNA or genomic DNA, or determining if a phospholipase gene has been mutated. Experimental data as provided in FIG. 1 indicates that the phospholipase proteins of the present invention are expressed in humans in the kidney, blood, lung, brain glioblastomas, prostate, colon, and a mixed melanocyte/fetal heart/pregnant uterus sample, as indicated by virtual northern blot analysis. In addition, PCR-based tissue screening panels indicate expression in leukocytes.

Nucleic acid expression assays are useful for drug screening to identify compounds that modulate phospholipase nucleic acid expression.

The invention thus provides a method for identifying a compound that can be used to treat a disorder associated with nucleic acid expression of the phospholipase gene, particularly biological and pathological processes that are mediated by the phospholipase in cells and tissues that express it. Experimental data as provided in FIG. 1 indicates expression in humans in the kidney, blood, lung, brain glioblastomas, prostate, colon, leukocytes, and a mixed melanocyte/fetal heart/pregnant uterus sample. The method typically includes assaying the ability of the compound to modulate the expression of the phospholipase nucleic acid and thus identifying a compound that can be used to treat a disorder characterized by undesired phospholipase nucleic acid expression. The assays can be performed in cell-based and cell-free systems. Cell-based assays include cells naturally expressing the phospholipase nucleic acid or recombinant cells genetically engineered to express specific nucleic acid sequences.

The assay for phospholipase nucleic acid expression can involve direct assay of nucleic acid levels, such as mRNA levels, or on collateral compounds involved in the signal pathway. Further, the expression of genes that are up- or down-regulated in response to the phospholipase protein signal pathway can also be assayed. In this embodiment the regulatory regions of these genes can be operably linked to a reporter gene such as luciferase.

Thus, modulators of phospholipase gene expression can be identified in a method wherein a cell is contacted with a candidate compound and the expression of mRNA determined. The level of expression of phospholipase mRNA in the presence of the candidate compound is compared to the level of expression of phospholipase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate phospholipase nucleic acid expression in cells and tissues that express the phospholipase. Experimental data as provided in FIG. 1 indicates that the phospholipase proteins of the present invention are expressed in humans in the kidney, blood, lung, brain glioblastomas, prostate, colon, and a mixed melanocyte/fetal heart/pregnant uterus sample, as indicated by virtual northern blot analysis. In addition, PCR-based tissue screening panels indicate expression in leukocytes. Modulation includes both up-regulation (i.e. activation or agonization) or down-regulation (suppression or antagonization) or nucleic acid expression.

Alternatively, a modulator for phospholipase nucleic acid expression can be a small molecule or drug identified using the screening assays described herein as long as the drug or small molecule inhibits the phospholipase nucleic acid expression in the cells and tissues that express the protein.

Experimental data as provided in FIG. 1 indicates expression in humans in the kidney, blood, lung, brain glioblastomas, prostate, colon, leukocytes, and a mixed melanocyte/fetal heart/pregnant uterus sample.

The nucleic acid molecules are also useful for monitoring the effectiveness of modulating compounds on the expression or activity of the phospholipase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in phospholipase nucleic acid expression, and particularly in qualitative changes that lead to pathology. The nucleic acid molecules can be used to detect mutations in phospholipase genes and gene expression products such as mRNA. The nucleic acid molecules can be used as hybridization probes to detect naturally occurring genetic mutations in the phospholipase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the phospholipase gene associated with a dysfunction provides a diagnostic tool for an active disease or susceptibility to disease when the disease results from overexpression, underexpression, or altered expression of a phospholipase protein.

Individuals carrying mutations in the phospholipase gene can be detected at the nucleic acid level by a variety of techniques. FIG. 3 provides information on SNPs that have been found in the gene encoding the phospholipase protein of the present invention. SNPs were identified at 85 different nucleotide positions, including a non-synonymous coding SNP at position 3097 (protein position 33). The change in the amino acid sequence caused by this SNP is indicated in FIG. 3 and can readily be determined using the universal genetic code and the protein sequence provided in FIG. 2 as a reference. Some of these SNPs, particularly the three SNPs located 5' of the ORF, may affect control/regulatory elements. The gene encoding the novel phospholipase protein of the present invention is located on a genome component that has been mapped to human chromosome 2 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al, *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)).

This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a phospholipase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant phospholipase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. App.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the phospholipase gene in an individual in order to select an appropriate compound or dosage regimen for treatment. FIG. 3 provides information on SNPs that have been found in the gene encoding the phospholipase protein of the present invention. SNPs were identified at 85 different nucleotide positions, including a non-synonymous coding SNP at position 3097 (protein position 33). The change in the amino acid sequence caused by this SNP is indicated in FIG. 3 and can readily be determined using the universal genetic code and the protein sequence provided in FIG. 2 as a reference. Some of these SNPs, particularly the three SNPs located 5' of the ORF, may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control phospholipase gene expression in cells, tissues, and organisms. A DNA antisense nucleic acid molecule is designed to be complementary to a region of the gene involved in transcription, preventing transcription and hence production of phospholipase protein. An antisense RNA or DNA nucleic acid molecule would hybridize to the mRNA and thus block translation of mRNA into phospholipase protein.

Alternatively, a class of antisense molecules can be used to inactivate mRNA in order to decrease expression of phospholipase nucleic acid. Accordingly, these molecules can treat a disorder characterized by abnormal or undesired phospholipase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the phospholipase protein, such as substrate binding.

The nucleic acid molecules also provide vectors for gene therapy in patients containing cells that are aberrant in phospholipase gene expression. Thus, recombinant cells, which include the patient's cells that have been engineered ex vivo and returned to the patient, are introduced into an individual where the cells produce the desired phospholipase protein to treat the individual.

The invention also encompasses kits for detecting the presence of a phospholipase nucleic acid in a biological sample. Experimental data as provided in FIG. 1 indicates that the phospholipase proteins of the present invention are expressed in humans in the kidney, blood, lung, brain glioblastomas, prostate, colon, and a mixed melanocyte/fetal heart/pregnant uterus sample, as indicated by virtual northern blot analysis. In addition, PCR-based tissue screening panels indicate expression in leukocytes. For example, the kit can comprise reagents such as a labeled or labelable nucleic acid or agent capable of detecting phospholipase nucleic acid in a biological sample; means for determining the amount of phospholipase nucleic acid in the sample; and means for comparing the amount of phospholipase nucleic acid in the sample with a standard. The compound or agent can be packaged in a suitable container. The kit can further comprise instructions for using the kit to detect phospholipase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application W095/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application W095/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the phospholipase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the phospholipase gene of the present invention. FIG. 3 provides information on SNPs that have been found in the gene encoding the phospholipase protein of the present invention. SNPs were identified at 85 different nucleotide positions, including a non-synonymous coding SNP at position 3097 (protein position 33). The change in the amino acid sequence caused by this SNP is indicated in FIG. 3 and can readily be determined using the universal genetic code and the protein sequence provided in FIG. 2 as a reference. Some of these SNPs, particularly the three SNPs located 5' of the ORF, may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified phospholipase gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from E. coli, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual*. 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual*. 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli, Streptomyces,* and *Salmonella typhimurium*. Eukaryotic cells include, but are not limited to, yeast, insect cells such as *Drosophila*, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterophospholipase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli.* (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kujan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as phospholipases, appropriate secretion signals are incorporated into the vector. The signal sequence can be endogenous to the peptides or heterologous to these peptides.

Where the peptide is not secreted into the medium, which is typically the case with phospholipases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a phospholipase protein or peptide that can be further purified to produce desired amounts of phospholipase protein or fragments. Thus, host cells containing expression vectors are useful for peptide production.

Host cells are also useful for conducting cell-based assays involving the phospholipase protein or phospholipase protein fragments, such as those described above as well as other formats known in the art. Thus, a recombinant host cell expressing a native phospholipase protein is useful for assaying compounds that stimulate or inhibit phospholipase protein function.

Host cells are also useful for identifying phospholipase protein mutants in which these functions are affected. If the mutants naturally occur and give rise to a pathology, host cells containing the mutations are useful to assay compounds that have a desired effect on the mutant phospholipase protein (for example, stimulating or inhibiting function) which may not be indicated by their effect on the native phospholipase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a phospholipase protein and identifying and evaluating modulators of phospholipase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the phospholipase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the phospholipase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, phospholipase protein activation, and signal transduction, may not be evident from in vitro cell-free or cell-based assays. Accordingly, it is useful to provide non-human transgenic animals to assay in vivo phospholipase protein function, including substrate interaction, the effect of specific mutant phospholipase proteins on phospholipase protein function and substrate interaction, and the effect of chimeric phospholipase proteins. It is also possible to assess the effect of null mutations, that is, mutations that substantially or completely eliminate one or more phospholipase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

What is claimed is:

1. An isolate nucleic acid molecule consisting of a nucleotide sequence selected from the group consisting of:

(a) a nucleotide sequence consisting of SEQ ID NO; 1;
   (b) a nucleotide sequence consistina of SEQ ID NO: 3; and
   (c) a nucleotide sequence that is completely complementary to a nucleotide sequence of (a)–(b).

2. A nucleic acid vector comprising a nucleic acid molecule of claim 1.

3. A host cell containing the vector of claim 2.

4. A process for producing a polypeptide comprising culturing the host cell of claim 3 under conditions sufficient for the production of said polypeptide, and recovering said polypeptide.

5. An isolated polynucleotide consisting of the nucleotide sequence set forth in SEQ ID NO:1.

6. An isolated polynucleotide consisting of the nucleotide sequence set forth in SEQ ID NO:3.

7. A vector according to claim 2, wherein said vector is selected from the group consisting of a plasmid, a virus, and a bacteriophage.

8. A vector according to claim 2, wherein said isolated nucleic acid molecule is inserted into said vector in proper orientation and correct reading frame such that a polypeptide comprising SEQ ID NO:2 may be expressed by a cell transformed with said vector.

9. A vector according to claim 8, wherein said isolated nucleic acid molecule is operatively linked to a promoter sequence.

* * * * *

SEQUENCE LISTING

<160> NUMBER OF SEQ ID NOS: 3

<210> SEQ ID NO 1
<211> LENGTH: 1835
<212> TYPE: DNA
<213> ORGANISM: Homo sapiens

<400> SEQUENCE: 1

```
ctgcagccaa ctttgttgac catctccgca atgccttgga cgtcctgcat agagagcttt      60
tcccttaggt gcccagagtc ctggtcaacc tcgtggactt cctgaacccc actatcatgc     120
ggcaggtgtt cctgggaaac ccagacaagt gcccagtgca gcaggccaga gcagcatgcg     180
cgagctggtg gggtcaggcc gctatgacac gcaggaggac ttctctgtgg tgctgcagcc     240
cttcttccag aacatccagc tccctgtcct ggcgcttgaa ccacttggaa gcaaaacaga     300
gaccctggac ctgagagcag agatgcccat cacctgtccc actcagaatg agcccttcct     360
gagaacccct cggaatagta actacacgta ccccatcaag ccagccattg agaactgggg     420
cagtgacttc ctgtgtacag agtggaaggc ttccaatagt gttccaacct ctgtccacca     480
gctccgacca gcagacatca aagtggtggc cgccctgggt gactctctga ctacagcagt     540
gggagctcga ccaaacaact ccagtgacct acccacatct tggaggggac tctcttggag     600
```

-continued

```
cattggaggg gatgggaact tggagactca caccacactg cccaacattc tgaagaagtt    660
caaccCttac ctccttggct tctctaccag cacctgggag gggacagcag gactaaatgt    720
ggcagcggaa ggggccagag ctagggacat gccagcccag gcctgggacc tggtagagcg    780
aatgaaaaac agccccgaca tcaacctgga gaaagactgg aagctggtca cactcttcat    840
tggggtcaac gacttgtgtc attactgtga gaatccggag gcccacttgg ccacggaata    900
tgttcagcac atccaacagg ccctggacat cctctctgag gagctcccaa gggctttcgt    960
caacgtggtg gaggtcatgg agctggctag cctgtaccag ggccaaggcg ggaaatgtgc   1020
catgctggca gctcagaaca actgcacttg cctcagacac tcgcaaagct ccctggagaa   1080
gcaagaactg aagaaagtga actggaacct ccagcatggc atctccagtt tctcctactg   1140
gcaccaatac acacagcgtg aggactttgc ggttgtggtg cagcctttct tccaaaacac   1200
actcacccca ctgaacgaga gagggcacac tgacctcacc ttcttctccg aggactgttt   1260
tcacttctca gaccgcgggc atgccgagat ggccatcgca ctctggaaca acatgctgga   1320
accagtgggc cgcaagacta cctccaacaa cttcacccac agccgagcca aactcaagtg   1380
cccctctcct gagagccctt acctctacac cctgcggaac agccgattgc tcccagacca   1440
ggctgaagaa gcccccgagg tgctctactg ggctgtccca gtggcagcgg gagtcggcct   1500
tgtggtgggc atcatcggga cagtggtctg gaggtgcagg agaggtggcc ggagggaaga   1560
tcctccaatg agcctgcgca ctgtggcccT ctaggcccgg gggtgggtcc tcaccctaaa   1620
ctccctatag ccactctctt caccgccctc tgccccagcc actcccggcc accaggacat   1680
gcttcaatgc ctggtgccat aggaagccca ggggacagtc acaacttctt ggggcctggg   1740
cttcttccag gcctatgctc ctggaatgga tacatttaaa taaagtccaa agctatttta   1800
aaaaaaaaaa aaaaaaaaaa aaaaaaaaaa aaaaa                              1835
```

<210> SEQ ID NO 2
<211> LENGTH: 472
<212> TYPE: PRT
<213> ORGANISM: Homo sapiens

<400> SEQUENCE: 2

Met Arg Glu Leu Val Gly Ser Gly Arg Tyr Asp Thr Gln Glu Asp Phe
 1               5                  10                  15

Ser Val Val Leu Gln Pro Phe Phe Gln Asn Ile Gln Leu Pro Val Leu
                20                  25                  30

Ala Leu Glu Pro Leu Gly Ser Lys Thr Glu Thr Leu Asp Leu Arg Ala
            35                  40                  45

Glu Met Pro Ile Thr Cys Pro Thr Gln Asn Glu Pro Phe Leu Arg Thr
        50                  55                  60

Pro Arg Asn Ser Asn Tyr Thr Tyr Pro Ile Lys Pro Ala Ile Glu Asn
 65                 70                  75                  80

Trp Gly Ser Asp Phe Leu Cys Thr Glu Trp Lys Ala Ser Asn Ser Val
                85                  90                  95

Pro Thr Ser Val His Gln Leu Arg Pro Ala Asp Ile Lys Val Val Ala
               100                 105                 110

Ala Leu Gly Asp Ser Leu Thr Thr Ala Val Gly Ala Arg Pro Asn Asn
           115                 120                 125

Ser Ser Asp Leu Pro Thr Ser Trp Arg Gly Leu Ser Trp Ser Ile Gly
       130                 135                 140

Gly Asp Gly Asn Leu Glu Thr His Thr Thr Leu Pro Asn Ile Leu Lys

```
                145                 150                 155                 160
Lys Phe Asn Pro Tyr Leu Leu Gly Phe Ser Thr Ser Thr Trp Glu Gly
                165                 170                 175

Thr Ala Gly Leu Asn Val Ala Ala Glu Gly Ala Arg Ala Arg Asp Met
            180                 185                 190

Pro Ala Gln Ala Trp Asp Leu Val Glu Arg Met Lys Asn Ser Pro Asp
            195                 200                 205

Ile Asn Leu Glu Lys Asp Trp Lys Leu Val Thr Leu Phe Ile Gly Val
            210                 215                 220

Asn Asp Leu Cys His Tyr Cys Glu Asn Pro Glu Ala His Leu Ala Thr
225                 230                 235                 240

Glu Tyr Val Gln His Ile Gln Gln Ala Leu Asp Ile Leu Ser Glu Glu
                245                 250                 255

Leu Pro Arg Ala Phe Val Asn Val Val Glu Val Met Glu Leu Ala Ser
            260                 265                 270

Leu Tyr Gln Gly Gln Gly Gly Lys Cys Ala Met Leu Ala Ala Gln Asn
            275                 280                 285

Asn Cys Thr Cys Leu Arg His Ser Gln Ser Ser Leu Glu Lys Gln Glu
290                 295                 300

Leu Lys Lys Val Asn Trp Asn Leu Gln His Gly Ile Ser Ser Phe Ser
305                 310                 315                 320

Tyr Trp His Gln Tyr Thr Gln Arg Glu Asp Phe Ala Val Val Val Gln
                325                 330                 335

Pro Phe Phe Gln Asn Thr Leu Thr Pro Leu Asn Glu Arg Gly Asp Thr
            340                 345                 350

Asp Leu Thr Phe Phe Ser Glu Asp Cys Phe His Phe Ser Asp Arg Gly
            355                 360                 365

His Ala Glu Met Ala Ile Ala Leu Trp Asn Asn Met Leu Glu Pro Val
            370                 375                 380

Gly Arg Lys Thr Thr Ser Asn Asn Phe Thr His Ser Arg Ala Lys Leu
385                 390                 395                 400

Lys Cys Pro Ser Pro Glu Ser Pro Tyr Leu Tyr Thr Leu Arg Asn Ser
            405                 410                 415

Arg Leu Leu Pro Asp Gln Ala Glu Glu Ala Pro Glu Val Leu Tyr Trp
            420                 425                 430

Ala Val Pro Val Ala Ala Gly Val Gly Leu Val Val Gly Ile Ile Gly
            435                 440                 445

Thr Val Val Trp Arg Cys Arg Arg Gly Gly Arg Glu Asp Pro Pro
            450                 455                 460

Met Ser Leu Arg Thr Val Ala Leu
465                 470

<210> SEQ ID NO 3
<211> LENGTH: 43543
<212> TYPE: DNA
<213> ORGANISM: Homo sapiens
<220> FEATURE:
<221> NAME/KEY: misc_feature
<222> LOCATION: (1)...(43543)
<223> OTHER INFORMATION: n = A,T,C or G

<400> SEQUENCE: 3
attctgcagc caactttgtt gaccatctcc gcaatgcctt ggacgtcctg catagagagg      60
tgggtggggg gcttccacaa gctggtaaca gctcaagcat ggtgagggtg aaggtggatg     120
gggggaaaga atgagagaag aaccccttc tctcaaggag acagccaagg gcatggannn     180
```

```
nnnnnnnnnn nnnnnnnnnn nnnnnnnnnn nnnnnnnnnn nnnnnnnnnn nnnnnnnnnn    240
nnnnnnnnnn nnnnnnnnnn nnnnnnnnnn nnnnnnnnnn nnnnnnnnnn nnnnnnnnnn    300
nnnnnnnnnn nnnnnnnnnn nnnnnnnnnn nnnnnnnnnn nnnnnnnnnn nnnnnnnnnn    360
nnnnnnnnnn nnnnnnnnnn nnnnnnnnnn nnnnnnnnnn nnnnnnnnnn nnnnnnnnnn    420
nnnnnnnnnn nnnnnnnnnn nnnnnnnnnn nnnnnnnnnn nnnnnnnnnn nnnnnnnnnn    480
nnnnnnnnnn nnnnnnnnnn nnnnnnnnnn nnnnnnnnnn nnnnnnnnnn nnnnnnnnnn    540
nnnnnnnnnn nnnnnnnnnn nnnnnnnnnn nnnnnnnnnn nnnnnnnnnn nnnnnnnnnn    600
nnnnnnnnnn nnnnnnnnnn nnnnnnnnnn nnnnnnnnnn nnnnnnnnnn nnnnnnnnnn    660
nnnnnnnnnn nnnnnnnnnn nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
nnnnnnnnnn nnnnnnnnnn nnnnnnnnnn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn ngtgccattg ccgctgcagc    960
cccctttgggt ggcacccatg gagttgtgtg atgtacggcc tgtaaggcct tacgaggtag   1020
ccctgtatag actcctcccc agaactcaac tccagaaaga ccaagctgga ttgctaaagg   1080
aacccattcc tagggccct gagacagccc caggaagaag tgcctggagc ccccctctca   1140
tctgcagctt ttcccttagg tgcccagagt cctggtcaac ctcgtggact tcctgaaccc   1200
cactatcatg cggcaggtgt tcctgggaaa cccagacaag tgcccagtgc agcaggccag   1260
gtaggcaggt cctggctgtc cccacactgg agatgccctc acctcctggt ctggcccaca   1320
tgcagtggtg atgcctcagg gtctttgtga cttggtctat ccatgtgtcc aagtctgtaa   1380
aggaggactt ctgccagaac gtccccttcc agaggctgga gccatgactc ccctgttacc   1440
caacttcaag gtgcctggca ggaacttcta tgataccagg cagccacaga ggggagggat   1500
caaagttggg acagaggctg gtgtttgaga gacaggatag cctagactgt gaacatgggc   1560
agtggttagg gatgtagaca tatgtggtca aactgtaaca gaaagcaagg aaaaggtaca   1620
agcaactcag ttacctttag gggaagaaga gaattaggag ggacacaggg agcttcaaac   1680
tgggagtgtt ttgtttctta aactgggcca taagtacatg gatgtgtgtt ttattattct   1740
ttatatctta cacatctatt tactcagcaa atcttacaga acttcctgtg taccaggcat   1800
tgtttcaagt gctttagaaa tctctctctt aagtagatgt gatgggtgtg aaataattca   1860
tgatgaaacc aaaggggaca cagtagggca ctcatgtgaa agaaggagag gtctaaggca   1920
tagcatcaga ggccccaaaa tatcagctcc aacaccagag gatgcatttt cttttttaatt   1980
aaacactaaa ttttcactgc ccaaattcat ttgctcagct gaataatcgg ttgcaggccc   2040
agcacctgca gtccaacact tgtgctctgt tggtatgaga gggtgctcat tcccacgctg   2100
gctccctccc tcgggccatc tccagtgccc ctgccaggcc tgaagcctgc ccctgagcat   2160
gtgcgccaga gcctcaaggc ttgagtgctc ctaaaccagg gcgggaggga gcctctccac   2220
ccctcccctg aacctgggca atcagaacca gcccctgatg gaagcctgag ctctggggcc   2280
tcctgcctcc ccctctttgt gcagcgtttt gtgtaactgc gttctgaccc tgcgggagaa   2340
ctcccaagag ctagccaggc tggaggcctt cagccgagcc taccgggtaa gaccaagaag   2400
ggcaccatgc tgtgtcctct cccctacgtt cactctaaca cacagcccag agccctaga   2460
ggaggcacac agggaaggaa aagctggtca gggattgtgg ggagacgggg agcagcctgg   2520
```

```
gtgccttcct ctgtctcacg tgactgtggt gtctcaggtg ccctggttgg aatcatccca    2580
gtaggatcca ggtggaaaag ccctcatggc ccagctaccg ttgagggctt aaccccaact    2640
cctggcccgt agccctggat gcctcatgag accacctttc cctcccccac tcccactcca    2700
aaggcaggtg ccgagcctct ggaggttctt cccaggtttt tatccctttt gggacttcct    2760
gcctagccct tcagagagag tagtctactt acaatcaaaa caaaaaggtg acccaacctg    2820
tttccaaatt ctctggaaag ggacttgccc tcaggtgatt tgtgttctca agggaaaggc    2880
tgagtcggcc cctccatcca gggagatgga ctgcccacca cccctactct tgcctcactg    2940
ggtcctgggc ccacccaggg cctgggctga agaccctgtg catgtgtccc cagagcagca    3000
tgcgcgagct ggtggggtca ggccgctatg acacgcagga ggacttctct gtggtgctgc    3060 agccttctt ccagaacatc cagctccctg tcctggtggt atgtccctg ccctcgccca     3120 tggtactctt ttagaggaag aaatgcaagg cagaattgcc agttgcttcc acgagcatgt    3180
gcataaaatg ggaaagacac agctctccag acgctgnnnn nnnnnnnnnn nnnnnnnnnn    3240
nnnnnnnnnn nnnnnnnnnn nnnnnnnnnn nnnnnnnnnn nnnnnnnnnn nnnnnnnnnn    3300
nnnnnnnnnn nnnnnnnnnn nnnnnnnnnn nnnnnnnnnn nnnnnnnnnn nnnnnnnnnn    3360
nnnnnnnnnn nnnnnnnnnn nnnnnnnnnn nnnnnnnnnn nnnnnnnnnn nnnnnnnnnn    3420
nnnnnnnnnn nnnnnnnnnn nnnnnnnnnn nnnnnnnnnn nnnnnnnnnn nnnnnnnnnn    3480
nnnnnnnnnn nnnnnnnnnn nnnnnnnnnn nnnnnnnnnn nnnnnnnnnn nnnnnnnnnn    3540
nnnnnnnnnn nnnnnnnnnn nnnnnnnnnn nnnnnnnnnn nnnnnnnnnn nnnnnnnnnn    3600
nnnnnnnnnn nnnnnnnnnn nnnnnnnnnn nnnnnnnnnn nnnnnnnnnn nnnnnnnnnn    3660
nnnnnnnnnn nnnnnnnnnn nnnnnnnnnn nnnnnnnnnn nnnnnnnnnn nnnnnnnnnn    3720
nnnnnnnnnn nnnnnnnnnn nnnnnnnnnn ttgtgggatc gctctgatct ctctgttaag    3780
tgaatgggcc ctgtggtggc tggtgacctg gagcactcca ggggaaggaa ggtgttgagt    3840
ggtcagtccc agggccaagt ccgctggtgg tggctccctc tgaaccaata ggatcttgag    3900
ggggtatatt ggtctctttc aggatgggct cccagatacg tccttctttg ccccagactg    3960
catccaccca aatcagaaat tccactccca gctggccaga gcccttggga ccaatatggt    4020
aaaataagtg gggtgttcct tgttctctgg ggttctagtc tagggcaggg caccagcccc    4080
tatagaatgg agtcttgcaa gtgaggctga gggggcagtg gctggtacat ctataaacgt    4140
ctatgcagtt ggaaatgcgg agtccttaag agtctgctca gcctgggctc aactgcaccc    4200
tctcctcaga gctttgaact ctgaggaggg acctctctac agaaatgcaa gcccaaaacc    4260
ccatattcat tccactttcc ctatgtgccg gccaccatgt taggcagttt aagccacgtt    4320
atctcattta aggctctgca tatccctgct agagaagcat gacgagtctc caaggaagct    4380
actcccagag aagcaaagcg actggcccaa aaccccacgg ctggcaactg gcagagccag    4440
aagtgggagc caagccccct gaaatcgagt tctgagcttt ccccactgca ggattctgcc    4500
agggaatgtt cacttccatg gaaacaaact actacacccg tgtctctctt ttcttccctg    4560
atcagcttga accacttgga agcaaaacag agacctggga cctgagagca gagatgccca    4620
tcacctgtcc cactcaggta gtaggggagg acctgcctgg ctcctctcca caaaccaggg    4680
cacacagctc gccctaccca cttcgtcctc caccacagct tcctcagtac ccatcttgcc    4740
cccttactga ggcctgagag atttggagga tgagggggag tccatgagga tggacagggg    4800
aggtgagagg ggagacaaga gtgcagctgt cattgggaac aggagatgca gcagggagag    4860
gaggcctggg ccccagcaga gggagaggat cccggtgaga aaagtgggct cctgagagag    4920
```

```
gaaatcagga tgccaggaaa atggcaggag ggcttctctt agcagtggtg tttggggcag    4980
atgaaaaaat ctgactgcag gttagagggc ccaggcagga gccaggcagg cttaagagct    5040
gtggttggag agaggagagc ctggattagg gagattccac aaggaaagga tcacagagga    5100
cagcagcaaa gggcagagcc cagagctgta tggaggaggg acgagggtgg gcctaccagg    5160
acacggcagc tccaggctcc ttttaaggag gaatccgtaa gtggttgtta agcttgactt    5220
caggcctggg gtgggggcag gttctcattg tcttcagctc ctgtttctag gcccggtctt    5280
atggcttttt aaccaaataa ggccaaggcc agaaaaccct cagcagcaat aaaagcagaa    5340
ggcctgaccc aatctgggag gctgggtttc cctcctaggt cggccacacc accctctccc    5400
accctccctg ctgggaatg gacctgcagc tcccccatgt gtctgctggg aatcctgaga    5460
gagtgggcac ccctgttcac atgcctgctc cctgtctgct gcctgcccta ccccagtctt    5520
gggctcaggc tcagtcttgt gtgccatcag ccccatcagg agagcaagaa tggcaggaag    5580
aagggatggg aagtgaagac agtcgtagca gagggctcag ttgctgggtc ttgtgcttgg    5640
agctaaggag attgtcagat tctgcaacag ctagtgcaac acagatgcct ctagtccagg    5700
tggtcaggtg ctggccaaag gcctggagca aaaccttaga ggcccctact gtgccaggtg    5760
taaactcttt aactgctttc ctaaggatgc cttgggggtt ctaggggagc agccagggac    5820
cgtggatagt gggggcattt ggggactcag aaatagccat attgtagata tttcaatatt    5880
ttaccaaccc tatagccata ctgaatatca gccatggagg gccctttcca aactgtccac    5940
tccccttcca ttacataaca aaagcagcca tcatttgctc tttctttcaa caaacgtgta    6000
ttgagtactg agttggagcc taagcactgg gtcagggaga gccctgtcac cctgggcttc    6060
gaggcaacca cttccaggct ttaccccaga tcaggcagag accccaaaaa ggaggctgct    6120
ccacccagca gcatcttaag ctgagtgggc tcagtgcctc ccttctagac agagcccaat    6180
ggagccactg cactgatttg cagaggtgag cagatccagc ctcgtggaac cagtagaagc    6240
ccagccctgg tgaagctgtt gctaagcaac attggagccc attctgaaag ggtccatctg    6300
ttggccagcc caacttcact gtgttctgag cattctgcat tcctcagtcc catctgctcc    6360
ctcccatgtg ccttggagtg atataaaagt ccaccagcat ctcagtgtga gctgacaggg    6420
gccaggcagc acctattttt gtcctagatg tgtctaaaca tagaggcaac aggcaacagg    6480
caagacgcag tgggggggcgg gaggcaggag gccgagatgg ctgtgagcat gagctttctc    6540
agcctcctcc cttctcccat ccgcagtcta actgctcata cgttctgtgt gccaggtagg    6600
gtgacttaac agcacgccat ggatttctgt tgtagtttca agttggacaa attctttttac    6660 agacaacttt tgactagcct tctgtggact gagcctatac tctgccttaa tgggctctct    6720
gcccactcct ttcctaaccc cagggcagct ggctgaacac ctggtccttt tcttaggttt    6780
cattcttttt gacctctctg aagcccttgt caaaagtcac cacctccccc ttgaaattca    6840
ctccttcctg ggtttgtgga cactaaatcg ccttgatttt tctggtcttc tgtttgcttg    6900
cctttaatga ccctcctcct ccctttcccc agtcttgaaa atgtagatat tctccaattt    6960
tcatgtctcc attctatttt ctttcctttt tcactcactt tttgaaacag ggtcttgctc    7020
cgtctcccag gctggaagtg cagtggcgca atcacagctc tctgcagctt caactccta    7080 ggctcaagcc atcctcccac ctcagcttcc tgagtagttg ggactgcagg catgcaccac    7140
catgcccagc taattttggt ttatttgttt tggtagaggg ggggtcttgc cattttggct    7200
caggctgatt ttgaactctg gnnnnnnnnn nnnnnnnnnn nnnnnnnnnn nnnnnnnnnn    7260
```

-continued

```
nnnnnnnnnn nnnnnnnnnn nnnnnnnnnn nnnnnnnnnn nnnnnnnnnn nnnnnnnnnn      7320
nnnnnnnnnn nnnnnnnnnn nnnnnnnnnn nnnnnnnnnn nnnnnnnnnn nnnnnnnnnn      7380
nnnnnnnnnn nnnnnnnnnn nnnnnnnnnn nnnnnnnnnn nnnnnnnnnn nnnnnnnnnn      7440
nnnnnnnnnn nnnnnnnnnn nnnnnnnnnn nnnnnnnnnn nnnnnnnnnn nnnnnnnnnn      7500
nnnnnnnnnn nnnnnnnnnn nnnnnnnnnn nnnnnnnnnn nnnnnnnnnn nnnnnnnnnn      7560
nnnnnnnnnn nnnnnnnnnn nnnnnnnnnn nnnnnnnnnn nnnnnnnnnn nnnnnnnnnn      7620
nnnnnnnnnn nnnnnnnnnn nnnnnnnnnn nnnnnnnnnn nnnnnnnnnn nnnnnnnnnn      7680
nnnnnnnnnn nnnnnnnnnn nnnnnnnnnn nnnnnnnnnn nnnnnnnnnn nnnnnnnnnn      7740
nnnnnnnnnn nnnnnnnnnn nnnnnnnnnn nnnnnnnnnn nnnnnnnnnn nnnnnnnnnn      7800
nnnnnnnnnn nnnnnnnnnn nnnnnnnnnn nnnnnnnnnn nnnnnnnnnn nnnnnnnnnn      7860
nnnnnnnnnn nnnnnnnnnn nnnnnnnnnn nnnnnnnnnn nnnnnnnnnn nnnnnnnnnn      7920
nnnnnnnnnn nnnnnnnnnn nnnnnnnnnn nnnnnnnnnn nnnnnnnnnn nnnnnnnnnn      7980
nnnnnnnnnn nnnnnnnnnn nnnnnnnnnn nnnnnnnnnn nnnnnnnnnn nnnnnnnnnn      8040
nnnnnnnnnn nnnnnnnnnn nnnnnnnnnn nnnnnnnnnn nnnnnnnnnn nnnnnnnnnn      8100
nnnnnnnnnn nnnnnnnnnn nnnnnnnnnn nnnnnnnnnn nnnnnnnnnn nnnnnnnnnn      8160
nnnnnnnnnn nnnnnnnnnn nnnnnnnnnn nnnnnnnnnn nnnnnnnnnn nnnnnnnnnn      8220
nnnnnnnnnn nnnnnnnnnn nnnnnnnnnn nnnnnnnnnn nnnnnnnnnn nnnnnnnnnn      8280
nnnnnnnnnn nnnnnnnnnn nnnnnnnnnn nnnnnnnnnn nnnnnnnnnn nnnnnnnnnn      8340
nnnnnnnnnn nnnnnnnnnn nnnnnnnnnn nnnnnnnnnn nnnnnnnnnn nnnnnnnnnn      8400
nnnnnnnnnn nnnnnnnnnn nnnnnnnnnn nnnnnnnnnn nnnnnnnnnn nnnnnnnnnn      8460
nnnnnnnnnn nnnnnnnnnn nnnnnnnnnn nnnnnnnnnn nnnnnnnnnn nnnnnnnnnn      8520
nnnnnnnnnn nnnnnnnnnn nnnnnnnnnn nnnnnnnnnn nnnnnnnnnn nnnnnnnnnn      8580
nnnnnnnnnn nnnnnnnnnn nnnnnnnnnn nnnnnnnnnn nnnnnnnnnn nnnnnnnnnn      8640
nnnnnnnnnn nnnnnnnnnn nnnnnnnnnn nnnnnnnnnn nnnnnnnnnn nnnnnnnnnn      8700
nnnnnnnnnn nnnnnnnnnn nnnnnnnnnn nnnnnnnnnn nnnnnnnnnn nnnnnnnnnn      8760
nnnnnnnnnn nnnnnnnnnn nnnnnnnnnn nnnnnnnnnn nnnnnnnnnn nnnnnnnnnn      8820
nnnnnnnnnn nnnnnnnnnn nnnnnnnnnn nnnnnnnnnn nnnnnnnnnn nnnnnnnnnn      8880
nnnnnnnnnn nnnnnnnnnn nnnnnnnnnn nnnnnnnnnn nnnnnnnnnn nnnnnnnnnn      8940
nnnnnnnnnn nnnnnnnnnn nnnnnnnnnn nnnnnnnnnn nnnnnnnnnn nnnnnnnnnn      9000
nnnnnnnnnn nnnnnnnnnn nnnnnnnnnn nnnnnnnnnn nnnnnnnnnn nnnnnnnnnn      9060
nnnnnnnnnn nnnnnnnnnn nnnnnnnnnn nnnnnnnnnn nnnnnnnnnn nnnnnnnnnn      9120
nnnnnnnnnn nnnnnnnnnn nnnnnnnnnn nnnnnnnnnn nnnnnnnnnn nnnnnnnnnn      9180
nnnnnnnnnn nnnnnnnnnn nnnnnnnnnn nnnnnnnnnn nnnnnnnnnn nnnnnnnnnn      9240
nnnnnnnnnn nnnnnnnnnn nnnnnnnnnn nnnnnnnnnn nnnnnnnnnn nnnnnnnnnn      9300
nnnnnnnnnn nnnnnnnnnn nnnnnnnnnn nnnnnnnnnn nnnnnnnnnn nnnnnnnnnn      9360
nnnnnnnnnn nnnnnnnnnn nnnnnnnnnn nnnnnnnnnn nnnnnnnnnn nnnnnnnnnn      9420
nnnnnnnnnn nnnnnnnnnn nnnnnnnnnn nnnnnnnnnn nnnnnnnnnn nnnnnnnnnn      9480
nnnnnnnnnn nnnnnnnnnn nnnnnnnnnn nnnnnnnnnn nnnnnnnnnn nnnnnnnnnn      9540
nnnnnnnnnn nnnnnnnnnn nnnnnnnnnn nnnncaataa acccagctaa aaacaagccc      9600
aataaaaccc aataaaaccc attagacagg aacataggag ttggaaaaaa aagaaaagaa      9660
```

-continued

| | |
|---|---|
| ggggaggggg aagaaagccc tgaggcaccc cggctgcctg tctgccacaa ccctgggctg | 9720 |
| taattgttct tgccatggcc tcagtctgca acacattcta gtgtctcctt gacctctagc | 9780 |
| cctctagctc tgcctcccct tccccaacct gtagatcttg tgatcaaata gattcaatga | 9840 |
| aacacattgt ccagttgcac tcgcagcact tccaaaaagg tcaagtttgt ccttccctca | 9900 |
| gtgcctccca ttctggtcac ggtaggactg actccagccc ctggacccta agctgagtct | 9960 |
| gggctccttt gacgtgcagg gagaatgcca ctgagtcttg tctctgagga ccctacctct | 10020 |
| ccaaatcttg cctcagttcc tcagcaggta ctacactgac tggccatgcc attctctgat | 10080 |
| gcttcactgc ctcagcttct caagtctgtc tccccacctg agccaattgt gagtttctct | 10140 |
| ctctcctcct ctcatcctgg cacctagaaa tgctctctaa cgcttgagct gctcaaccag | 10200 |
| catgggtcac ttgtttatag catgctccca gatcgccctc tttgttggtg aatgctcagg | 10260 |
| gaatgcttac tgttaacccg agacaagccc aagtagctac atggacctgc caccataagc | 10320 |
| cctctcctgt cttatgctgt tgtagagggt ccagggctca cttctcccac ttggccctga | 10380 |
| gtacctctcc ttgaaaggat gtcagggggct gggcgcagtg gctcacgtct gtaaccccag | 10440 |
| cactttggga ggctgaggcg gcggatcac caggtcagga gatcgagacc atcctggcta | 10500 |
| acatggtgaa ccccccgtct ctactaaaaa tacaaaaaat aaaaatagcc atttgtggtg | 10560 |
| gcaggtgcct gtagtcccag ctactcggga ggctgaggca ggaaaatggc atgaacccag | 10620 |
| aaggcagagc ttgcagtgag ccagatcgc gccactgcac tccagcctgg caacagagc | 10680 |
| aagactccgt ctcaaaaaag caagcaagaa agaaaggata tcggttacct gtttcagaca | 10740 |
| ggaatgctga gaccagggaa agggagact tgtcgggtgc ctcagggaac cagtatctga | 10800 |
| gctgggggct gagagctctg tgtgggtgga ctctgtcctc ccagtcgctg ctgagtccct | 10860 |
| ctcttccttt cccgctgtct gaccaacagg ttttttgttg gcctgacctc cagtgtgagg | 10920 |
| aacgaaacca ggcaagaggc ttgtccagtc agctctggcc ccagtttggc attcatcact | 10980 |
| tgttccctaa cctggaaccc gtcccttcct cactctgggg ctcagcagct gctcatctat | 11040 |
| aaagtggggc atttgggggt tgcaaagtca gtcatctaca atgccaggca agaacatggt | 11100 |
| tgcgtacatg tggtcaggta tgagacgaga tcacttttcc aacattctgg ttttcccttt | 11160 |
| tttttttttt tttgaaacag agtccttgctc tgttacccag actggagtga actggcatga | 11220 |
| tctcatctta ctgcaacccc tgcctcccag gttcaaacaa ttctcatgcc tcaacctctc | 11280 |
| aagtagctga gattacagat gtgtaccaca cctggatttt ttttttttt tttttttgtat | 11340 |
| ttttagtaga gacagggttt caccatgttg tccaggctgg tcttgaactc ttggcctcat | 11400 |
| gtgatgaacc ccccccttggc ctcccaaagt gctgggggtta caggtgtgag ccactgtgcc | 11460 |
| cagactaatt ttttttttttt tattgaaaca gagtctcact ctgttgccca ggctggagtg | 11520 |
| cactggcaca attatagctc actgtaacca caaactcctg ggttcaagca atccttctgc | 11580 |
| ttcagcctct tgagtagcta ggattacagg cacatgccac catgttgagc taatttattt | 11640 |
| ttttaatttg tcgtagagat ggggtcttgc tatgcttccc aagctggtat taaactcttg | 11700 |
| gccccaagca atcctcctac cctggcctcc caaaacgctg ggaatacagg catgggccac | 11760 |
| tgtgccagcc tggttttttc ttcttgttcc cattttattc tcacattttc agaccatggg | 11820 |
| cttactactc cactgagcac attttgtgag agtgctcaca gccctgggcc cggttgctgt | 11880 |
| ttcctgatct cagtcttatc aacttgatct tgctttgctg tcatttatac attttctcat | 11940 |
| tagctttctc cccatttctt ctttgtctgc ttccttcttc cttctttaac taactcctca | 12000 |

```
cctgcaactg gggggacttg gattcttgac tgggcttgtg tgaaaactga ttgtaaaaca   12060
gataggtaag tagggaatga ggagggtgtt ttacaagaaa aaaaaaatga ctaagataca   12120
ggaacccaac ctaaagagga aaagacatac agttcaaagg aggcagaaag aaaaacatta   12180
cagatactca aatatattga taatcataac actttctgga agattaaaaa aatgctgaaa   12240
catgaatccc ttgctagaga aattacaaag ccaagaaaat agataggtct gaggattagg   12300
gagctgttca gttgctagga ggaacacaaa agcacagacc ccagactaca atgggtatga   12360
aaccctctgc acgccttttg ttgtccatcc cttgccaaag ctgttatgta aaaccctccg   12420
ggggaatgaa tgaaattatg tttatacagt tctttctata taagtgcaga agaatcatgt   12480
taaataaatc tacagggcag gattgttagt ttttctcctt ctcaagcaaa cttcagtgct   12540
gtcagataac ttctccatgt gttttttttt tctcttagaa tgagcccttc ctgagaaccc   12600
ctcggaatag taactacacg tacccccatca agccagccat tgaggtaacc cctgactcac   12660
atctgcctct ctcagacaca aaccatttcc acctgccagg ggctcgggtg tggtacaggt   12720
ttcagagtat tcactgaagc agaaatgtac ttcttacata ctggggattg gaatgtacag   12780
aaaaggctcc cggaccacga agccccagga ttgtcctaac atgttctcaa gttgcttacc   12840
tgacgtcagc ccccaagcag aggaagtgtc tatggatcga ttttctttga ccttggcaat   12900
cctgggctca cagacgtggt tactgcttag gcagctcagc ctctcaagag ggagaggcag   12960
ctggtgtgat gtggcgttga cttcttggaa ggtggaggct gagtgggagg gaactacaat   13020
tctggggatg ggacccaaaa ggaagtggag gcacgttgtt catgttcctg tgggccccta   13080
ggccttgttt ggttcaagtc aatcattcta gtgctgagga ttcagagccc atggttaatt   13140
ccattggatt aaccatgtct gtgagcctag gacggccact gcaaagacgg cctggaggac   13200
cccggactat accatgactg gcagtcaggc ctggtccgga tcaggtctgt tggtcaccag   13260
gatgggtttt gacccgcagt ttcagtttca cacctatatt atatccagtc tcatgttagg   13320
ggctagaagg catgcagaga agtatcgaac atggtccgga ccaagggaag tgagagccca   13380
gtagaatttc acaattattg agcacatact atgtgccaga cactattcca ggaagacaga   13440
aatgttaacc agacagatgg atcccggccc tcacgtagct tacaatctac tgagaaaggt   13500
gtcttatata catggctagg catggtcatt tcagatagtg atgacagctc tgaggagcgt   13560 gatgggctg gggcaaggga ggcaaattca ggtgcaccat gcaggccagg ccttcctgag   13620
gtgagattta aactgagaca tgcataatga ggagacactt gctatacagg agccaggaa   13680 cacagtccca ggcagaagga ccatggacca cacaggctca gaagtgggac tgtgttgggt   13740
gtatttgggg aagagaaaga aggtcagagt ggctggggc atgagaatga ggtggagagt   13800
gggggaaatg agatcaggag tgccaaggag ccagatcaca caaagcctga attactgagt   13860
aaaaccactg gatttcaagt ggagaaagat gggaaggcat tggcggtctc aggagagagt   13920
gacatgatct ggttcacgtc tttcaaagat ctccctgact gctatgtgta gaatgggttg   13980
gccatcagca ggagtgattg gggaaagaca ttttataagc cagctgaaga aactaaccca   14040
tatgaaatca ttaagaacta ttggatgcta agctctgggg tgcaagcaat accagattgc   14100
tggctgcggg ttatgctgtg tccagcctct ctgaattttc tcaggctcac gttagcccag   14160
tggaggcttg tcctcattga accagtgacc aaattccctg agaattgaaa cgtcagctgc   14220
atcttgtgaa tcaggcattt cttcatttat tcatttacct attggatgcc tatgtagagt   14280
gggcactgca ctaagtgctc ggtagacagt ggtgagccga atgggtctgg atctgccctc   14340
ttggttcttc agtctcatgc atctttgctt ttgctgctgg aagagctaaa aatcccagag   14400
```

```
ctagaagggc gtgtgtttgt tttaacagct ttctactcaa agtaaccaca gaaacaaaat  14460
tctgtcatct gaggtaacgt gaatgagcct agaggacatt acgttaagtg aaataagtca  14520
ggcacagaaa gacaaatact acatgttctc accatatgcg gaagcttaag aagttgactt  14580
cacagaagta gagtataaat agtggttatt agaggctggg aagggtggat ggtggttggg  14640
gagtagagat agcagaaatt gattaacaga aaattacagc tatataggaa ggagaatttc  14700
tagtgtttta tagcacagta gggtgactat agttaacagt ttaccatata ttttcaaata  14760
gctagaacag cagattttga atgttcccaa cacaaagaaa tggtaaatat ttgaagtgag  14820
ggataggcta attaccctga tttgatcact gcacattgta gagatgtatc aaaatatcac  14880
actatgcctc ataagtatgt acacttaata tgtcaattaa aaataataaa agcaaaacta  14940
ataaagtggc cacaaagagg ctttacctgg gagcttttta gaaatgcaga gtcctgggca  15000
ccaccccaaa cctgctgaat cagaatctgc agcttaagat cttcagggga tttggatgca  15060
ctgattttgg gtgtggtgca tggttcttcc cttgtgacgg atgagcacgt ttcaattcca  15120
accaggatct gttaatctac atggaatatg cttatctctg gttcaccaac tatctgagat  15180
atatctcatg tgctgatggc tgaataactt tttacgttgc attttctgtg agtatttgtc  15240
atctgcacac aagcatgctc ttgagttcat taaacccttta aacagaagaa atccatcaga  15300
atgatgaatt gagcaatccc ttgggaaaaa accaaattcc ataggattaa gcaaataata  15360
tttaaaagaa gttccatttt tgctctctca tgataggaat atttcaacaa gtcttatctt  15420
catcatctga ctgaacagat gagatgagtt ttcatagcat ctggcagtca gactcctgga  15480
cagtcaatct gctggtcaag ccctactcca tactcagtat gcatatattt gagactttgg  15540
gaagatactc aattttcccc cagatttctg gtactaatca tttctatgcc ctctgcttcc  15600
catcccactc ctttccccag cacctggaaa atatgttctg tattagagac aaagaaaatt  15660
gactaaaagc atccagggtt gcttacatca atttaaaaac atataaggaa taaggctgtt  15720
aagttaaata tgcaaaaaga catacaggta tccagaaaag acaggcagaa accaggagct  15780
ttacaatttt aaaatatttt gtgttattat tctaaaaata ttttaattat tgtctaggtt  15840
ctaccattat aattagtgtc agttagctta atttataaa acacacatac ctgtaatctc  15900
atgttaggca tccaaatgct gtgttccttt gggagaccca cctgtgtagg acttcatggt  15960
tttcttccct gctttggggc agccactggc tccattcaaa gcatagatat atgggataa  16020 gaaaggttgt gtgtgggtgc acatgtggag acatgcacta tgggttgtgc ataggggtag  16080
ctagacacac ccatttctcc ccctttaatt tccctcctag cccacctata actcacagtt  16140
ctttccctca catgatcctg tatggtgact catttctagc ctccatcaaa aatcccttag  16200
ctggttcttc ttgggctgaa gcttatctcc ctgcacaatg agtgttgggc actgaatctt  16260
ttctcctgtt gatttagaac tggggcagtg acttcctgtg tacagagtgg aaggcttcca  16320
atagtgttcc aacctctggt gagtgaaaac atcatcatct ccttcaatta agggccttgc  16380
cgaatatcag gttgtgggga gaccctgcaa acatacctg gagctttaag caggacttgc  16440
taattcccct gcagtgcaga cctagatcct gcggcctgcc gccacagctg ggcttccatg  16500
tggaggtgca cagagctctc cattggatgc tacttcttgt ctccttatag tcccagtggc  16560
agtcccttag gcctccctgc ccagtgaggc aggtagagtc agggattggg atctacctgc  16620
ctgtgctaca tgaccctgca gctggaactt tcctggacca ccccaatgtc aatcaggctc  16680
ttctgagggt ggatgatagc catgaaaccc attccctgca gtgccttggt tggtctgaat  16740
```

```
gaatgggagg ggcaaaactg ctaaagcctt aagctgaaaa taagtacaat ggggagcagt    16800
gggacagagt tatagacttc tggtaaaatg tgtactttaa gaggtagata cccccagccc    16860
ccacaaccac ctctctgctt gtctccccta gtccaccagc tccgaccagc agacatcaaa    16920
gtggtggccg ccctgggtga ctctctgact gtgagtagtg agccatgaac caggatgggc    16980
agctcagagt ccagccaggc cctgcgcaga atctgtgctt ccccagcatt ggctccgctt    17040
tcagtgctga gcccgtgtta ctgagggcct acccatgtca ggcactgaaa cacagccagg    17100
agatgtagaa tgccctgtct cgccaccttc ccagttctgc tcaaagcccc ctcgtccatg    17160
aggcctcccc tcaattcccc agggagaagc aatccccgcc ttccccactg ttcacaggcg    17220
ttttgttggt gtgtgatggc actcattcaa gtctgcctgc cttcatcagg ggactcatct    17280
ccatctaccc agactcagag tggcaggtct tacacacaca ctgccccatg ctccctactc    17340
catttaagga catgtgcttt ggggcagagg gagcccggtt cctcacacat agcacagtct    17400
tgctaagtga attgtgttcg ccaattactt agccattgtt gtgtacacca acactctatt    17460
agcaattcta agggaaatga ggtatgaaac acagtcatag ccccccagca acctgtctgg    17520
ctggaaaaac aagaaacgta cacagaaaga aatgcatagt cacatagatg acatatagga    17580
cttggatgtt ttatttttat tttttaactt ctaagttcag gggtacatgt gcaggtttgt    17640
tacacaggta aacttgtggc atggnnnnnn nnnnnnnnnn nnnnnnnnnn nnnnnnnnnn    17700
nnnnnnnnnn nnnnnnnnnn nnnnnnnnnn nnnnnnnnnn nnnnnnnnnn nnnnnnnnnn    17760
nnnnnnnnnn nnnnnnnnnn nnnnnnnnnn nnnnnnnnnn nnnnnnnnnn nnnnnnnnnn    17820
nnnnnnnnnn nnnnnnnnnn nnnnnnnnnn nnnnnnnnnn nnnnnnnnnn nnnnnnnnnn    17880
nnnnnnnnnn nnnnnnnnnn nnnnnnnnnn nnnnnnnnnn nnnnnnnnnn nnnnnnnnnn    17940
nnnnnnnnnn nnnnnnnnnn nnnnnnnnnn nnnnnnnnnn nnnnnnnnnn nnnnnnnnnn    18000
nnnnnnnnnn nnnnnnnnnn nnnnnnnnnn nnnnnnnnnn nnnnnnnnnn nnnnnnnnnn    18060
nnnnnnnnnn nnnnnnnnnn nnnnnnnnnn nnnnnnnnnn nnnnnnnnnn nnnnnnnnnn    18120
nnnnnnnnnn nnnnnnnnnn nnnnnnnnnn nnnnnnnnnn nnnnnnnnnn nnnnnnnnnn    18180
nnnnnnnnnn nnnnnnnnnn nnnnnnnnnn nnnnnnnnnn nnnnnnnnnn nnnnnnnnnn    18240
nnnnnnnnnn nnnnnnnnnn nnnnnnnnnn nnnnnnnnnn nnnnnnnnnn nnnnnnnnnn    18300
nnnnnnnnnn nnnnnnnnnn nnnnnnnnnn nnnnnnnnnn nnnnnnnnnn nnnnnnnnnn    18360
nnnnnnnnnn nnnnnnnnnn nnnnnnnnnn nnnnnnnnnn nnnnnnnnnn nnnnnnnnnn    18420
nnnnnnnnnn nnnnnnnnnn nnnnnnnnnn nnnnnnnnnn nnnnnnnnnn nnnnnnnnnn    18480
nnnnnnnnnn nnnnnnnnnn nnnnnnnnnn nnnnnnnnnn nnnnnnnnnn nnnnnnnnnn    18540
nnnnnnnnnn nnnnnnnnnn nnnnnnnnnn nnnnnnnnnn nnnnnnnnnn nnnnnnnnnn    18600
nnnnnnnnnn nnnnnnnnnn nnnnnnnnnn nnnnnnnnnn nnnnnnnnnn nnnnnnnnnn    18660
nnnnnnnnnn nnnnnnnnnn nnnnnnnnnn nnnnnnnnnn nnnnnnnnnn nnnnnnnnnn    18720
nnnnnnnnnn nnnnnnnnnn nnnnnnnnnn nnnnnnnnnn nnnnnnnnnn nnnnnnnnnn    18780
nnnnnnnnnn nnnnnnnnnn nnnnnnnnnn nnnnnnnnct ccaagtttaa tatggcctgg    18840
agaaaagccg gtactatttt tagaaaaggc aaatccaggt cctagctgct accccagggc    18900
cagaggaagg ctcttccagt gccctcagcc tatacccag ccctgaactt tctttttgct    18960
ttttacagac agcagtggga gctcgaccaa acaactccag tgacctaccc acatcttgga    19020
ggggactctc ttggaggtga ggatgttctt gatgcatgct ctattgatga tgctctctca    19080
gagaggtgtg agtagtgtgt ttcctgtcac ccctccaggg atgcagttgg gtccccaggt    19140
```

```
cccagcgctg agacaggaga ctcaatgctt gcattacccc tgagggtgat gggagagacg    19200
ccccaggggc ccagaacccg gttccggttc tggcttgtgc atatgttgac acagggagca    19260
gcatgttggt gtgagtttaa caaatatgct ttctcctccc cagcattgga ggggatggga    19320
acttggagac tcacaccaca ctgcccagta agtagcagcc cagagaggca ccatcactgt    19380
ggccgtcctc cctggggcca gggccttcct gctggaggag gggaagagga ggttatctgc    19440
aagaagggaa gtcagccagc cctgaaaagc cccagacttc ctgtgtccca cccatgtccc    19500
caccctgcat gctcatctca gttactgtga gggtcctgca ggctctcacc tgtgctcttc    19560
tcctcctcct cctcctctaa agacattctg aagaagttca acccttacct ccttggcttc    19620
tctaccagca cctgggaggg gacagcagga ctaaatgtgg cagcggaagg ggccagagct    19680
aggtgagtag atgccgtaca ggagggcgag nnnnnnnnnn nnnnnnnnnn nnnnnnnnnn    19740
nnnnnnnnnn nnnnnnnnnn nnnnnnnnnn nnnnnnnnnn nnnnnnnnnn nnnnnnnnnn    19800
nnnnnnnnnn nnnnnnnnnn nnnnnnnnnn nnnnnnnnnn nnnnnnnnnn nnnnnnnnnn    19860
nnnnnnnnnn nnnnnnnnnn nnnnnnnnnn nnnnnnnnnn nnnnnnnnnn nnnnnnnnnn    19920
nnnnnnnnnn nnnnnnnnnn nnnnnnnnnn nnnnnnnnnn nnnnnnnnnn nnnnnnnnnn    19980
nnnnnnnnnn nnnnnnnnnn nnnnnnnnnn nnnnnnnnnn nnnnnnnnnn nnnnnnnnnn    20040
nnnnnnnnnn nnnnnnnnnn nnnnnnnnnn nnnnnnnnnn nnnnnnnnnn nnnnnnnnnn    20100
nnnnnnnnnn nnnnnnnnnn nnnnnnnnnn nnnnnnnnnn nnnnnnnnnn nnnnnnnnnn    20160
nnnnnnnnnn nnnnnnnnnn nnnnnnnnnn nnnnnnnnnn nnnnnnnnnn nnnnnnnnnn    20220
nnnnnnnnnn nnnnnnnnnn nnnnnnnnnn nnnnnnnnnn nnnnnnnnnn nnnnnnnnnn    20280
nnnnnnnnnn nnnnnnnnnn nnnnnnnnnn nnnnnnnnnn nnnnnnnnnn nnnnnnnnnn    20340
nnnnnnnnnn nnnnnnnnnn nnnnnnnnnn nnnnnnnnnn nnnnnnnnnn nnnnnnnnnn    20400
nnnnnnnnnn nnnnnnnnnn nnnnnnnnnn nnnnnnnnnn nnnnnnnnnn nnnnnnnnnn    20460
nnnnnnnnnn nnnnnnnnnn nnnnnnnnnn nnnnnnnnnn nnnnnnnnnn nnnnnnnnnn    20520
nnnnnnnnnn nnnnnnnnnn nnnnnnnnnn nnnnnnnnnn nnnnnnnnnn nnnnnnnnnn    20580
nnnnnnnnnn nnnnnnnnnn nnnnnnnnnn nnnnnnnnnn nnnnnnnnnn nnnnnnnnnn    20640
nnnnnnnnnn nnnnnnnnnn nnnnnnnnnn nnnnnnnnnn nnnnnnnnnn nnnnnnnnnn    20700
nnnnnnnnnn nnnnnnnnnn nnnnnnnnnn nnnnnnnnnn nnnnnnnnnn nnnnnnnnnn    20760
nnnnnnnnnn nnnnnnnnnn nnnnnnnnnn nnnnnnnnnn nnnnnnnnnn nnnnnnnnnn    20820
nnnnnnnnnn nnnnnnnnnn nnnnnnnnnn nnnnnnnnnn nnnnnnnnnn nnnnnnnnnn    20880
nnnnnnnnnn nnnnnnnnnn nnnnnnnnnn nnnnnnnnnn nnnnnnnnnn nnnnnnnnnn    20940
nnnnnnnnnn nnnnnnnnnn nnnaaaatca aaaattagct gggtgtgatg gtacacgcct    21000
gtaatcccag ctactcggga ggctgaggca ggagaatcac ttgaacccag gaagtggagg    21060
ctgcagtgag ccaagatcgt gccattgcac tccagcccgg ataacaagaa tgaatctcca    21120
tctccaaaaa taataataat taaaaataaa taaaagatac aaaggaatca aaagatgaac    21180
tccctggcca cgaagagctt gcactctagg taaggaggct aaacaaatgg gaaataactt    21240
tctgaaaaag acaatgctgg gtatggcaac aatgcagtgc ttcgcatgga gtacaattaa    21300
gagaacagaa gagcacacag tatgaactgc actgtctaaa gacagatgca gacccagaag    21360
ggaccccctga aatcatccag tccaacctct tcctttaaaa gatgggaaaa gtcaatccta    21420
gcaagattca gcaacttgta caagctcaac agcaagttgg tagcagagct gaaagtagaa    21480
```

```
ccactggtcc ctggggtaaa aaaggaaatg caagatgtgt ggatcaggga gcccagagag    21540
gaggctcaag ggaaagtagg acttggtctg ggcctgaagg atgggaagaa gatggctagg    21600 aagagggaa gaagcggcat ttgtaacttc ccctcctacc cacgagggct tattgcccat     21660
ggattctctt agtcacacct tgaacctgtt aaaaggttaa aggcacttct gtggtcacct    21720
ttgaccagaa aagtctttct ttatagcttt ctggtatact catcaatagc aataatgtat    21780
gggatacaat cctagatctg taaattctcc ttaatgagaa acaagggtag ggatggtacc    21840
atgtgtgttt ggccacgtac ctagcttacc gtggccaccc aaagattttc agtggccagc    21900
tcgcactggt tgctgctttt atggcttctt ccatggacgc tttcattggc tatatcccct    21960
ttgctgacct aacttctcac agacatttct ttaaacacag ctttattgag gtataaatga    22020
catgcaataa acgtcacatg ttaaaaggat ataatttggc tgggtgcggt ggctcacgcc    22080
tctaatccca gcactttggg aggccaaggt aggcagattg cccaggagtt ggagaccagt    22140
ctgagcaact tggtgaaacc ctgtctctac caaaaataca aaaaattagc cgggcatggt    22200
ggcatggacc tgtagtccca gctactcgga aggctgagat gggaggatca cttgagctca    22260
gaggggttga ggctgcagtg agccgtgatc acaccactac actccagcct gggcaacaga    22320
gcaagaccct gtctcaaaaa ggatacaatt taacattgta cctgtgaaat catcaccaca    22380
atcaagatga aaaatgtgtt tatcacccac aggagttttc tcaggcccct tggtaatctc    22440
tccctcctgc tccttcctgt ccctacctca caccccaggc aaccactaac cttctttcca    22500
tcacaataga ttagtttgca tttttaaaaa ttttatataa atgggatcaa agagtatata    22560 cttttttatct gacttattta gcaaaatgat tttgcgatgc atccatgtta ttcggtatac    22620
caatagttcg tcccttttta tggctgagtg tagtgttccg ttggcattca tatcgctcat    22680
ccagaacacc aaatggtatt gttttattta tggcagacat caggggatga agggagaact    22740
aatcctgtcc atcctggttt attggagagg gagaaaaaaa aaagtgagga gatggggaat    22800
ggtgcggaaa tctaagtaac cacagaaaag aaaaacaaaa ggattaaagg agcagagagc    22860
agggcttaga agtaaaggtt aaaggagtca ttaagcctgg aaaggagaaa actgagggat    22920
aattgtgagc tgtgactttt ctcaaatata caaaaggtta tttttaaaac aggcaactga    22980
agaagaaatg aacaggcttg gcttacgaag aaagagcttg aggaagtata agggaaagtc    23040
cctgagggga ggcttgacgg gatcccaacc cgagtggccg atgagactat tgggtggcag    23100
gggctagatc aatgtggctc cagggtccag ggcagccatg tgattgttac taagctgaga    23160
tttcttgaga atggaatgac ctttgtactg gtaacatcat tcttcttgaa acacctctct    23220
tcctaggcca aaatcccatg tcgtgagtcc tcgctcctga gccggcacta acgcccctct    23280 ctctacccccc cacctaggga catgccagcc caggcctggg acctggtaga gcgaatgaaa    23340
aacagccccg tgagtacagg ccccccaggcc acccctgaaa ggtgcccatc tcctgctggc    23400
tggggagggg acagccccat aagggtccct ctcaccacag cacttcctgc tttgggctag    23460
ccaaaagatc ctcggagaag cagtccttac caaggaggcg cctgccctgg ccacactcct    23520
agacgcaggc tgtggcaccc ctcacccccag ggccggctgc gggagggcaa ggtggaacag    23580
ggagttggct gaggtggtgg ccttggcctc tgacagcttc ctgctttaac caagaggtgg    23640
cttcccagag ccctattatg taaatgcaag gttctaaaaa taggcttctc attccaatcc    23700
agttctgcct ccttcccctc accctgcccc tctgaaactt ctcactagca ctttttttt    23760 taaccgttca gtgtttatgc ctaggaattc agctcccggt gggattccta ttatggaggt    23820
ggccaagtgg aaagccaact gcttagaggg cctcccagcc ccaaccccgc ttctcagtcc    23880
```

```
acgctgggct cttcctccag tctccttccc ccgaccctaa gaactcatcc caggggcagc   23940
ttagggcctt tgcttctagc tgcatccttt gcctacagct ccctggaagg ccttcatttg   24000
gggggacgtg gtaatcccct cggcatttaa tgggccaagg atatgtggga cacatccaca   24060
ttctacttct ccagggacac aactttctta agatttcaag gggaaaatag ccctcccttg   24120
tgtaagcaga accccgtccc ccgccagcgc ccaccgccaa aaaaaaaaaa catcctctct   24180
gtggagcacc ttatcctagc accaattgag ggctgggaag ccccactttg ttgcttttct   24240
tttttttttt tttttagacg gagtctcgct ctgtcaccca ggctggagtg cagtggtgcg   24300
atctcagctc actgcagcat ctgcctcctg ggttcaagtg attctcctgc ctcagcctcc   24360
caagtagctg ggattacagg cacctgccac caggccaggc taattttttgt attttttagtg   24420
gagacggggt ttcatcatgt tggccaggct ggtctcgaac tcctgacctc aggtgatcca   24480
cctgcctcag cctcccaaag tgctgggatt acaggtgtga ccaccgtgc ctggcccaat   24540
ttgctgcttt tctctgttac agtataaata agacaaaagg cacttggagg gcgggcgggc   24600
tggcccagta gcaacatttg tatgtgcctc ccaccaaggc ctaaactcag gatcttctgt   24660
cccctcagga catcaacctg gagaaagact ggaagctggt cacactcttc attggggtca   24720
acgacttgtg tcattactgt gagaatccgg taggcccccg accaaccca tggggacctg   24780
agaaggaagg tgctgacctc tggcaacacc cttgcccatc catccctggc cctgccccga   24840
gctcctcgct catgggaacc acatttgcct gctgccccag gccctccctg gtttacacat   24900
gccaggcaag gcccagcctt ttctactgcc tgagcgaccc ctggaagagc aggtgcattg   24960
gttccccaat tccagaagta aggccaaggt ggacccactg taggcactgc tgaggtgagg   25020
cctctcttat ccacacaaat atgacctctg gtaccagata ggggactagc catcctcacc   25080
ccatccctgc cctgtttcat tttgaggaag ggcaaaacaa tgttctaaat ggggttggat   25140
gggtcatcac gagttaacca aacctcagtg gtggccctgg gagcccaaac ctgttcctga   25200
tgtttccatg gggaaatatg tccagactca caaacttctg gaagttgtaa cttccaaaag   25260
tttttatttt ggaatacatc ttgttctaag ttggggacat tctgtatttt atttggccgg   25320
gaaaaggcag ctgcccagcc tcagagattg tggtcgaatg tttgacagtc acagatggtg   25380
gtgtggggga aaaggcattt atcactcctt gtggctcaca gaggcaaact accagaggct   25440
tgatgagaag tatcctccca cacacaggag ttggttttcc aaacctcttc ccctcagttc   25500
tctccctgac cacccacact ctagaggcag aagtgaccct aactcatggg gatttaagta   25560
ttgctgtgtt ctggactccg gggatacctg gaccccagag ctgcgtggac actgtggacg   25620
ctggcgtagg gaaatgccct ctactagtcc caggatgtgt gttcttcatg gaacagtca   25680
ggtttatact tccgagagcg tagtttagtt gaaagggctg ggctgccccg actaggatta   25740
actcagactt ttttaaaaag aaggaaaggg ggaaaggcag aaactctggg agacacgagg   25800
tcccctctcc tctattttaa ctcttcggca tggattgtct atcttgttcc tttcccttc    25860
ttcccaactc ccagtacccc ttctggtggc tgtggccaga aactcagcga acagcacttg   25920
tcctatgccc atcagtgtgc tggaattgag tgcacggtat ctcacctggc ctcagctctt   25980
cgtctccaga aaaataatg ggctgcctga gctctcccct cctgcctgag tggtgctgct    26040
ttgtgggtgc ctcaactccc acttcctgtg gacatgcttt cttccatgag tataagagct   26100
tcaggttacc acccgcaccc ccactggtat cagcctgtga caccttctgg gcctgtagcc   26160
cagagccaca tctaaaaata gaggcccatc tccctctgct ataaagcaaa gccctgagat   26220
```

-continued

```
tcagcctgca aggacttact gagcacctac tatgtacctt gtttgcatca cccaggatgc    26280
tgtggacaca cctctaaatc agcctcctac tggggagatg gttcagagga agagaacctt    26340
acactgagtc acaggggata gaagttaggg gaacacagga gagcaaaaca tttcaggcag    26400
tgggaccagc atggaccaaa gcccaaagga aaaaggaagt gtggccaccc agggcatggc    26460
aaggggctgg agaaggctga ggtcagatga cggatgggac tgccaagagc caaggccaaa    26520
aagtggcagg acccagcact ggcagagtcc actgttgggt ctgagattat gtagagcagg    26580 gtggggttg ggattgttca tggtgtctag tagggacaa gggatgattc cttacagaga      26640
ctcagcagca acaagaactg ggcttctcag tttgaccagg accaccgaag cccctctgta    26700
cccactcagt catttagccc aggccccaga gccctcctat gctcttgcca ttctctcaga    26760 gcggcacca ggggctaaag agagtacccct ttttttccta caggaggccc acttggccac    26820
ggaatatgtt cagcacatcc aacaggccct ggacatcctc tctgaggagg taggagaggg    26880
gttacgtgtt cctgggtccc gccagccacc tccctgggat gcatgtaggc aggctgtgtt    26940
cagtgagatg ctcacggagc agagacccgc catgagtgag cacctggatg gcaggagggg    27000
aggtggctgt caagctcctc tgcagggaaa attctcactt ggccagagac agggttgtgt    27060
ggtagcaatg agcttgcctc tgaaccaatt ggcccaggtt tgcgcccagc actgtggctt    27120
cgggcaagtc acttccctgt gtctcagttt ctcaacctat aaagcggggc cactcaagaa    27180
gattcagtga gatactacaa gttgcatccc ctctctgggc ctcagtttct tcattggtaa    27240
aattgagggg agtgggaatt ggattgtaga tgacccccag gttcctccca gcagtagcca    27300
gtgccctaac gaaaccaccc tccactccct gcagctccca agggctttcg tcaacgtggt    27360
ggaggtcatg gagctggcta gcctgtacca gggccaaggc gggaaatgtg ccatgctggc    27420
agctcagtaa gtggacaggt caccgtccca aggcaagggc acctggggtg aggagggctt    27480
gcaggtgcca aaggaggaga ccagttgagg cagagccagg caggcctgcc agagggtaga    27540
catggctcag gggcttggac aacatcagga agtacctcta catttgcaaa tgcctactgt    27600
atgcaaggtg cctcatttct ctggaccccc ttttgctttt ctgtgaaagg agacagacca    27660
aatgatcctt aaggctccct gacattgtca gtgattgcca aggcaaacct tggcacgctg    27720
ctccctgttg agaagcagca tggggccatg agctttcaag gctgctacat ccagccttga    27780
ctgttctgcc atttaggagc tatgggacct tgaacaaacc acataacctc tatgagcctc    27840
tgtgttcctc atctgtaaag tgggggtgat gacaccttcc ctgcaaggta gatgtgaggt    27900
caagaggaaa caaggtacct ggcctaccaa gactaccaag agcagggtct taggaaatag    27960
ctcttattcc atccttgatg gggcctgtcc ttgatagctg ggcttggagg caaggtgcta    28020
atgggcaaga caagaactcc tatcgggggc tggaagtcat taaagctctt gaaccctggt    28080
aggaagttgc catgttctga gggcacaggg cctcccacag tttgagtgat tattgctatg    28140
agagaggagg ttctccaggg agctgaggag tcctacacct gggctcaaat ggatttgctg    28200
caaaggtgac cagctggttc ccattcttgc agggaaccct gctctctcgc agggaacggc    28260
tcctccagag tctgtctgta tcgtgttcca tgttgtcagg gttgcttcca gccggttggc    28320
cctccccagc tttcccacag acttcccaca ctggagccct gagggagggt cctaagcagt    28380
tgcaggaaga gctgagaggc ccccggaact tgaggagcga ttccaaaccc agggacagag    28440
ccatcgtggc tggtttccta aactccagtc tcctgtctac ccagtcctgc tctggagaaa    28500
tcccagggac cacaggcttg ggaaggagga agggaatag gcgttctgtc cacagggagg    28560
tccaggcaac agctttccct cttttctctat gaacaatcat cctctggacc tcagggctcc    28620
```

-continued

```
tgagttagca ttctgtaacc tgggtccaag aatcagccaa aggtgtattg tggggatact   28680
tgtgtgtcac cccccgccct aggtaaggca gcacaggctg caggcccctg ggtagtggc   28740
ctgctctgtg tgtcagagcc agcctcccag gaggacagag ccacagtgcc ccaggcagcc   28800
tcaatacaac actccctgtc tcacaggaac aactgcactt gcctcagaca ctcgcaaagc   28860
tccctggaga agcaagaact gaagaaagtg aactggaacc tccaggtaag ccctgcagcc   28920
cttctcttac tgacccagct gggggccccc ctgtactcca aggactggga aatcgaatgc   28980
ccagcaggat gtggccaaga gcaagccact ccctaaaagc agattgcagc ccctgaaata   29040
cttaccctg caaattgaac accaaggcca gggaagggag tgagagaccc caaagtggaa   29100
gctgagaaaa tccccttctc ccagcgggta ggcagcaaga gattcccaga gtagactcct   29160
tgtggtaggg cccattcccc acccagagcc atgtgtaata attactactc acttcctccc   29220
ctcccttcat taaaaacaaa aggcttaggc ccgacacaat ggctcacgtc tggtgtccca   29280
gctactcagg aggctgagat gggaggacag cttgagccca ggagttggag gctgctgtta   29340
gctatgatga tgccattgta ctctgcctag acaacagcgt gagaccctat ctcaaaaaaa   29400
aaaaaagaa aaaagaaaa aggcttagcc ctgccctact taactctacc tcaaattctc   29460
cttgccctct ctctgcccc ttccatctcc ccacctccac tcctgcttat gtctctgcct   29520
ctattgttcc ctctcaggct caggtagcat ttccattctg caaactgacc ctccttcatt   29580
cacaaggcaa gtctgcttcc ctcctctaag gagcttcccc tgcctgaact tcacccgcgg   29640
acatctcccc atatcacatt cagtctgtac ttgatgggcc ctaaaagccc caagggttc   29700
tcatgttttc acatcttggc tcattttcc agatggatga taaactcctt gaagataagt   29760
acatctagtc tgttcctttt acattccatg cttgggtact taaatccagc caccgtggac   29820
tctcctcccg caaagttcat gggcattttg ggagctggtg ttgagatgct ccccatctga   29880
cctgcagccc catgttctaa ttgacctctt cgtgcagtga gaggagggga ggactttggc   29940
ctatgcaatc tggtcagtgg ctcagaccca gcctttcagg cagaggcttt ggaatgggac   30000
tgggtggagc tgtgtagcta gggagcttct cccaccagga gccgctgggt tcaactcatc   30060
tctgatcctg agaaccagca tagggctttg aaatgtccgt gcccatgaat gggtggagaa   30120
taaaagtatg tttgcatccc actagagtag ccccttaaag tcactgtcct ttagggtgag   30180
ttgactcccg tcaacaacca atccaaggca gcaggactgg accctgtctg tgcagccttg   30240
ccaggagggt tgagcagctt ctctctctgt ccccagcatg gcatctccag tttctcctac   30300
tggcaccaat acacacagcg tgaggacttt gcggttgtgg tgcagccttt cttccaaaac   30360
acactcaccc cactgaacga ggtgagctgc aggtatttta gggaggctca cgtatggggg   30420
ccttatcaca gacgatggat gtatttcctt ctctaagtgg gctttttttt ttttttaacc   30480
atctctctcc aagaggattc ctgagggtgg cttttttccac attacctcct ttttgtgggg   30540
gctgggctgt gattggaact cagatgtact ttgaaaggaa atcaatagtg actaagctcc   30600
caggcctggc cctgatgttt tctggattgg gatagaatgg aaagcttcct aaaaatgtta   30660
ctcttttcaa ctcttaggat aggggtgctg aaagaaaagg gagagactat gggtgggtcc   30720
aattcttgtc tgtttaaaaa gaaaattccg gccgggtgca gtggctcatg cctgtaatct   30780
cagcctttgg gaagccaagg cggttgaatc acgaggttag gagtttgaga ccagcctggc   30840
caacatggtg aaaccccgtt tctactaaaa atacaaaaag ttagctgggc gtggtggcag   30900
gcacctgtaa tcccaggtac tcgggaggca gaagttgcag tgagctgaga ttatgccact   30960
```

-continued

```
gcactccagc ctggctgaca gtgcgaaact ccgtctcaaa aaaaagaaa aagaaaaaa    31020 agaaattcta aattctggga gttttccat cagtatctga gcaagttggc aggaaagttg    31080
aaagaatgaa aggagacatg cccagggcac ctgctgggag agtgagtggg gctcaggtag    31140
cagagccctt tcccaggatg ataacctcct tgccgttggt tgcagagagg ggacactgac    31200
ctcaccttct tctccgagga ctgttttcac ttctcagacc gcgggcatgc cgagatggcc    31260
atcgcactct ggaacaacat ggtgagcagc caagggcctg gtgggccttg tcaaggggg    31320 atctaaggat attgacactc tgtctcacaa tggcaaaact actggagaca tggctccttt    31380
ctccccaaag cccaaagtgg cagcacacct tattggtcct gatagattaa ttccaaaggg    31440 aaaatacccct atattttatcc aacacccttt gaaagttata caaacacaca ctcacacaac    31500
tttattcttt gttccttcag caatgcccag gtactgcgag gggatccctt tgtaatcaga    31560
taggttggct agatgaaaat accaacttct acctcgtact gtgtgacctt gggcaaacga    31620
tctctctggc cacctgtatc aacatctata aacagtgaa acaagacag gtctcagaca    31680 acgcattgag atcatgtgta catggcacct agcacaatag ttagcactca gcaaatgtca    31740
ccaccatcag ccttccaagc actccgggct caactcatac ccaactcatt tctctaaaca    31800
tcgaaaagtg gagatccaca cagcctgttt tccgaggctg atacctattc cagtcctttc    31860
tgatgggaag aagggacctt atgaaatgaa catacagtct gggggtcttt cagggacacc    31920
tgcctggtgc ttccactctg ccttctgtgg ctggccacca gcaactgaac ggtttccgca    31980
cagcacttga cctgtcaccc caacaactg gatcctcttg cacggagcaa atgaaatgcc    32040
ttcccaaccc aatggtttct tttaatccag gctcagtggg taacacaatc cccacccaa    32100 cctgtatgtt ccctccttg tcctatgaca actaaacaag ctacattcca gctcctttta    32160
tcacagtttc aggcccgtag tgtctctgcc aaccaccgct gtgcaaacgt tcccaccct    32220 gtcagctcat ccagtatgtc cagcatccca ctcggctgac tcacaatatt gactttctcc    32280
ttagctatac catctcctcc tctctagcaa cctcttcttt taagaacagc atgtaaactg    32340
gctttatcct tggcctagtt aatggcagac tcagcttatg tcgacttcca ttgtcagggg    32400
gttttcctcc tgtggacatc acgtacctgc ccactccaag aacttctatt gtactctttc    32460
agcccaagac tccggattgt aaccaaaatg tctttgagtt tgccccacga tttttaaatc    32520
agtttatatg gtataattcc tgtttctttt gtggattttg ttttgaaggc ggttgtcctt    32580
cactggctga atcatgtgac tttattcctt tgtaaaaatc ttcccaaaga aagggtacct    32640
attccctgtt cctttcccc tgagacctca ggggattcca cagatgccct tggcccttcc    32700
ttccagtttt tttcatcaag gtatggcctt cctaccaggt ggcactccaa gtctgcttaa    32760
atctgggacc ctccaggaat ctcctggggc tggatagcca tagtgacggc tggaacatga    32820
aaaagagtcc attggtttct tttcttgtga attaacaatg tagctctggc caggcacggt    32880
ggctcatgcc tgtaatccca gcactttggg aggccgaggc aggtggatcg cttgagccca    32940
ggaattagac accaacctgg gcaacacagg ggagattctg tctctacaaa aataatcaaa    33000
atattagcca ggtgtggtgg tgcatgcctg tagtcccagc tgctcagaag gctgacgtga    33060
gaagatcact tgagcatggg aggtcaaggc tgcaatgagc cgagatggca ccacgcact    33120 ccagcctggg caatagagtg agaccctata tctcaaaaaa caaatagaaa aaaaaatat    33180 atgtagctct ggccttctct tctaaagcag ttcagtagct cttcccattc acccaggtaa    33240
gaggccttta tttcataaag ataagtggga ggagtttaga tatgaaaaca aaacgtaaac    33300
accgcactgg agctattgtg gaaacaaaac aagactgtcc atggttcccc agccattatt    33360
```

```
atctcagcca tacccccgaat ttcaaaataa caaaaacaaa actaaagcca tccaggggtt    33420
tcttatccta ggctctataa tttgggtaaa taattataca gtctaatgtt ttcatccaaa    33480
gccaatctta gacataaagc tgtagcatga tgccaacttt tcagatcggc ttctggctgg    33540
aatttcaccc ctagagtaac aaaaaataaa taatagacca ttagagctgg aacagactga    33600
gaggtcatct agccagaaca ttctgtaact aaagcataga aacatgaagc agtttgccca    33660
acataacaca gactgttcat ggcacaaggg ggattacaga ccaggttttt ctagtccttt    33720
cctggtgacc tgggcatgcc accacccctcc ccactgctcc caacctgata agcacatata    33780
tacccggtga attcatgtct cacaattaga gtcctatgac atagtgtctg caggctttgg    33840
ctgatgttcc catagtgtct gcaggctttg gctgatgttc ccagggttcc ctactaggaa    33900
gcaaaaagca ccttaaacta tttcatctta tttcatctcc tgcccctcct ctcacgtcct    33960
tctcgagact tttgcaaagg caaagccaga agctccagca gcaccagggg atattttcct    34020
cttcctctgc cttcttctgt cttcttatct gaagaagttt ctctttcccg aggcctagtc    34080
ctctactgct gcctctactc cctcttctgc agaaatcctg ctctcagcca gtgtttgtat    34140
ctccccaggt gctgggtgac agctccagcc tcctaactga catccctgtc ttcagactta    34200
gagctcttag aatcgtgact ctcagctctg gctgcatatt agaatcattc agggacattg    34260
tgtatgtgtg tatgtatgtg tatatatgta tgaatgtgtg tgtatgtgtg tgtgtgtatg    34320
tatgtatgtg tatgtgtgta tgtatgtatg tatgtatgac agagtctcac tctgttgccc    34380
aggttggaga gcaatggcac catctcagtt cactgcaacc tccgtctcct ggattcaagc    34440
gattctcctg cctcagtctc ccaagtagct gggttatag gtgcatgcca ccatgaccag    34500 ctaattttg tatttttagt agagacaagg tttcgccatg ttggccaggc caggctggtc    34560
tttaactcct gacctcagga gatccaccca cctcggcctc ccaaagtgct gggattatag    34620
gtgtgagcca caatgcttgg ccatccaggg acttttaaaa caattagtgc ctacagccac    34680
tttggaaaat tctttggtat atttaataat gctgaacaca tgtatttcct gtgatccaag    34740
gatttcactc ctaggtatat cccccaaaaga aaggtatata tgtgtctacc aaaagataca    34800
cacaaaaata ttcacagcag cactatttat aaatagcccc aaactagaaa ctccccaaat    34860
gtccactgac agtaggatgg gtgagtaaac tgtggcacat tcatactaag gaataccata    34920
caggtctgac cgcatctgtg gctttaaaca aaaatcaagc agggtgatgt gacacagagt    34980
aatggctggg aagagggagg cctcactgaa gaagtgacag ctgaacaaac ttcaacaaca    35040
tacaataata tctataaagt tcaaaagcaa gcagcttggc atatggggtt agacgtcagc    35100
atgatggtgt agagactcac tgggggatga atagtcctgg aagaaggtgg aaaggggctt    35160
ttgaggacta taatagtctg ttgcctgact ggatgctggt atgttcattt tatcgaaact    35220
tatctgttgc tcacttatga tttgtactcg tttctatgtg tatgttagct tcaattaaaa    35280
gtttacttga ggccgggtac agtggctcac acctgtaatc ccagcacttt gggaggccga    35340
ggcaggcaga tccctgagg tcaggagttc aataccagcc tagccaacat gatgaaaccc    35400
catctctact aaaaatacaa aattagccaa gcgtggtggc acgtgcctat aattccagct    35460
acttgggagg ctgagacagg aaaatcgctt gaaaccagga ggcagggtt gcagtgagcc    35520 aagattgcat cattgcactc cagcctgggt gacaagagta aaactctgtc tcaaatttaa    35580
aaaaaaaaaa aaaaaaagt ttacttgaaa aacaatatca gtgcctgacc gggcttatcc    35640
ccagagagtc tgacttaatt ggtctggagt gcgagctgga ttcggtactt tgtgaaagct    35700
```

```
cctgagatta ttttaatgtg cagggtttat gaaccgctgc cttagatctg gtccccacag    35760
agaaatcaag taatctgtat aaaagaaaac ctgacccagt cactcccctg ctttcaaact    35820
tccaaagcct cccacctctg aaggaggcag gccaggcccc atagcacagc acactaggcc    35880
tctgggactt ggcctggttc acctgattaa cctctctggc taccatttcc accagcgtct    35940
gcctcgcatg ttacagtcta gtgactccag cagcgtcctg caccacctgt ggtgttccac    36000
acctctgcta actcttgctc tcctccttct cctggattgc ccttctcacc tccttgccca    36060
ctccaccact caactcaggt gccacctcct gcaggaagct acctctgaat ctccaggaca    36120
ggccagtggc ccacccaggt ccattacacc ctgcccagtc ctgtcatttg ctacgtggtt    36180
ggtagccaca gtgcctggct taggaaagac tggttctagg aaaaacaatt tcattccctg    36240
tggccagctc caagccttcc cccgccaagc ttctccattc aggtctctgt gaatttaatt    36300
aattcatcca tccatcaaac aagtatttac tgagcactaa tatgtgctag gtactgctcc    36360
aggtgctgag gactcagcag tgaaaagatg actgctactc tcatgggaca tacaggatag    36420
tagggaaaag acagataatc aacaaggtca tttctgacca catctgtggt ttaagaaaaa    36480
gtcaagcaga gtgatgtgat acagagtaat ggtgggggag agggaggcct ccctgaagaa    36540
gtgacagtga attgagaagc gcatgtcaag gggttgccag gcagaggaaa taggacccac    36600
atgggcctag agtcaggagt gagcttgaag tgtctgagga acttaaaggc caatgtgacc    36660
agagggaagt gaacaaggtg aaaaagttgg gcagggggcca ggtccctaga tgcttctaag    36720
cagtagagtg atatgctctg gcttacccct gggtccgtgt accctggact ggaagaaagc    36780
aagggtggac ctggaaagac cactaggagg ctgctgttga tgggtgagag aggaagggggg    36840 ctgagagtag ggtcagggca gaggaggaga gacgctgtcg tgggctggcg gatggatgat    36900
ggggaagagg aacaaaggat gacttttttgg tttggggtct aagaaactgg gtggatgatt    36960
gagcaggtag agaaaaaatc agcgtgggag gaaaaaaaat caagacttct gttttggaca    37020
tggtgcaaac tgccttccag acatccacat agaggtatca ggatacagaa gtttggaact    37080
cacagaggaa gtcaaggctg gagattgaaa aaaaaaaaaa aaaaaaaaaa agtggggtta    37140
ttagcataga gggccaatat ggtgaaaccc tgtctctact gaaaatacaa aaattatcca    37200
ggcatggtgg catgcacctg taatcccagc tactcaggga ggctgaggca ggagaattgc    37260
ttgaacccag agatggggtg gaggttgcag taagctgaga tcgtgccatt gcactccagc    37320
ctgggtgaca gggcaagatt ccatctaaaa aaaaaaaaag ccactacagg atcaactaag    37380
agctcctaga gaaagaatag gtaggtagaa aagagtgtaa ggccaactac ctagccctgg    37440
gcattcattc cagctttcaa ctccagtgag agatgagaag gagagtgtgg aggtagatgg    37500
gaaatgagaa acaatgctgt gtccagagag ctaagagaag tcagtgtttc aagagagaca    37560
gagctgtcaa cttttgatgga tgcttctgag aagccaagca agttgaagac aaaaaaaaaa    37620
aaaatgatct ttggctctgc ccatatggcg atcgttggtg gccagggcca gagcttccat    37680
ccagcgatgg agactgcaga ctggctggag cgagcagcag agagaaggag agattaggaa    37740
gtgctgccag cacctataga cagctcttcc cagaagttat gagaagtaac agccacggtc    37800
actggagggg acatggatca aagaaagggc aggtgaagga ggggagatgt cggagcaggt    37860
tgtgtactga cgagaaggaa ccagtagaaa gggagaaact gatgcactca tcaaacccctt    37920 gtaatcacga tcatcttctg tgtgaattag ttctgggttc ctggaatagc atcgggaatc    37980
agccgcgctg acctttagca tttattctgt cactgttacg atagacttga gtttcctcag    38040
ttcttaagaa agtggaaata atactacctt atgtatgtaa gccacccccaa tcacacgtgc    38100
```

```
tttcatgcca tcttctcatt tgatgctcac aacaaaccaa ggtgtcagga caggatgtca    38160
tgcctgtccc taacctcaga gaagtagcca gcccagcact gcacagctcg ttaccagcag    38220
agcctggatc ccagccatct gcccatcgtg ctcagtctag tcaccctagc atctctccca    38280
ggaacagaac tgccctccct cctccaattg tgttactaag gaacgggtgt aaaaggcctt    38340
cagacaacag aaagtgagat catgggccag gtgtggtcat gagctcagat agtgaacttt    38400
cacctccctc cctggcaata ccctgtggtc aggagcaggc agattacaca aagagtggag    38460
gctagacgtt ccaaacagac tctgaatagg tgacagtgcc aggggctcat tcttctcagt    38520
gctggccaca ggttgggcct ggctgctggc taaaaggtgc cggggagggg gatacagcag    38580
ctcccagctc atcctcagag ggtcctggga tcaaaggtat ttacacccag ggatatttca    38640
gataaatctt ttcatctatg tggaaaacat acaaagtggc gcaagtgaga aactccgatt    38700
tcctaaggtt gacaagtcaa gtgcagtaat gatgtcatgg taaccaatat gtttccaaac    38760
tttcctaagg ttgactagcc ccatgcactt tgagaagttg gtaaatagga ttgtcgtcgt    38820
tttataaaat tgaaaacacg gtgtcttgca atcacagcca ctcacaaagg aagccagaga    38880
tggtcccagc ccctccgcag acttcctgtg gactcaggac tggtggtctc tcctgggcct    38940
tgctgtaccc ggcaaatcca ggggcacaga ctcaggttc tgccctgccg acagatgctg    39000
cctagccttc tgtgtgtcat aagtcaactc ccgctcagcc ccaggctgct gggtccctgc    39060
tgtgggccaa aaaccagcca cttcgctggt ttctatcccc cacccgttc ccgagggagg    39120 ggctctggtg tgagacaccc cctcagagag gaaagtgtct cccagctttg gagagaatcg    39180
aggtgtcctt tctctctctc cagctggaac cagtgggccg caagactacc tccaacaact    39240
tcacccacag ccgagccaaa ctcaagtgcc cctctcctgt gagtaaacgt cctgcctgcc    39300
ccaggtggaa cagatgcctg gggtgggggt tgtcctgtcc cctggaagca cagaggagtc    39360 cccgggatg ctccctcaaa tgcggcttca ctcactgccg tcttctcaaa tcccacctgt    39420
ccccagtgcc acggaaactt ctcagtgtgt gggcagccat ggagggaggg gagaggacgt    39480
tcaacagctc caaccgaagg gaggacagtc gctcagggag gcagatgagc actggcgggt    39540
gtctcgggtc acccattcct tccgaaagct ctgatgcatc ctcagtctta aagtgcacc    39600 aaggccaggc gtggtggctc acgcctataa tcccagcact ttgggaggcc gaggcggtca    39660
gatcacctga ggtctggagt acaagaccag cctggccaac atagtgaaac cccgtctcta    39720
gtaaaaatcc aaaagtcagc cgggcatggt ggcgggcgcc tgtcatccca gctactcagg    39780
aggctgaggc aggagaatca cttgaacccg ggaggcagag gttgcagtga gctgaggtca    39840
tgccactgca ctccagactg agtgacagag tgagactgtc tcaaaaataa agtgcatcaa    39900
gcagctgtcc cgtgccaggc agtatactag gatctgggga tcgggaggca aagataaaat    39960
agactcagtg tctgttcctg gagcctgcaa tggtcttcct ccctcgccac acccactgcc    40020
cttgcctggc ccaccttcga agcctgtgac ttgtctcccc agctctcctc tccctcttct    40080
ccatccaccc tacacttgct gccagacaca gatagacctt cctggaaata acttgcccca    40140
tcaaggctgc ttgaaatcct tgcctgatcc ctactgccca ttgaccagag tctggaggga    40200
gggtcacctc cctccatgat acacactgca ctcctggccg gtggatccat ctcccaggaa    40260
gccccacgac tgcccgcatc caggcctttc cttttgccat ctgttcctgg aggttcatct    40320
tccatctgct atgagaacat ccgctcctcc ccaggtccag atgttgcctt tactaagcga    40380
tggtttcacc gtctcttacc taccattcct gtctccagac actgacccat gtgggtctcc    40440
```

```
ttttctattt gtacctctca tgagacaccg acccagtctc ctttatgatg tgattgtttc    40500
tgcacatctc aacttcctcc tgggccacaa gaaaagatgt cacatcttaa ccctccagtc    40560
tcatcacagc ttccagcaag ggggctaaac acagcacgtg cccaattcac attcactgag    40620
aggagagtgg agagggcat aggaaggcaa gaacgcacac gatctgccca catgcctccc    40680
ctcccggccc ttctgatttg gggatctttc atctactaca aaaccagctg tccttccatg    40740
ctgcccttcc ctgatttctg ggtagtcctg ggatgggaga atggggacag ttgtgaccac    40800
gaggaagcag aggtgggagt tctacaggcc ccacagggct ctctgccatt ggtcacctat    40860
cagttcccaa tctttcaaaa tcaggtttga tggccaagga aacgctggtg agaaaccaaa    40920
agaaggttct agctgggtgt tgacctcttt agaggcccat cccgctaaag agggtttggg    40980
cacagcctaa atgagggagc tttacaaaag ggaagctctg tgaaaacgtg cagggttatc    41040
gcagcatctc aggaatgggg actaggcaag tcttggcttg gtgatggatg gttcacggag    41100
atcctttcca ctgaccccg ctcctcctcc acaggagagc ccttacctct acaccctgcg    41160
gaacagccga ttgctcccag accaggctga agaagccccc gaggtgctct actgggctgt    41220
cccagtggca gcgggagtcg gccttgtggt gggcatcatc gggacagtgg tctgaggtg    41280 caggagaggt ggccggaggg aagatcctcc aatgagcctg cgcactgtgg ccctctaggc    41340 ccggggggtgg gtcctcaccc taaactccct atagccactc tcttcaccgc cctctgcccc    41400
agccactccc ggccaccagg acatgcttca atgcctggtg ccataggaag cccaggggac    41460
agtcacaact tcttggggcc tgggcttctt ccaggcctat gctcctggaa tggatacatt    41520
taaataaagt ccaaagctat tttattcctg ggtttgcctg cgtgaagcac tcaccttcca    41580
tctcttgtgc agcccaggtg tgggagctgc cacttttgt ggcctgcctc cagcagggct    41640
gcccaagcca cgaccaacca gagcccaaac tgcctgccac cacgagcata tcctcaagtc    41700
accaaaccca ctatttcaaa ggcagaaaaa atgctggtca ccaggtggtg gctggaattt    41760
tggagctggc tggttgccat tcagtccaat ccaacacata cctattaagc aactgttttg    41820
tatccaggac aatgcgaagc actgaggtgc ctcctaggct gtgcatgtcg cagcctggca    41880
gagaggtcaa actccttcaa taaccaagaa gccacgtgat gatgtgtaac tactagggca    41940
tcagtaggta aatgtgtctg attgttttaa agaatagaaa gggttcttcg gggaaagttt    42000 cttggggag agcaaccttc acatgtcatt ttgggaaaag gaataaaaaa tgattgggac    42060
acaaatacct cctatattct caacctgatt ttctcaaggt gctaaattta ggaaaaaatt    42120
cctatttcta tatgcccagg tttctgaggg aaaactagag agagtctgaa aatatgggct    42180
gcattcactg agcccctgct aggggcgagg ccccgtgctg gaggccttcc acagatggtc    42240
tcttttatgc tgcacaaaag cccagggagg gggtaaaagg aaaatctttg aaaatagaag    42300
tgatgcttgc gcaacaccgt gaatgtacta acgccgcga attgttccat ttaaaatgat    42360
taattgtgta tcatgtgaat ttcacttcaa taaaaaagaa tccagggagg tagacatcat    42420
ctgcattgta aacctctctc tgatcctgaa gtccgggatg ataaagagcc tgagtcacaa    42480
tcccggatgc aacactgaaa tgctgtgccc tgaagctgcc ttcgccagcc tgagcccagt    42540
gtcccaggct ctgcatctgt aaaaactgga gtaagagtac acattttgct tatctcacgg    42600
cgctgctgaa aaataaggaa ccgtgtgtga acctctaact ctaaaatgct gcacaactga    42660
aaatggcctt tttcctcggt gaagagttgg gataaggccc agactgttgg ggaagatgtg    42720
agacccagag atgagtttgg ggaaatgggg taataacata tgggtggaga gtgcccgcct    42780
tcctctcagg gaggttcatc accttatctc tttctgtcac aacagagaac ccggaggacc    42840
```

```
tatacccagt tccgtgttct tctgggcttc agtgtctgtt tctatacaat gggaacagca    42900
tgcattcccc tgcttttcc  tatagactgg aaaacgtggt gaccaagtca cacatcccag    42960
cttatgctcc cggcttaaga cagtgtaacg acaaaggtaa cccttacact cctggtttga    43020
gacagtataa cgacaaaggt aacataggaa gtcaaggagt tcgcttcacc gcccctcccc    43080
ccaccccacc cttttttttt cctgcaagtt tctattcttc ccgcagctcc tacctcaaag    43140
cagcatggat tcataaccac aggctcccct cattagggct tggggaggga gggtgttgga    43200
atccacactg ccagagtaat ccagactaaa acatcaacaa atggtcccag ctggttcacc    43260
aaggaacact tggcaaaaca aagaaatcct gtctggagcg acacggacac agccacaaac    43320
cagtcaccaa attcccagca agtatgtgct aagaagccaa aaattaaaaa tacgtgagaa    43380
gcacccactt gaaattggtg gtattacata catacactgg ctgtgcgcca tggggttttt    43440
ctgtaggaaa atgtccagtc tagctagaac ggcacccaca gccacaccat gagcaaagcc    43500
accaaatacc tgaggaagcc acagtccatg gcactcccca tgg                     43543
```